US009085575B2

(12) United States Patent
Rabot et al.

(10) Patent No.: US 9,085,575 B2
(45) Date of Patent: Jul. 21, 2015

(54) TRI- AND TETRACYCLIC PYRAZOLO[3,4-B]PYRIDINE COMPOUNDS AS ANTINEOPLASTIC AGENT

(75) Inventors: Rémi Rabot, Toulouse (FR); Karim Bedjeguelal, Toulouse (FR); El Bachir Kaloun, Roquettes (FR); Philippe Schmitt, Nailloux (FR); Nicolas Rahier, Ayguesvives (FR); Patrice Mayer, Pompertuzat (FR); Emmanuel Fournier, Muret (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/111,098

(22) PCT Filed: Apr. 12, 2012

(86) PCT No.: PCT/EP2012/056637
§ 371 (c)(1),
(2), (4) Date: Oct. 10, 2013

(87) PCT Pub. No.: WO2012/140114
PCT Pub. Date: Oct. 18, 2012

(65) Prior Publication Data
US 2014/0031362 A1    Jan. 30, 2014

(30) Foreign Application Priority Data

Apr. 12, 2011 (FR) ...................... 11 53200

(51) Int. Cl.
| | | |
|---|---|---|
| C07D 471/00 | (2006.01) |
| C07D 471/04 | (2006.01) |
| C07D 471/14 | (2006.01) |
| C07D 493/14 | (2006.01) |
| A61K 31/437 | (2006.01) |
| A61K 31/4375 | (2006.01) |
| A61K 31/4745 | (2006.01) |
| A61K 31/496 | (2006.01) |
| A61K 45/06 | (2006.01) |
| C07D 491/147 | (2006.01) |

(52) U.S. Cl.
CPC ............ *C07D 471/04* (2013.01); *A61K 31/437* (2013.01); *A61K 31/4375* (2013.01); *A61K 31/4745* (2013.01); *A61K 31/496* (2013.01); *A61K 45/06* (2013.01); *C07D 471/14* (2013.01); *C07D 491/147* (2013.01); *C07D 493/14* (2013.01)

(58) Field of Classification Search
CPC .................................... C07D 471/04
USPC ......................................... 546/64
See application file for complete search history.

(56) References Cited

U.S. PATENT DOCUMENTS

| | | | | |
|---|---|---|---|---|
| 7,872,014 B2 * | 1/2011 | Anand et al. | ................... | 514/291 |
| 2007/0032515 A1 * | 2/2007 | Anand et al. | ................... | 514/291 |
| 2010/0113415 A1 | 5/2010 | Rajapakse et al. | | |

OTHER PUBLICATIONS

West (Solid-State Chemistry and Its Applications, 1984, John Wiley & Sons).*
International Search Report for PCT/EP2012/056637 dated May 18, 2012.
Al-Kaabi, S. S. and G. E. H. Elgemeie, "Studies on Fused 2(1*H*)-Pyridenethiones: New Routes for the Synthesis of Fused 1*H*-Pyrazolo[3,4-*b*]pyridines and Fused Thieno[2,3-*b*]pyridines," Bull. Chem. Soc. Jpn. (1992), vol. 65, pp. 2241-2245.
Baraldi et al., "Synthesis and Biological Effects of Novel 2-Amino-3-naphthoylthiophenes as Allosteric Enhancers of the $A_1$ Adenosine Receptor," J. Med. Chem. (2003), vol. 46, pp. 794-809.
Bogdanowicz-Szwed, K. and A. Palasz, "Synthesis of Functionalized 3,4-Dihydro-2*H*-pyrans by Heter-*Diels-Alder* Reaction of an Enaminoketone with Enol Ethers," Monatshefte fur Chemie (1995), vol. 126, 1341-1348.
Bowman et al., "Oxidation during Reductive Cyclisations using $Bu_3SnH$," Tetrahedron (1991), vol. 47, No. 48, pp. 10119-10128.
Guo et al., "Synthesis of 7-benzyl-5-(piperidin-1-yl)-6,7,8,9-tetrahydro-3*H*-pyrazolo[3,4-*c*]-[2,7]naphthyridin- 1-ylamine and its analogs as bombesin receptor subtype-3 agonists," Bioorganic & Medicinal Chemistry Letters (2010), vol. 20, pp. 2785-2780.
Kobayashi et al., "Synthesis of (Z)-2-[(Z)-3-Alkylideneisobenzofuran-1(3*H*)-ylidene]acetic Acid Derivatives by Sequential Coupling-Cyclization between 3-(2-Iodophenyl)-3-oxopropanoic Acid Derivatives and Terminal Alkynes," Synthesis (2008), No. 7, pp. 1094-1098.
Marsais et al., "Directed *ortho*-Lithiation of Chloroquinolines. Application to Synthesis of 2,3-Disubstituted Quinolines," J. Heterocyclic Chem. (1989), vol. 26, pp. 1589-1594.

(Continued)

*Primary Examiner* — Nizal Chandrakumar
(74) *Attorney, Agent, or Firm* — Birch, Stewart, Kolasch & Birch, LLP

(57) ABSTRACT

The present invention relates to compounds of following general formula (I): and to the pharmaceutically acceptable salts of same, the tautomers of same, the stereoisomers or mixture of stereoisomers in any proportions of same, such as a mixture of enantiomers, notably a racemic mixture, as well as to methods for preparing same and uses of same, notably as an antineoplastic agent.

24 Claims, No Drawings

(56) References Cited

OTHER PUBLICATIONS

Rao, U. and K. K. Balasubramanian, "Claisen Rearragement of Aryl Propargyl Ethers in Poly(Ethylene Glycol)—A Remarkable Substituent and Solvent Effect," Tetrahedron Letters (1983), vol. 24, No. 45, pp. 5034-5024.

Tang et al., "Asymmetric conjugate additions to 1,1'-diactivated cyclic enones—a comparative study," Tetrahedron: *Asymmetry* (2009), vol. 20, pp. 1881-1891.

Svetlik et al., "Monastrol analogs: A synthesis of pyrazolopyridine, benzopyranopyrazolopyridine, and oxygen-bridged azolopyrimidine derivatives and their biological screening", Bioorganic & Medicinal Chemistry Letters, vol. 20 (2010) pp. 4073-4076.

* cited by examiner

TRI- AND TETRACYCLIC PYRAZOLO[3,4-B]PYRIDINE COMPOUNDS AS ANTINEOPLASTIC AGENT

The present invention relates to pyrazolopyridine derivatives, as well as to the therapeutic use of same, notably in the treatment of cancer, and to a method for synthesizing same.

Protein kinases are enzymes that play a key role in cell signal transduction. They are involved in physiological processes such as cell proliferation, mitosis, differentiation, cell invasion and mobility, and apoptosis, for example. These enzymes are regarded as playing an important role during the various stages of tumor development, and thus constitute important pharmaceutical targets for cancer treatment.

Tyrosine kinase receptors (TKRs) form a particular class of protein kinases among which, among others, mention may be made of ALK, EGFR, HER2, PDGFR, KIT, VEGFR, IGFR, FGFR, TRK, AXL, MER, MET, RON and RET. In this subfamily, ALK is regarded as a particularly relevant target because it is likely to give rise to an activating chromosomal translocation that generates the production of new tumors.

Several cases of chromosomal translocations involving ALK, related to cancer pathologies, have already been documented. For example, the fusion protein NPM-ALK is associated with anaplastic large-cell lymphoma (ALCL) for which an optimal treatment remains to be developed. Similarly, the fusion protein EML4-ALK is associated with tumor development in a subpopulation of patients suffering from non-small cell lung cancer. Mutated forms of ALK have also been observed in neuroblastoma.

The compounds of the present invention thus have the property of inhibiting or modulating the enzymatic activity of protein kinases, for example ALK, and consequently can be used as a drug, for example in the treatment of various diseases, notably proliferative diseases, such as cancer, inflammation or affections of the central nervous system.

More particularly, the present invention has as an object a compound of following general formula (I):

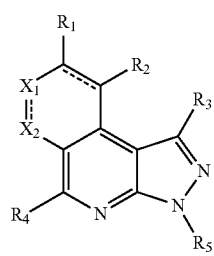

(I)

or a pharmaceutically acceptable salt or solvate of same, a tautomer of same, or a stereoisomer or mixture of stereoisomers in any proportions of same, such as a mixture of enantiomers, notably a racemic mixture,
wherein:
- ---- represents a double or single bond,
- $X_1$ represents a single bond, O, S or $NR_6$ when ---- represents a single bond between $X_1$ and $X_2$, or
- $X_1$ represents N when ---- represents a double bond between $X_1$ and $X_2$,
- $X_2$ represents C=O, C=S or $CH_2$ when ---- represents a single bond between $X_1$ and $X_2$, or
- $X_2$ represents a CH, $C(OR_7)$, $C(NR_8R_9)$ or $C(SR_{10})$ group when ---- represents a double bond between $X_1$ and $X_2$,
- $R_1$ and $R_2$ each represent, independently of each other, a hydrogen atom, a halogen atom, a $(C_2-C_6)$alkenyl, $(C_2-C_6)$alkynyl, CN, $NO_2$, $OR_{11}$, $SR_{12}$, $NR_{13}R_{14}$, $COR_{15}$, $CO_2R_{16}$, $OCO_2R_{17}$, $CONR_{18}R_{19}$, $NR_{20}COR_{21}$, $NR_{22}SO_2R_{23}$, $SO_2R_{24}$, $SOR_{25}$, aralkyl, $(C_1-C_6)$alkyl, aryl, heteroaryl, carbocycle or heterocycle group,
  the $(C_2-C_6)$alkenyl, $(C_2-C_6)$alkynyl chains as well as the aromatic or non-aromatic rings of said group (in particular the aryl, heteroaryl, carbocycle and heterocycle rings and the aryl core of the aralkyl moiety) being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, $(C_1-C_6)$alkyl, aryl, heteroaryl, carbocycle or heterocycle group,
  the $(C_1-C_6)$alkyl chains as well as the rings of the whole being optionally substituted by one or more groups selected from $OR_{43}$, $NR_{44}R_{45}$, heterocycle and $(C_1-C_6)$-alkyl, or
- $R_1$ and $R_2$ together form, with the carbon atoms that carry them, a ring selected from aryl, heteroaryl, carbocycle and heterocycle,
  said ring being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, $(C_1-C_6)$alkyl, aryl, heteroaryl, carbocycle, heterocycle group,
  the $(C_1-C_6)$alkyl chains as well as the rings of the whole being optionally substituted by one or more groups selected from $OR_{43}$, $NR_{44}R_{45}$, —C(O)O—$(C_1-C_6)$-alkyl, heterocycle and $(C_1-C_6)$-alkyl, and
- $R_3$ represents a hydrogen atom, an —$NR_{46}R_{47}$, —$CONR_{46}R_{47}$, —$NO_2$, —$NR_{48}$-aryl, —$NR_{48}$-aralkyl, —$NR_{48}$-heteroaryl, —$NR_{48}$-carbocycle, —$NR_{48}$-heterocycle, —$NR_{48}$CO-aryl, —$NR_{48}$CO—$(C_1-C_6)$alkyl, —$NR_{48}$CO-aralkyl, —$NR_{48}$CO-heteroaryl, —$NR_{48}$Cβ-carbocycle, —$NR_{48}$CO-heterocycle, —$NR_{48}SO_2$—$(C_1-C_6)$alkyl, —$NR_{48}SO_2$-aryl, —$NR_{48}SO_2$-aralkyl, —$NR_{48}SO_2$-heteroaryl, —$NR_{48}SO_2$-carbocycle, —$NR_{48}SO_2$-heterocycle, —$OR_{49}$, —$CO_2R_{49}$, aryl, heteroaryl, carbocycle, heterocycle, aralkyl, or $(C_1-C_6)$alkyl group,
  the $(C_1-C_6)$alkyl chains as well as the aromatic or non-aromatic rings of said group (in particular the aryl, heteroaryl, carbocycle and heterocycle rings and the aryl core of the aralkyl moiety) being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, $(C_1-C_6)$alkyl, aryl, heteroaryl, carbocycle, heterocycle group,
  the $(C_1-C_6)$alkyl chains as well as the rings of the whole being optionally substituted by one or more groups selected from $OR_{43}$, $NR_{44}R_{45}$, heterocycle and $(C_1-C_6)$-alkyl, and
- $R_4$ represents an aryl, aralkyl, heteroaryl, carbocycle, or heterocycle group, said group being optionally substituted by one or more groups selected from a halogen atom, a CN, $NO_2$, $OR_{50}$, $SR_{51}$, $NR_{52}R_{53}$, $COR_{54}$, $CO_2R_{55}$, $OCO_2R_{56}$, $CONR_{57}R_{58}$, $NR_{59}COR_{60}$, $NR_{61}SO_2R_{62}$, $SO_2NR_{63}R_{64}$, $SO_2R_{65}$, $SOR_{66}$, $(C_1-C_6)$alkyl, $(C_1-C_6)$haloalkyl, $(C_1-C_6)$haloalkoxy or $OCOR_{67}$ group,
- $R_5$ represents a hydrogen atom or a CO—$(C_1-C_6)$alkyl or $CO_2$—$((C_1-C_6)$alkyl) group, with:

$R_6$ representing a hydrogen atom, an OH group, an aralkyl or $(C_1-C_{10})$alkyl group, the $(C_1-C_{10})$alkyl chains as well as the rings of the whole being optionally substituted by one or more groups selected from halogen; $OR_{68}$; $NR_{69}R_{70}$; heterocycle optionally substituted by one or more groups selected from $OR_{68}$, $NR_{69}R_{70}$ and $(C_1-C_6)$alkyl, $R_7$ and $R_{10}$ each representing, independently of each other, a hydrogen atom or a $(C_1-C_{10})$alkyl group, the $(C_1-C_{10})$alkyl groups being optionally substituted by one or more groups selected from halogen; $OR_{68}$; $NR_{69}R_{70}$; and heterocycle optionally substituted by one or more groups among $OR_{68}$, $NR_{69}R_{70}$ or $(C_1-C_6)$alkyl, $R_8$ and $R_9$ each representing, independently of each other, a hydrogen atom or a $(C_1-C_6)$alkyl group, or $R_8$ and $R_9$ together forming, with the nitrogen atom that carries them, a heteroaryl or heterocycle group optionally substituted by a $(C_1-C_6)$alkyl group, $R_{11}$ to $R_{42}$ and $R_{50}$ to $R_{66}$ each representing, independently of each other, a hydrogen atom or a $(C_1-C_6)$-alkyl, aryl or aralkyl group, $R_{43}$, $R_{46}$ to $R_{49}$ and $R_{68}$ each representing, independently of each other, a hydrogen atom or a $(C_1-C_6)$-alkyl group, $R_{44}$, $R_{45}$, $R_{69}$, $R_{70}$, $R_{72}$ and $R_{73}$ each representing, independently of each other, a hydrogen atom or a $(C_1-C_6)$ alkyl group, or $R_{44}$ and $R_{45}$ together forming, with the nitrogen atom that carries them, an optionally substituted heterocycle group, or $R_{69}$ and $R_{70}$ together forming, with the nitrogen atom that carries them, an optionally substituted heterocycle group, or $R_{72}$ and $R_{73}$ together forming, with the nitrogen atom that carries them, an optionally substituted heterocycle group, and $R_{67}$ representing a hydrogen atom or an $NR_{72}R_{73}$, optionally substituted $(C_1-C_6)$alkyl and optionally substituted $(C_2-C_6)$alkenyl group.

In the present invention, "pharmaceutically acceptable" refers to that which is useful in the preparation of a pharmaceutical composition that is generally safe, nontoxic and neither biologically nor otherwise undesirable and that is acceptable for veterinary and human pharmaceutical use.

"Pharmaceutically acceptable salt or solvate" of a compound refers to salts and solvates that are pharmaceutically acceptable, as defined herein, and that have the desired pharmacological activity of the parent compound. Such salts and solvates comprise:

(1) Solvates acceptable for the therapeutic use of compounds of the present invention comprising conventional solvates such as those formed during the last step of preparation of compounds of the invention due to the presence of solvents. As an example, mention may be made of solvates due to the presence of water or ethanol.

(2) Acid addition salts formed with organic acids or inorganic acids. As an example, mention may be made of salts derived from inorganic acids such as hydrochloric, hydrobromic, phosphoric or sulfuric acids, and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic or lactic acids.

(3) Salts formed by deprotonation of the parent molecule. As an example, mention may be made of salts derived from inorganic bases such as soda, potash or calcium hydroxide and salts derived from organic bases such as lysine or arginine.

In the context of the present invention, "stereoisomer" refers to a geometric isomer or an optical isomer. Geometric isomers result from the different position of substituents on a double bond which can then have a Z or E configuration. Optical isomers result notably from the different position in space of substituents on a carbon atom comprising four different substituents. This carbon atom thus constitutes a chiral or asymmetrical center. Optical isomers include diastereoisomers and enantiomers. Optical isomers that are mirror images of each other but are non-superimposable are enantiomers. Optical isomers that are not mirror images of each other are diastereoisomers.

In the context of the present invention, "tautomer" refers to a constitutional isomer of the compound obtained by prototropy, i.e., by migration of a hydrogen atom and a change in location of a double bond. The different tautomers of a compound are generally interconvertible and are in equilibrium in solution in proportions which may vary according to the solvent used, the temperature or the pH.

In the context of the present invention, "halogen atom" refers to fluorine, chlorine, bromine and iodine atoms.

In the context of the present invention, "$(C_1-C_6)$alkyl" group refers to a saturated linear or branched hydrocarbon chain comprising 1 to 6, preferably 1 to 4, carbon atoms. As an example, mention may be made of methyl, ethyl, propyl, isopropyl, butyl, isobutyl, sec-butyl, tert-butyl, pentyl or hexyl groups.

In the context of the present invention, "$(C_2-C_6)$alkenyl" or "alkene" group refers to an unsaturated linear or branched hydrocarbon chain comprising 2 to 6, preferably 2 to 4, carbon atoms and comprising at least one double bond. As an example, mention may be made of the vinyl group.

In the context of the present invention, "$(C_2-C_6)$alkynyl" or "alkyne" group refers to an unsaturated linear or branched hydrocarbon chain comprising 2 to 6, preferably 2 to 4, carbon atoms and comprising at least one triple bond. As an example, mention may be made of the —C≡CH group.

In the context of the present invention, "$(C_1-C_6)$alkoxy" group refers to a $(C_1-C_6)$alkyl group, such as defined above, linked to the rest of the molecule via an oxygen atom. As an example, mention may be made of the methoxy, ethoxy, propoxy, isopropoxy, butoxy or tert-butoxy groups.

In the context of the present invention, "$(C_1-C_6)$haloalkyl" refers to a $(C_1-C_6)$alkyl group, such as defined above, wherein one or more hydrogen atoms have been replaced by a halogen atom such as defined above. It may be in particular a $CF_3$ group.

In the context of the present invention, "$(C_1-C_6)$haloalkoxy" refers to a $(C_1-C_6)$halogenoalkyl group, such as defined above, linked to the rest of the molecule via an oxygen atom.

In the context of the present invention, "aryl" refers to an aromatic group comprising preferably from 6 to 14 carbon atoms and comprising one or more fused rings, such as, for example, a phenyl or naphthyl group. Advantageously, it is a phenyl group.

In the context of the present invention, "aralkyl" refers to a saturated linear or branched hydrocarbon chain comprising 1 to 6, preferably 1 to 4, carbon atoms, substituted on one of these carbon atoms by an aryl group such as defined above, and preferably a phenyl group. Advantageously, it is a benzyl or phenethyl group.

In the context of the present invention, the term "aryloxy group" refers to any aryl group such as defined above, linked to the molecule via an oxygen atom. It may be in particular a phenyloxy group.

In the context of the present invention, "heteroaryl" refers to a cyclic aromatic group comprising 5 to 7 atoms included in the ring or a bicyclic aromatic group comprising 9 to 11 atoms included in the two rings, notably fused, including one or more heteroatoms, advantageously 1 to 4 and even more advantageously 1 or 2, such as, for example, sulfur, nitrogen or oxygen atoms, the other atoms included in the ring or rings being carbon atoms. Examples of heteroaryl groups include furyl, thienyl, pyrrolyl, pyridinyl, pyrimidinyl, pyrazolyl, imidazolyl, triazolyl, tetrazolyl or indyl groups.

In the context of the present invention, "carbocycle" refers to either a stable hydrocarbon monocycle containing from 4 to 8 atoms included in the ring, or a stable hydrocarbon bicycle containing from 8 to 12 atoms in the two rings, notably fused, which may be saturated or unsaturated but non-aromatic. It may be notably a cyclopropyl, cyclopentyl, cyclohexyl, cyclohexenyl or cycloheptyl group.

In the context of the present invention, "heterocycle" refers to either a stable monocycle containing from 4 to 7 atoms included in the ring, or a stable bicycle containing from 8 to 12 atoms included in the two rings, the two rings notably being fused or linked together via a single bond, and being saturated or unsaturated, 1 to 4 of the atoms included in the rings being a heteroatom selected independently from sulfur, nitrogen and oxygen atoms, the other cyclic atoms being carbon atoms. As an example, mention may be made of furan, pyrrole, thiophene, thiazole, isothiazole, oxadiazole, imidazole, oxazole, isoxazole, pyridine, piperidine, morpholine, pyrazine, piperazine, tetrahydropyran, pyrimidine, quinazoline, quinoline, quinoxaline, benzofuran, benzothiophene, indoline, indolizine, benzothiazole, benzothienyl, benzopyran, benzoxazole, benzo[1,3]dioxole, benzisoxazole, benzimidazole, chromane, chromene, dihydrobenzofuran, dihydrobenzothienyl, dihydroisoxazole, isoquinoline, dihydrobenzo[1,4]dioxine, imidazo[1,2-a]pyridine, furo[2,3-c]pyridine, 2,3-dihydro-1H-indene, [1,3]dioxolo[4,5-c]pyridine, pyrrolo[1,2-c]pyrimidine, pyrrolo[1,2-a]pyrimidine, tetrahydronaphthalene, benzo[b][1,4]oxazin.

In the context of the present invention, "optionally substituted" means that said group is, for example, optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, $(C_1-C_6)$alkyl, aryl, heteroaryl, carbocycle, and heterocycle group.

More particularly, "optionally substituted heterocycle" means than the heterocycle such as defined above is optionally substituted by one or more groups selected from $NR_{28}R_{29}$, $CO_2R_{31}$, and $(C_1-C_6)$alkyl.

In particular, $X_1$ will represent a single bond, O or $NR_6$ when ---- represents a single bond between $X_1$ and $X_2$, or will represent N when ---- represents a double bond between $X_1$ and $X_2$, with $R_6$ such as defined above.

In particular, $R_6$ will represent a hydrogen atom; an OH group; or a $(C_1-C_{10})$alkyl group optionally substituted by an $NR_{69}R_{70}$ group.

$X_2$ will represent more particularly C=O or C=S, and advantagesouly C=O when ---- represents a single bond between $X_1$ and $X_2$, or will represent a CH or $C(OR_7)$ group, when ---- represents a double bond between $X_1$ and $X_2$, with $R_7$ such as defined above and in particular with $R_7$ representing a hydrogen atom or a $(C_1-C_6)$alkyl group.

$$X_1\text{----}X_2$$

can represent in particular a —C(=O)—, —O—C(=O)—, —$NR_6$—C(=O)—, —N=CH— or —N=C($OR_7$)— group with $R_6$ and $R_7$ such as defined above, and in particular with $R_6$ representing a hydrogen atom; an OH group; or a $(C_1-C_{10})$ alkyl group optionally substituted by an $NR_{69}R_{70}$ group; and $R_7$ representing a hydrogen atom or a $(C_1-C_6)$alkyl group.

According to a particular embodiment of the invention, $R_1$ and $R_2$ together form, with the carbon atoms that carry them, a ring selected from an aryl, a heteroaryl, a carbocycle and a heterocycle, and notably an aryl or a heteroaryl, said ring being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, $(C_1-C_6)$alkyl, aryl, heteroaryl, carbocycle and heterocycle group, and in particular selected from a halogen atom, an $OR_{26}$, $SR_{27}$, $NR_{28}R_{29}$, $(C_1-C_6)$alkyl and heterocycle group, the $(C_1-C_6)$alkyl chains as well as the rings of the whole being optionally substituted by one or more groups selected from $OR_{43}$, $NR_{44}R_{45}$, —C(O)O—$(C_1-C_6)$-alkyl, heterocycle and $(C_1-C_6)$-alkyl.

Advantageously, $R_1$ and $R_2$ together form, with the carbon atoms that carry them, an aryl ring (such as phenyl) or heteroaryl ring (such as furan), said ring being optionally substituted by one or more groups selected from a halogen atom, an $OR_{26}$, $SR_{27}$, $NR_{28}R_{29}$, $(C_1-C_6)$alkyl and heterocycle group, the $(C_1-C_6)$alkyl chains as well as the rings of the whole being optionally substituted by one or more groups selected from $OR_{43}$, $NR_{44}R_{45}$, —C(O)O—$(C_1-C_6)$-alkyl, heterocycle and $(C_1-C_6)$-alkyl.

In particular, $R_1$ and $R_2$ together form, with the carbon atoms that carry them, a furan ring optionally substituted by a $(C_1-C_6)$alkyl group, such as methyl; or a phenyl ring optionally substituted by one of the following groups:

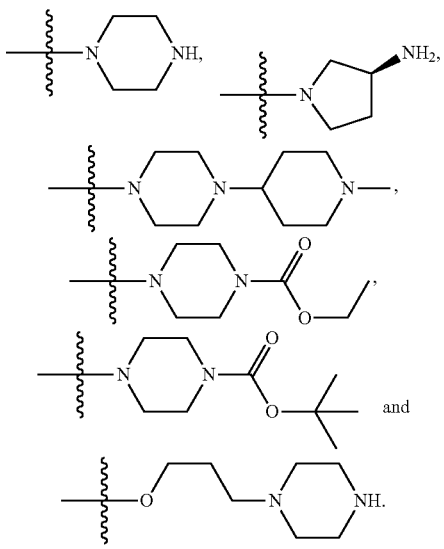

According to another particular embodiment of the invention, $R_1$ and $R_2$ each represent, independently of each other, a hydrogen atom, a halogen atom, or a $(C_2-C_6)$alkenyl, $(C_2-C_6)$ alkynyl, aralkyl, $(C_1-C_6)$alkyl, aryl, heteroaryl, carbocycle or heterocycle group, in particular a hydrogen atom or an aryl or heteroaryl group, notably a hydrogen atom or an aryl group such as phenyl, the ($C_2$-$C_6$)alkenyl, ($C_2$-$C_6$)alkynyl chains as well as the aromatic or non-aromatic rings of the whole being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, ($C_1$-$C_6$)alkyl, aryl, heteroaryl, carbocycle and heterocycle group; and in particular selected from a halogen atom, an $OR_{26}$, $SR_{27}$, $NR_{28}R_{29}$, ($C_1$-$C_6$)alkyl, aryl, heteroaryl, carbocycle, heterocycle group; and notably selected from $OR_{26}$, ($C_1$-$C_6$)alkyl or heterocycle, or unsubstituted, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl.

Notably, $R_1$ and $R_2$ may each represent, independently of each other, a hydrogen atom or an aryl group such as phenyl, the aryl ring being optionally substituted by one or more groups selected from $OR_{26}$, ($C_1$-$C_6$)alkyl and heterocycle; and notably selected from heterocycles, the ($C_1$-$C_6$)alkyl chains as well as the rings of the whole being optionally substituted by one or more groups selected from $NR_{44}R_{45}$ and ($C_1$-$C_6$)-alkyl.

In particular, $R_1$ and $R_2$ may be selected, independently of each other, from a hydrogen atom and a phenyl group optionally substituted by a heterocycle such as piperazine.

$R_3$ can represent advantageously a hydrogen atom, an aralkyl, ($C_1$-$C_6$)alkyl, —$NR_{46}R_{47}$, —$NR_{48}CO$-aryl, —$NR_{48}CO$—($C_1$-$C_6$)alkyl, —$NR_{48}CO$-aralkyl, —$NR_{48}CO$-heteroaryl, —$NR_{48}SO_2$—($C_1$-$C_6$)alkyl, —$NR_{48}SO_2$-aryl, —$NR_{48}SO_2$-aralkyl, —$NR_{48}SO_2$-heteroaryl, aryl, heteroaryl, or heterocycle group, the ($C_1$-$C_6$)alkyl chains as well as the aromatic or non-aromatic rings of said group (in particular the aryl, heteroaryl, carbocycle and heterocycle rings and the aryl core of the aralkyl moiety) being optionally substituted by one or more groups selected from a halogen atom, an $NO_2$, $NR_{28}R_{29}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, ($C_1$-$C_6$)alkyl, aryl, heteroaryl, carbocycle and heterocycle group, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl.

According to a first particular embodiment of the invention, $R_3$ can represent an aralkyl, ($C_1$-$C_6$)alkyl, —$NR_{46}R_{47}$, —$NR_{48}CO$-aryl, —$NR_{48}CO$—($C_1$-$C_6$)alkyl, —$NR_{48}CO$-aralkyl, —$NR_{48}CO$-heteroaryl, —$NR_{48}SO_2$—($C_1$-$C_6$)alkyl, —$NR_{48}SO_2$-aryl, —$NR_{48}SO_2$-aralkyl, or —$NR_{48}SO_2$-heteroaryl group, the ($C_1$-$C_6$)alkyl chains as well as the aromatic or non-aromatic rings of said group (in particular the aryl, heteroaryl rings and the aryl core of the aralkyl moiety) being optionally substituted by one or more groups selected from aryl, heteroaryl, carbocycle and heterocycle, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl.

In particular, $R_3$ can represent a ($C_1$-$C_6$)alkyl, —$NR_{46}R_{47}$, —$NR_{48}CO$-aryl, —$NR_{48}CO$—($C_1$-$C_6$)alkyl, —$NR_{48}CO$-aralkyl, or —$NR_{48}CO$-heteroaryl group, the aromatic or non-aromatic rings of said group (in particular the aryl, heteroaryl rings, and the aryl core of the aralkyl moiety) being optionally substituted by one or more groups selected from aryl, heteroaryl, carbocycle and heterocycle, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl, and in particular ($C_1$-$C_6$)-alkyl.

$R_3$ can represent in particular a $CH_3$, $NH_2$, —NH—C(O)—$CH_3$ or

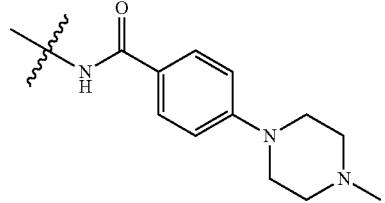 [SMILES: *NC(=O)c1ccc(N2CCN(C)CC2)cc1]

group.

$R_3$ can represent in particular a $CH_3$ or $NH_2$ group.

According to a second particular embodiment of the invention, $R_3$ can represent an aryl, heteroaryl or heterocycle group, in particular aryl or heteroaryl, said group being optionally substituted by one or more groups selected from a halogen atom, an $NO_2$, $NR_{28}R_{29}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, ($C_1$-$C_6$)alkyl, aryl, heteroaryl, carbocycle, heterocycle group, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl.

$R_3$ can represent in particular an aryl or heteroaryl group, said group being optionally substituted by one or more groups selected from aryl, heteroaryl, carbocycle, heterocycle, the whole being optionally substituted by one or more groups selected from $OR_{43}$, $NR_{44}R_{45}$, heterocycle and ($C_1$-$C_6$)-alkyl, and in particular ($C_1$-$C_6$)-alkyl.

$R_3$ can represent notably a thiophene, furan or

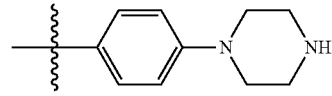 [SMILES: *c1ccc(N2CCNCC2)cc1]

group.

$R_4$ can represent more particularly an aryl, aralkyl, heteroaryl, carbocycle or heterocycle group, advantageously aryl, heteroaryl or aralkyl, notably aryl (such as phenyl) or aralkyl (such as benzyl), said group being optionally substituted by one or more groups selected from a halogen atom, an $OR_{50}$, $CO_2R_{55}$, $OCO_2R_{56}$, ($C_1$-$C_6$)alkyl, ($C_1$-$C_6$)haloalkyl or $OCOR_{67}$ group; in particular selected from F, $CF_3$, $OCH_3$, $OCH_2CH_3$, COOH, OC(O)$CH_3$, OC(O)C($CH_3$)$_3$, OC(O)OCH$_2$CH$_3$ or OC(O)CH$_2$CH$_2$C(O)OCH$_2$CH$_3$.

$R_5$ can represent in particular a hydrogen atom or a —C(O)—$CH_3$, —C(O)O—$CH_2CH_3$ or —C(O)O—C($CH_3$)$_3$ group. $R_5$ can represent more particularly a hydrogen atom.

According to a particular embodiment of the invention, the compounds according to the invention will be compounds of general formula (I) or a pharmaceutically acceptable salt of same wherein:

---- between the carbon atoms carrying the $R_1$ and $R_2$ groups represents a double bond, ---- between $X_1$ and $X_2$ represents a double or single bond, $X_1$ represents a single bond, O, or $NR_6$ when ---- represents a single bond between $X_1$ and $X_2$, or $X_1$ represents N when ---- represents a single or double bond, preferably double, between $X_1$ and $X_2$, $X_2$ represents C=O when ---- represents a single bond between $X_1$ and $X_2$, or $X_2$ represents a CH or $C(OR_7)$ group, when ---- represents a double bond between $X_1$ and $X_2$, $R_1$ and $R_2$ each represent, independently of each other, a hydrogen atom or an aryl group such as phenyl optionally substituted by a piperazine, or $R_1$ and $R_2$ together form, with the carbon atoms that carry them, a ring selected from an aryl, such as phenyl, and a heteroaryl, such as a furan, said ring being optionally substituted by one or more groups selected from $OR_{26}$, $(C_1-C_6)$alkyl, or heterocycle, the $(C_1-C_6)$alkyl chains as well as the rings (notably heterocycle) of the whole being optionally substituted by one or more groups selected from $NR_{44}R_{45}$, —C(O)O—$(C_1-C_6)$-alkyl, heterocycle and $(C_1-C_6)$-alkyl, $R_3$ represents a $(C_1-C_6)$alkyl, $NR_{46}R_{47}$, $NR_{48}CO$-aryl, $NR_{48}CO$—$(C_1-C_6)$alkyl, aryl, or heteroaryl group, the aryl group being optionally substituted by a heterocycle, said heterocycle being optionally substituted by one or more groups selected from $NR_{44}R_{45}$ and $(C_1-C_6)$-alkyl, and $R_4$ represents an aryl group such as phenyl, or aralkyl such as benzyl, the aromatic rings of said group being optionally substituted by one or more groups selected from a halogen atom, an $OR_{50}$, $CO_2R_{55}$, $OCO_2R_{56}$, $(C_1-C_6)$alkyl, $(C_1-C_6)$haloalkyl, $OCOR_{67}$ group, $R_5$ represents a hydrogen atom, or a CO—$(C_1-C_6)$alkyl or $CO_2$—$((C_1-C_6)$alkyl) group.

The compounds of the invention may be selected notably among the compounds cited in the following table (I):

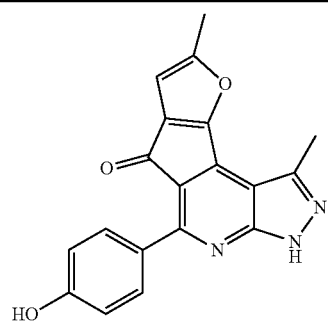

01

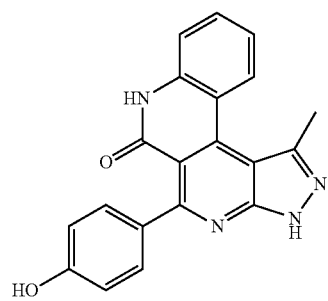

02

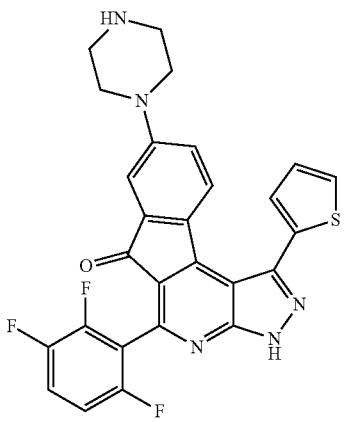 [SMILES: O=C1c2cc(N3CCNCC3)ccc2-c2c1c(-c1c(F)ccc(F)c1F)nc1[nH]nc(-c3cccs3)c21]

03

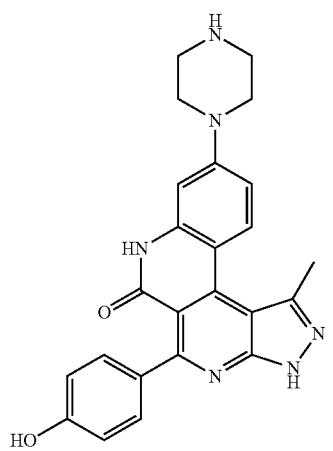 [SMILES: Cc1n[nH]c2nc(-c3ccc(O)cc3)c3c(=O)[nH]c4cc(N5CCNCC5)ccc4c3c12]

04

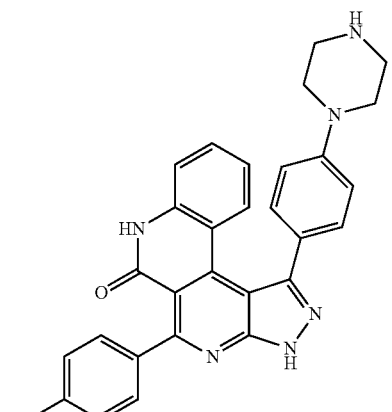

05

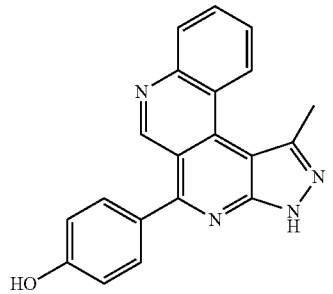

06

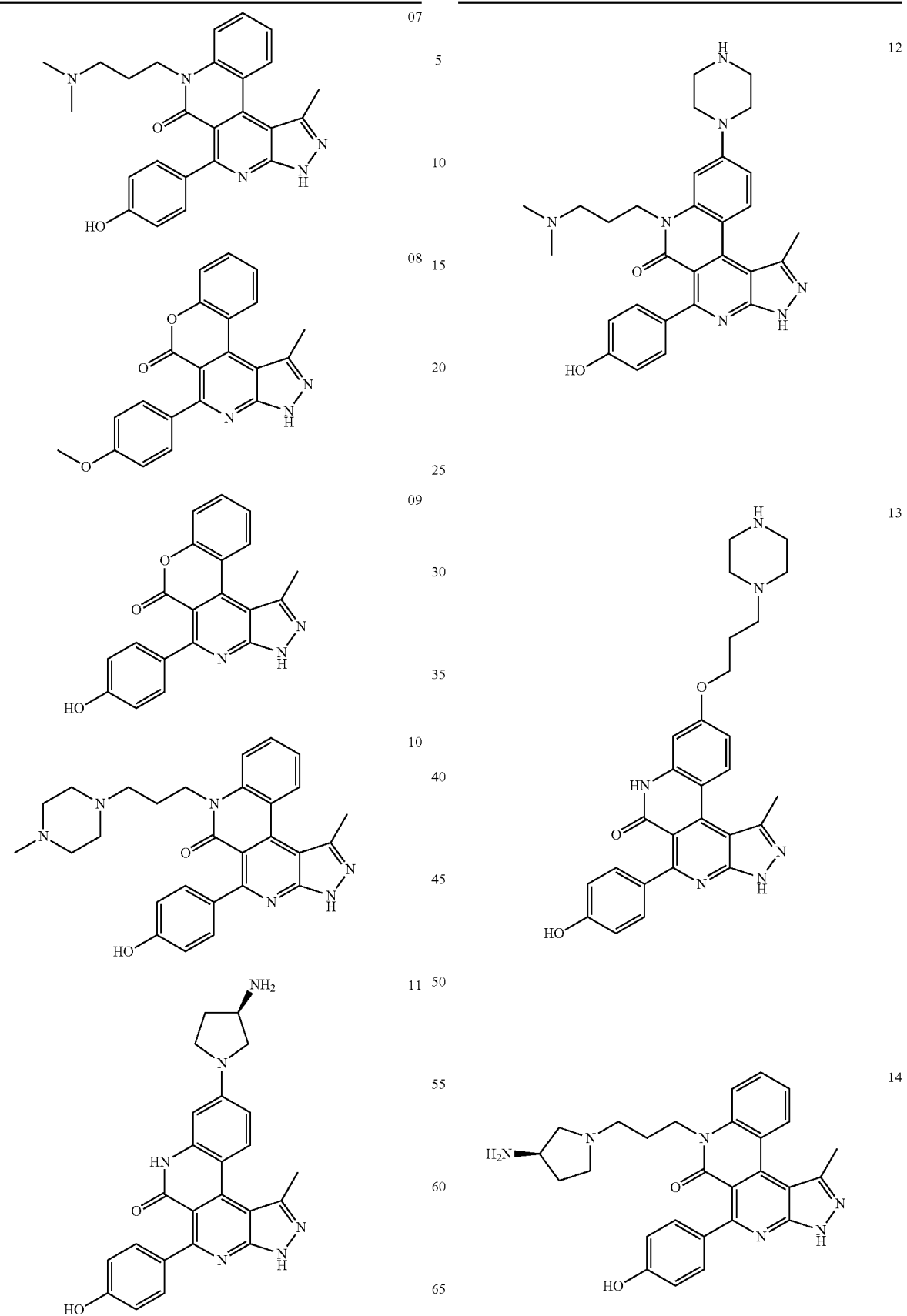

| 13 -continued | 14 -continued |
|---|---|
| 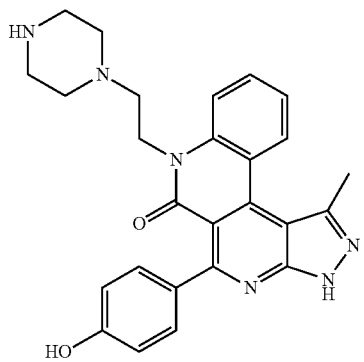 [SMILES: Cc1n[nH]c2nc(-c3ccc(O)cc3)c3c(=O)n(CCN4CCNCC4)c4ccccc4c3c12] 15 | 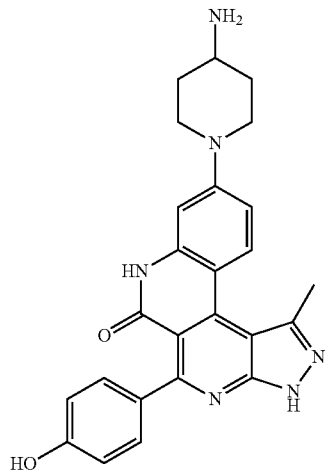 18 |
| 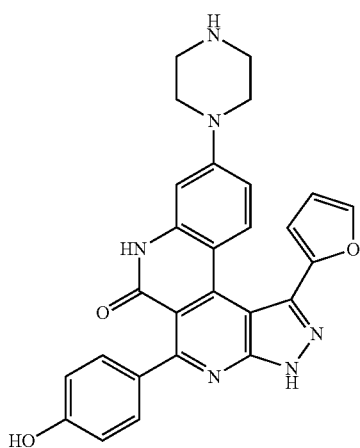 [SMILES: O=c1[nH]c2cc(N3CCNCC3)ccc2c2c1c(-c1ccc(O)cc1)nc1[nH]nc(-c3ccco3)c12] 16 | 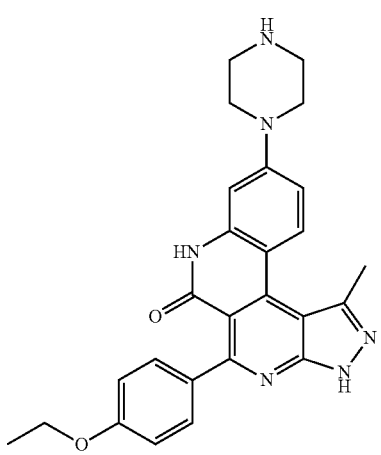 19 |
| 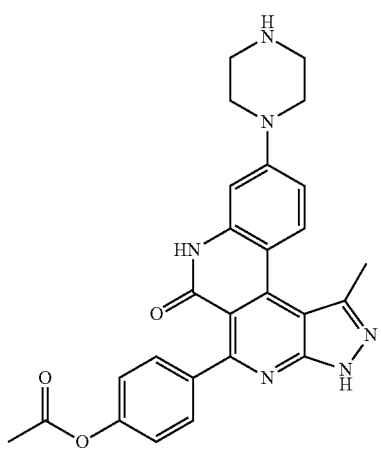 [SMILES: CC(=O)Oc1ccc(-c2nc3[nH]nc(C)c3c3c2c(=O)[nH]c2cc(N4CCNCC4)ccc23)cc1] 17 | 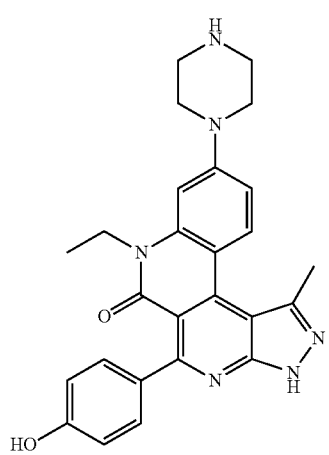 [SMILES: CCn1c(=O)c2c(-c3ccc(O)cc3)nc3[nH]nc(C)c3c2c2ccc(N3CCNCC3)cc21] 20 |

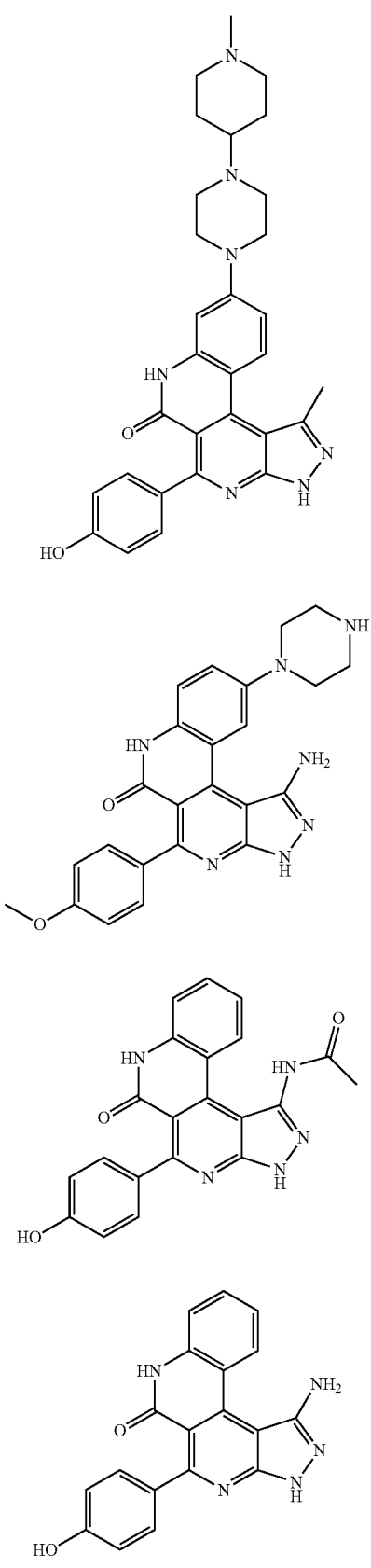
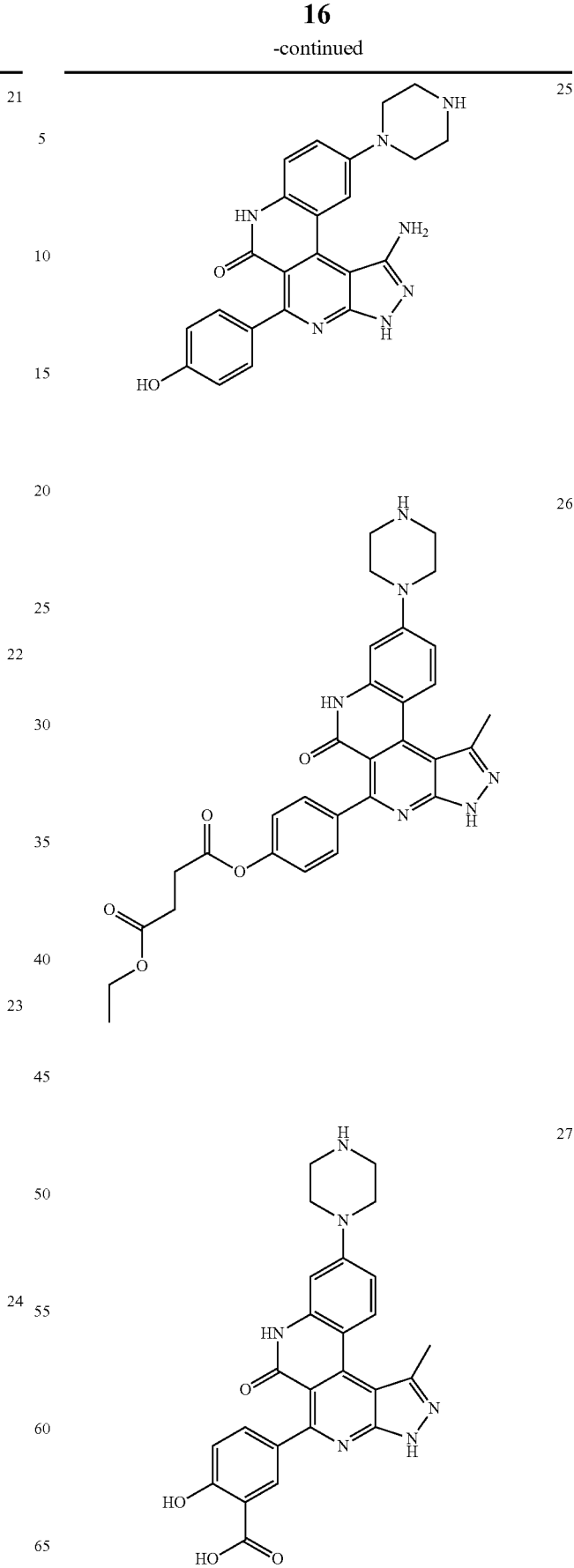

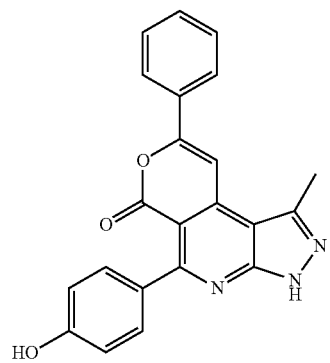 [SMILES: Cc1n[nH]c2nc(-c3ccc(O)cc3)c3c(=O)oc(-c4ccccc4)cc3c12]
28
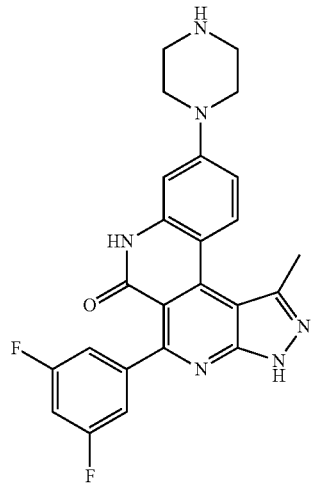
31
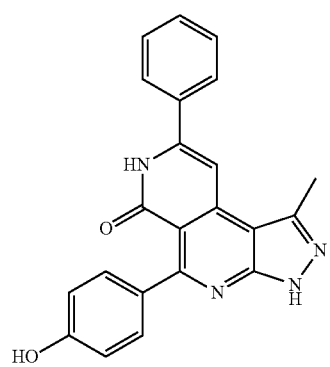 [SMILES: Cc1n[nH]c2nc(-c3ccc(O)cc3)c3c(=O)[nH]c(-c4ccccc4)cc3c12]
29
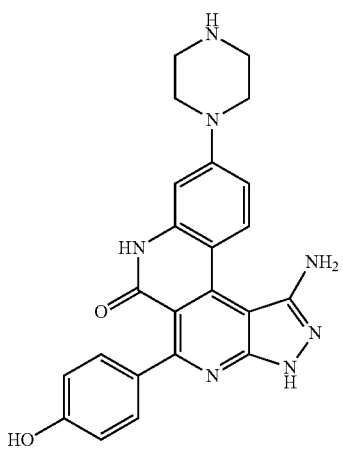
32
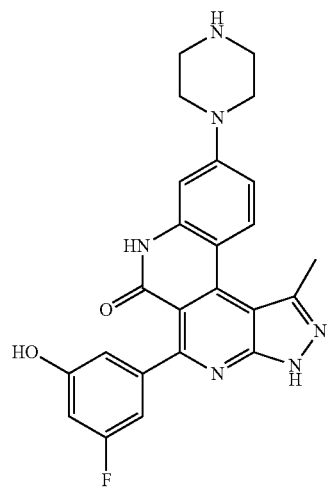 [SMILES: Cc1n[nH]c2nc(-c3cc(O)cc(F)c3)c3c(=O)[nH]c4cc(N5CCNCC5)ccc4c3c12]
30
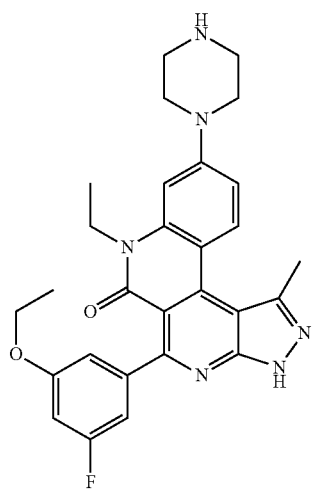 [SMILES: CCOc1cc(F)cc(-c2nc3[nH]nc(C)c3c3c2c(=O)n(CC)c2cc(N4CCNCC4)ccc32)c1]
33

-continued
| | |
|---|---|
| 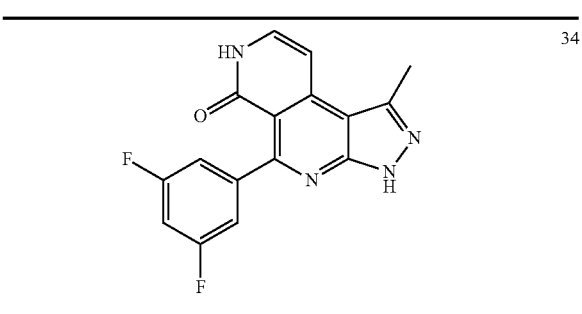 34 | 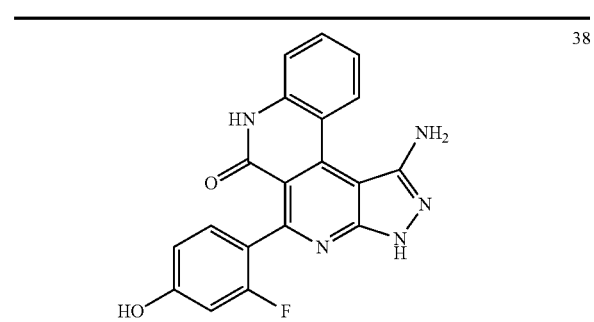 38 |
| 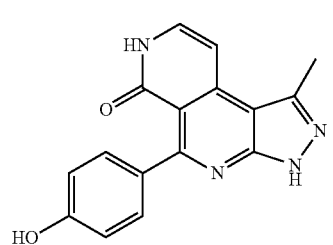 [SMILES: Cc1n[nH]c2nc(-c3ccc(O)cc3)c3c(=O)[nH]ccc3c12] 35 | 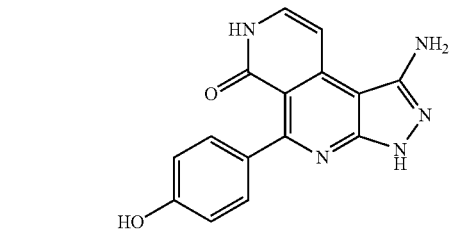 [SMILES: Nc1n[nH]c2nc(-c3ccc(O)cc3)c3c(=O)[nH]ccc3c12] 39 |
| | 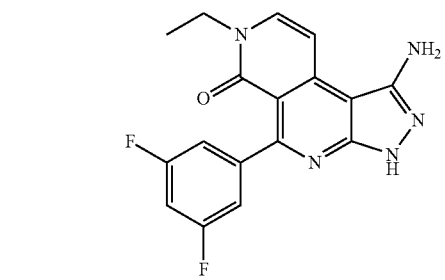 [SMILES: CCn1ccc2c(c(-c3cc(F)cc(F)c3)nc3[nH]nc(N)c32)c1=O] 40 |
| 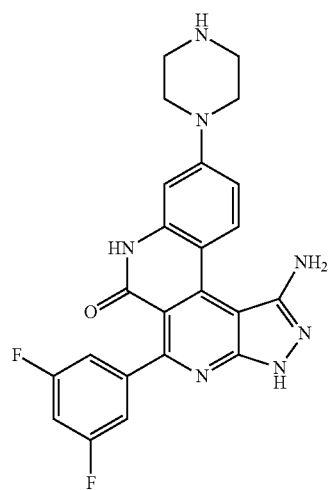 36 | 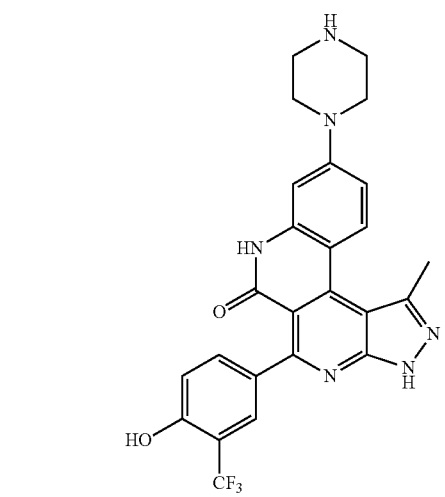 [SMILES: Cc1n[nH]c2nc(-c3ccc(O)c(C(F)(F)F)c3)c3c(=O)[nH]c4cc(N5CCNCC5)ccc4c3c12] 41 |
| 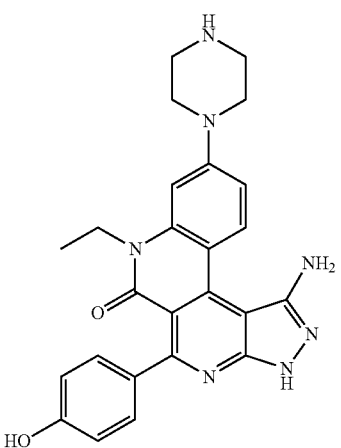 37 | 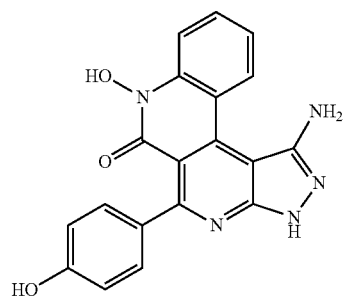 [SMILES: Nc1n[nH]c2nc(-c3ccc(O)cc3)c3c(=O)n(O)c4ccccc4c3c12] 42 |

|    |    |
|---|---|
| 43 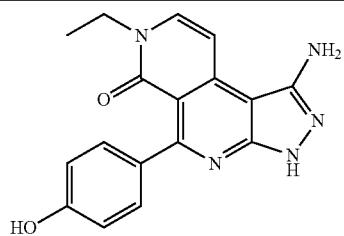 | 47 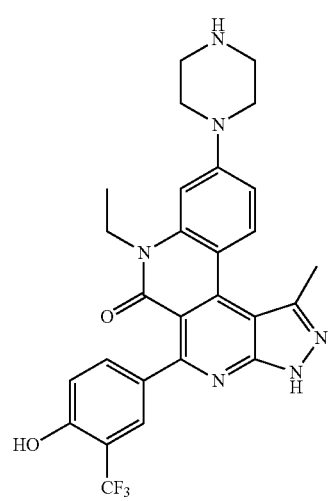 [SMILES: CCn1c(=O)c2c(-c3ccc(O)c(C(F)(F)F)c3)nc3[nH]nc(C)c3c2c2ccc(N3CCNCC3)cc21] |
| 44 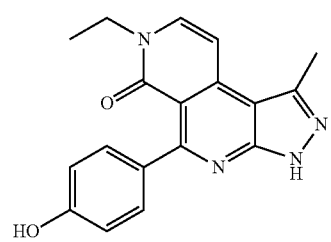 [SMILES: CCn1ccc2c(c(-c3ccc(O)cc3)nc3[nH]nc(C)c32)c1=O] | |
| 45 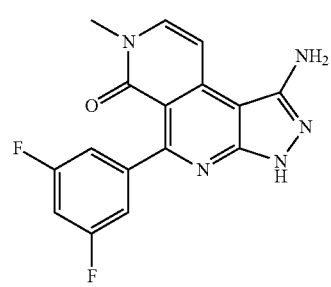 [SMILES: Cn1ccc2c(c(-c3cc(F)cc(F)c3)nc3[nH]nc(N)c32)c1=O] | 48 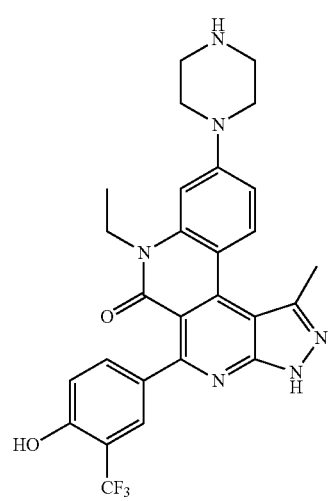 [SMILES: CCn1c(=O)c2c(-c3ccc(O)c(C(F)(F)F)c3)nc3[nH]nc(C)c3c2c2ccc(N3CCNCC3)cc21] |
| 46 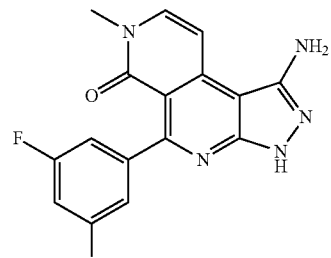 | 49 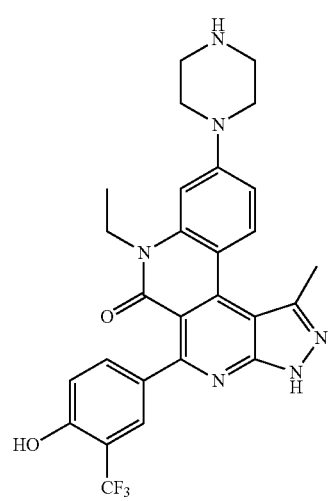 [SMILES: CCn1c(=O)c2c(-c3ccc(O)c(C(F)(F)F)c3)nc3[nH]nc(C)c3c2c2ccc(N3CCNCC3)cc21] |

| 50 | 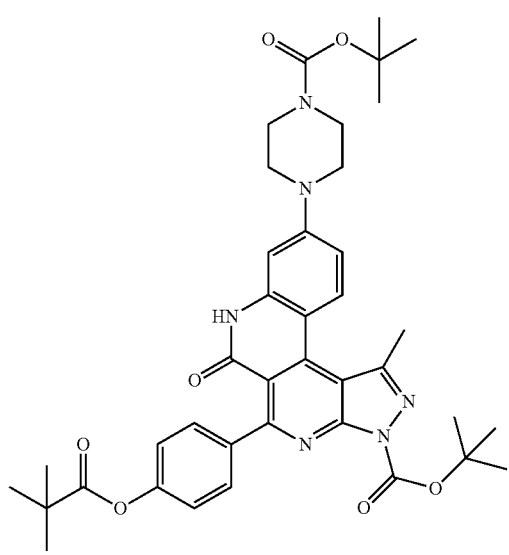 [SMILES: Cc1nn(C(=O)OC(C)(C)C)c2nc(-c3ccc(OC(=O)C(C)(C)C)cc3)c3c(=O)[nH]c4cc(N5CCN(C(=O)OC(C)(C)C)CC5)ccc4c3c12] |
| --- | --- |
| 51 | 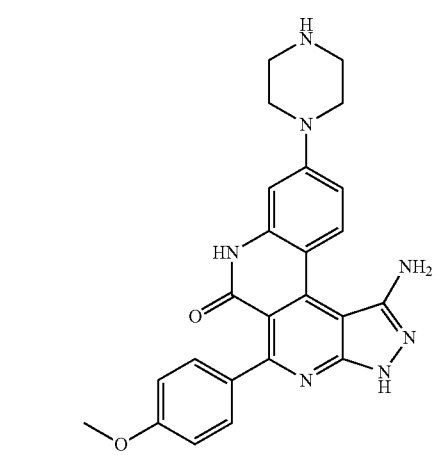 [SMILES: COc1ccc(-c2nc3[nH]nc(N)c3c3c2c(=O)[nH]c2cc(N4CCNCC4)ccc23)cc1] |
| 52 | 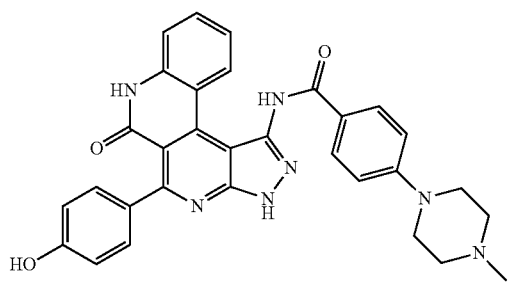 [SMILES: CN1CCN(c2ccc(C(=O)Nc3n[nH]c4nc(-c5ccc(O)cc5)c5c(=O)[nH]c6ccccc6c5c34)cc2)CC1] |
| 53 | 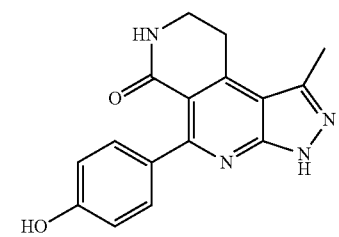 [SMILES: Cc1n[nH]c2nc(-c3ccc(O)cc3)c3c(c12)CCNC3=O] |
| 54 | 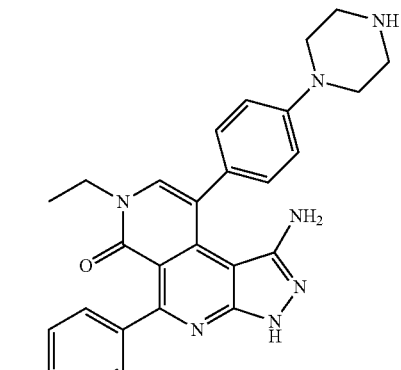 |
| --- | --- |
| 55 | 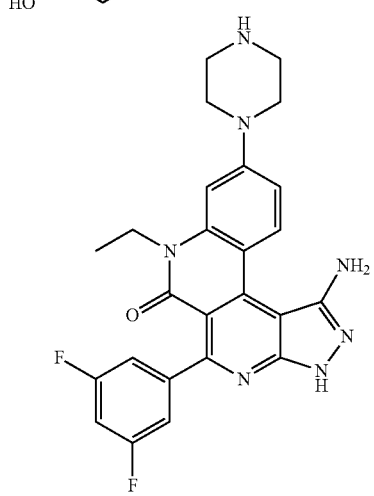 |
| 56 | 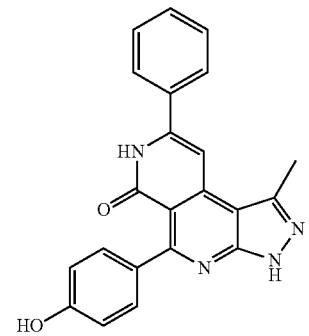 [SMILES: Cc1n[nH]c2nc(-c3ccc(O)cc3)c3c(=O)[nH]c(-c4ccccc4)cc3c12] |
| 57 | 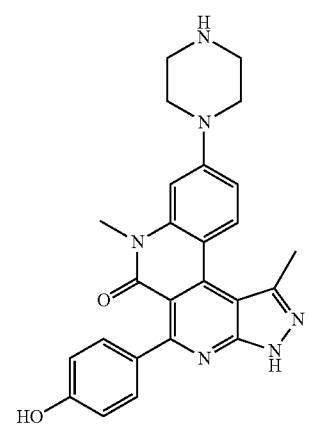 [SMILES: Cc1n[nH]c2nc(-c3ccc(O)cc3)c3c(=O)n(C)c4cc(N5CCNCC5)ccc4c3c12] |

The present invention also has as an object a compound according to the invention of formula (I) such as defined above, for use as a drug, notably intended for the treatment of a cancer, of inflammation and of neurodegenerative diseases such as Alzheimer's disease, in particular cancer.

The present invention also relates to the use of a compound of formula (I) such as defined above, for the manufacture of a drug, notably intended for the treatment of cancer, inflammation and neurodegenerative diseases such as Alzheimer's disease, in particular cancer.

The present invention also relates to a method for the treatment of cancer, inflammation and neurodegenerative diseases such as Alzheimer's disease, in particular cancer, comprising the administration to a person in need thereof of an effective dose of a compound of formula (I) such as defined above.

The present invention also has as an object a compound according to the invention of formula (I) such as defined above, for use as a kinase inhibitor, in particular an ALK inhibitor.

The present invention also has as an object a compound according to the invention of formula (I) such as defined above, for use as a kinase inhibitor drug, in particular an ALK inhibitor drug, more particularly intended for the treatment of a disease associated with one or more kinases, in particular associated with ALK.

The present invention also relates to a pharmaceutical composition comprising at least one compound of formula (I) such as defined above, and a pharmaceutically acceptable excipient.

The pharmaceutical compositions according to the invention may be formulated notably for oral administration or for injection, said compositions being intended for mammals, including humans.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by those persons skilled in the art.

The pharmaceutical compositions according to the invention may further comprise at least one other active ingredient, such as an antineoplastic agent.

The present invention also has as an object a pharmaceutical composition comprising:
(i) at least one compound of formula (I) such as defined above, and
(ii) at least one other active ingredient, such as an antineoplastic agent,
as a combination product for simultaneous, separate or staggered use.

The present invention also relates to a pharmaceutical composition such as defined above for use as a drug, notably intended for the treatment of a cancer.

Finally, the present invention has as an object several methods for preparing compounds of formula (I).

The majority of the methods described below relate to methods for preparing compounds of formula (I) wherein $R_5$=H. However, the compounds for which $R_5$ can be obtained from the compounds in which $R_5$=H by techniques well-known to those persons skilled in the art, by nucleophilic substitution.

A first method for preparing a compound of formula (I) according to the invention wherein $X_2$=C=O and $R_5$=H comprises the following successive steps:
(a1) reaction of a compound of following formula (II):

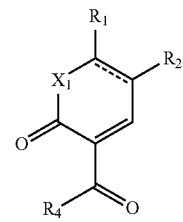

(II)

wherein $R_1$, $R_2$, $R_4$ and $X_1$ are such as defined above, with a compound of following formula (III),

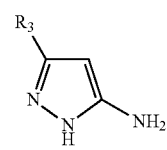

(III)

wherein $R_3$ is such as defined above,
to yield a compound of formula (I) wherein $X_2$=C=O and $R_5$=H,
(b1) optionally salification of the compound of formula (I) obtained in the preceding step (a1) to yield a pharmaceutically acceptable salt of same, and
(c1) separation of the compound of formula (I) obtained in the preceding step (a1) or (b1) from the reaction medium.

Step (a1):
This step corresponds to a cyclization and oxidation reaction between compounds (II) and (III) for forming the pyridine ring of the pyrazolopyridine moiety of the compounds of formula (I).

This reaction can be carried out in the presence of ammonium acetate, with or without solvent, wherein the solvent may be a weak acid such as acetic acid. The reaction can be carried out at a temperature between 20° C. and 200° C.

The starting products of formula (II) and (III) are commercially available or are accessible by synthetic methods well-known to those persons skilled in the art (see in particular the experimental section and *Tetrahedron asymmetry* 2009, 20, 1881; *J. Heterocycl. Chem.* 1989, 26, 1589; *Monatsch. Chem.* 1995, 126, 1341).

This reaction makes it possible to prepare in particular compounds of formula (I) wherein $X_1$=O or $NR_6$.

Step (b1):
This step can be carried out by salification methods well-known to those persons skilled in the art, by the addition of a pharmaceutically acceptable acid or base such as defined above. More particularly, it will be a pharmaceutically acceptable acid addition salt such as HCl, HBr or formic acid.

Step (c1):
The compound of formula (I) obtained can be separated from the reaction medium by methods well-known to those persons skilled in the art, such as, for example, by extraction, evaporation of the solvent or by precipitation and filtration.

Furthermore, the compound can be purified if necessary by techniques well-known to those persons skilled in the art, such as by recrystallization if the compound is crystalline, by distillation, by silica gel column chromatography or by high-performance liquid chromatography (HPLC).

A second method for preparing a compound of formula (I) according to the invention, wherein

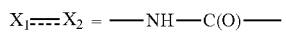

or —O—C(O)— and $R_5$=H, comprises the following successive steps:

(a2) hydrolysis reaction of the CN function into acid (—COOH) or into amide (—CONH$_2$) of a compound of one of the following two formulas (IV) or (IV-a):

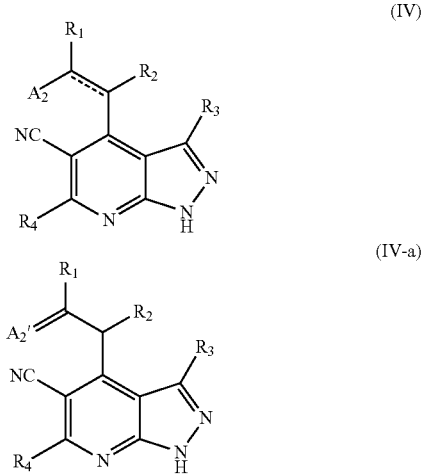

wherein $A_2$ represents a leaving group such as a halogen atom (such as F or Cl) or a tosylate (OTs) or mesylate (OMs) group, $A_2$' represents an oxygen or sulfur atom and $R_1$, $R_2$, $R_3$ and $R_4$ are such as defined above, followed by intramolecular cyclization to yield a compound of formula (I) wherein

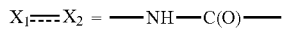

or —O—C(O)— and $R_5$=H, (b2) optionally salification of the compound of formula (I) obtained in the preceding step (a2) to yield a pharmaceutically acceptable salt of same, and (c2) separation of the compound of formula (I) obtained in the preceding step (a2) or (b2) from the reaction medium.

Step (a2):

In the context of the present invention, "leaving group" refers to a chemical group that can be easily displaced by a nucleophile during a nucleophilic substitution reaction, wherein the nucleophile is more particularly an acid or amide functional group. Such a leaving group can thus be more particularly a halogen atom such as a chlorine or fluorine atom, a mesylate (CH$_3$—S(O$_2$)O—), a triflate (CF$_3$—S(O)$_2$O—) or a tosylate (p-Me-C$_6$H$_4$—S(O)$_2$O—).

The hydrolysis reaction will be carried out in the presence of a strong acid such as H$_2$SO$_4$ to hydrolyze the CN functional group into acid (—COOH) and thus to prepare compounds of formula (I) with $X_1$=O. To hydrolyze the CN functional group into amide (—CONH$_2$) and thus to prepare compounds of formulas (I) with $X_1$=NH, the hydrolysis reaction will be carried out in the presence of a strong base such as sodium hydroxide or potassium hydroxide, in particular in the presence of a high boiling-point polar solvent such as ethylene glycol or dimethylsulfoxide.

The cyclization step will be carried out in the presence of a strong base such as sodium hydroxide or potassium hydroxide, in particular in the presence of a high boiling-point polar solvent such as ethylene glycol or dimethylsulfoxide.

Thus, when $X_1$=NH, step (a2) comprising a hydrolysis and cyclization reaction to form the ring fused with the pyrazolopyridine core of the compounds of formula (I) can be carried out in a one-pot fashion, i.e., without isolating the synthesis intermediate, wherein the entire step is carried out in the same reactor. Indeed, the cyclization step takes place spontaneously under the reaction conditions, once the CN functional group is hydrolyzed.

Additional protection/deprotection steps can be carried out if necessary to protect sensitive functional groups under the reaction conditions and/or to promote the hydrolysis reaction, wherein the protected groups are deprotected once the reaction is carried out.

The compounds of formula (IV) and (IV-a) can be prepared by methods well-known to those persons skilled in the art. They can be synthesized notably by a multicomponent reaction (see the experimental section in particular) between a ketone of formula (V), an aldehyde of formula (VI) and an amine of formula (VII) as follows:

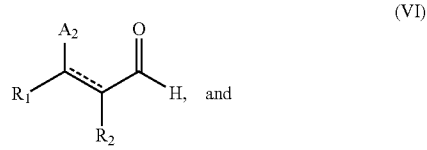

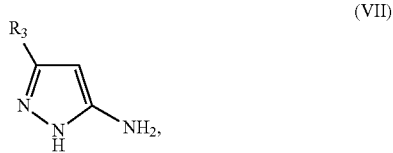

to yield a compound of following formula (VIII):

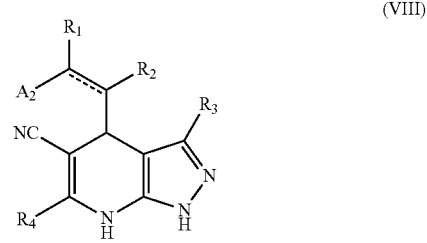

with $A_2$, $R_1$, $R_2$, $R_3$ and $R_4$ such as defined above, followed by an oxidation step, notably in the presence of manganese oxide, to obtain the compound of formula (IV) desired.

Step (b2): see preceding step (b1).
Step (c2): see preceding step (c1).
A third method for preparing a compound of formula (I) according to the invention wherein

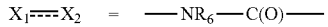

and $R_5$=H comprises the following successive steps:
(a3) deprotection of the protecting or precursor group GP of an amine functional group of a compound of following formula (IX):

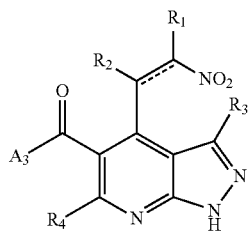

wherein $A_3$ represents a $(C_1-C_6)$alkoxy group, GP represents $NO_2$, NH—CO—$(C_1-C_6)$alkyl, NH—CO-aralkyl, NH—$CO_2$—$(C_1-C_6)$alkyl or NH—$CO_2$aralkyl, and $R_1$, $R_2$, $R_3$ and $R_4$ are such as defined above,
followed by intramolecular cyclization to yield a compound of formula (I) wherein

and $R_5$=H with $R_6$=H or OH,
(b3) optionally substitution of the amide functional group formed in the preceding step (a3) to yield a compound of formula (I) wherein

and $R_5$=H with $R_6 \neq$H and $R_6 \neq$OH,
(c3) optionally salification of the compound of formula (I) obtained in the preceding step to yield a pharmaceutically acceptable salt of same, and
(d3) separation of the compound of formula (I) obtained in the preceding step from the reaction medium.

Step (a3):
When GP=$NO_2$, this step can be carried out in the presence of a reducing agent such as iron or one containing tin (e.g., $SnCl_2$) or zinc, notably in the presence of a solvent such as acetic acid. Once the $NO_2$ functional group is reduced intramolecular cyclization takes place spontaneously under the reaction conditions to yield the compound of formula (I) desired. Using iron as a reducing agent makes it possible to obtain compounds of formula (I) such as defined above with $R_6$=H, whereas reducing agents containing tin such as $SnCl_2$ make it possible to obtain compounds of formula (I) such as defined above with $R_6$=OH.
The reaction can be carried out at a temperature between 20° C. and 200° C.

Alternatively, the $NO_2$ functional group can be hydrogenated into an $NH_2$ functional group in the presence of a catalyst under an atmosphere of hydrogen, to then be cyclized intramolecularly on the —$COA_3$ ester functional group under acid or basic catalysis conditions to yield the compound of formula (I) desired.
When GP=NH—CO—$(C_1-C_6)$alkyl, NH—CO-aralkyl, NH—$CO_2$—$(C_1-C_6)$alkyl or NH—$CO_2$-aralkyl, the deprotection step can be carried out in the presence of a strong acid such as trifluoroacetic acid or hydrochloric acid, notably in the presence of an aprotic solvent such as dichloromethane or 1,4-dioxane. The intramolecular cyclisation step of the amine functional group thus deprotected on the —$COA_3$ functional group can be carried out in the presence of a strong base such as sodium hydride, notably in the presence of an aprotic solvent such as tetrahydrofurane or dimethylformamide.
Additional protection/deprotection steps can be carried out if necessary to protect the sensitive functional groups under the reaction conditions and to deprotect them once the reaction is carried out.
The compounds of formula (IX) can be prepared by adapting the methods described elsewhere (see the experimental section in particular).

Step (b3):
This substitution step of the nitrogen atom of an amide functional group can be carried out by techniques well-known to those persons skilled in the art, such as notably in the presence of a compound of formula $R_6A_4$, wherein $A_4$ represents a leaving group such as a halogen atom or a tosylate or a mesylate, and in the presence of a base such as NaH, from the compound of formula (I) wherein $R_6$=H.
Step (c3): see preceding step (b1).
Step (d3): see preceding step (c1).
A fourth method for preparing a compound of formula (I) according to the invention wherein $R_3$=—$NR_{46}R_{47}$, —$NR_{48}$-aryl, —$NR_{48}$-aralkyl, —$NR_{48}$-heteroaryl, —$NR_{48}$-carbocycle, —$NR_{48}$-heterocycle, —$NR_{48}CO$-aryl, —$NR_{48}CO$—$(C_1-C_6)$alkyl, —$NR_{48}CO$-aralkyl, —$NR_{48}CO$-heteroaryl, —$NR_{48}CO$-carbocycle, —$NR_{48}CO$-heterocycle, —$NR_{48}SO_2$—$(C_1-C_6)$alkyl, —$NR_{48}SO_2$-aryl, —$NR_{48}SO_2$-aralkyl, —$NR_{48}SO_2$-heteroaryl, —$NR_{48}SO_2$-carbocycle, or —$NR_{48}SO_2$-heterocycle, comprises the following successive steps:
(a4) reaction of a compound of following formula (X):

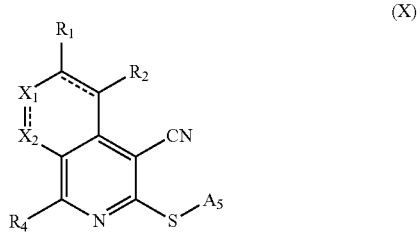

wherein $A_5$ represents a $(C_1-C_6)$alkyl group and $R_1$, $R_2$, $R_4$, $X_1$ and $X_2$ are such as defined above,
with a hydrazine of formula $R_5NH$—$NH_2$, wherein $R_5$ is such as defined above, and in particular with the hydrazine $(NH_2)_2$, to yield a compound of formula (I) wherein $R_3$=$NH_2$,
(b4) optionally substitution of the $NH_2$ functional group of the compound of formula (I) obtained in preceding step (a4) to yield a compound of formula (I) wherein $R_3$=$NR_{46}R_{47}$ with $R_{46}$ and/or $R_{47}$ not representing a hydrogen atom, —NR$_{48}$-aryl, —NR$_{48}$-aralkyl, —NR$_{48}$-heteroaryl, —NR$_{48}$-carbocycle, —NR$_{48}$-heterocycle, —NR$_{48}$CO-aryl, —NR$_{48}$CO—(C$_1$-C$_6$)alkyl, —NR$_{48}$CO-aralkyl, —NR$_{48}$CO-heteroaryl, —NR$_{48}$CO-carbocycle, —NR$_{48}$CO-heterocycle, —NR$_{48}$SO$_2$—(C$_1$-C$_6$)alkyl, —NR$_{48}$SO$_2$-aryl, —NR$_{48}$SO$_2$-aralkyl, —NR$_{48}$SO$_2$-heteroaryl, —NR$_{48}$SO$_2$-carbocycle, or —NR$_{48}$SO$_2$-heterocycle, (c4) optionally salification to yield a pharmaceutically acceptable salt of the compound of formula (I) obtained in the preceding step, and (d4) separation of the compound of formula (I) obtained in the preceding step from the reaction medium.

Step (a4):

This step can be carried out in polar alcohol solvents, and dimethylsulfoxide or dimethylacetamide can be added to improve the solubilization of the various intermediates and/or to increase the boiling point of the solvent mixture.

This step can be carried out in the presence of hydrazine at a temperature between 0° C. and 200° C., notably at the boiling point of the solvent or the solvent mixture.

Additional protection/deprotection steps can be carried out if necessary to protect the sensitive functional groups under the reaction conditions and to deprotect them once the reaction is carried out.

The compounds of formula (X) can be prepared by methods described elsewhere (see the experimental section in particular).

Step (b4):

This substitution step of the NH$_2$ functional group (radical R$_3$) can be carried out by techniques well-known to those persons skilled in the art.

In order to obtain an R$_3$ group =NR$_{46}$R$_{47}$, this step can be carried out notably in the presence of a compound of formula R$_{46}$A$_6$ and/or R$_{47}$A$_7$ wherein A$_6$ and A$_7$ represent, independently of one another, a leaving group such as a halogen atom or a tosylate or a mesylate, and in the presence of a base such as NaH.

Furthermore, when R$_3$ represents an NHCO-aryl, NHCO—(C$_1$-C$_6$)alkyl, NHCO-aralkyl, NHCO-heteroaryl, NHCO-carbocycle or NHCO-heterocycle group, it can be envisaged to carry out a coupling between the NH$_2$ functional group (radical R$_3$) and a suitable carboxylic acid. The conditions for carrying out such a coupling are well-known to those persons skilled in the art. An additional substitution with notably a compound of formula R$_{48}$A$_{48}$, wherein A$_{48}$ represents a leaving group such as a halogen atom or a tosylate or a mesylate, and in the presence of a base such as NaH, makes it possible to obtain R$_3$ groups representing —NR$_{48}$-aryl, —NR$_{48}$-aralkyl, —NR$_{48}$-heteroaryl, —NR$_{48}$-carbocycle, —NR$_{48}$-heterocycle, —NR$_{48}$CO-aryl, —NR$_{48}$CO—(C$_1$-C$_6$)alkyl, —NR$_{48}$CO-aralkyl, —NR$_{48}$CO-heteroaryl, —NR$_{48}$CO-carbocycle, or —NR$_{48}$CO-heterocycle, with R$_{48}$≠H.

The compounds wherein R$_3$=—NR$_{48}$SO$_2$—(C$_1$-C$_6$)alkyl, —NR$_{48}$SO$_2$-aryl, —NR$_{48}$SO$_2$-aralkyl, —NR$_{48}$SO$_2$-heteroaryl, —NR$_{48}$SO$_2$-carbocycle, or —NR$_{48}$SO$_2$-heterocycle can be obtained in a similar manner with a sulfonic acid in the place of the carboxylic acid.

Step (c4): see preceding step (b1).

Step (d4): see preceding step (c1).

A fifth method for preparing a compound of formula (I) according to the invention, wherein R$_5$=H, $X_1\text{=}X_2$ represents a —C(=O)— group and $\text{---}$ represents a double bond between the carbon atoms carrying the radicals R$_1$ and R$_2$, comprises the following successive steps:

(a5) intramolecular cyclization under acid conditions of a compound of following formula (XI):

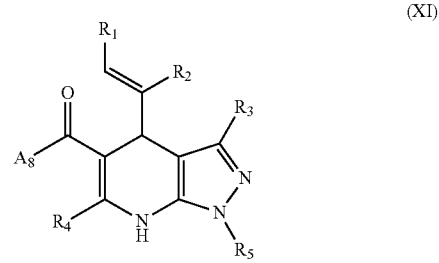

(XI)

wherein A$_8$ represents a (C$_1$-C$_6$)alkoxy group and R$_1$, R$_2$, R$_3$ and R$_4$ are such as defined above, to yield a compound of formula (I) wherein R$_5$=H, $X_1\text{=}X_2$ represents a —C(=O)— group and $\text{---}$ represents a double bond between the carbon atoms carrying the radicals R$_1$ and R$_2$, (b5) optionally salification to yield a pharmaceutically acceptable salt of the compound of formula (I) obtained in the preceding step, and (c5) separation of the compound of formula (I) obtained in the preceding step from the reaction medium.

Step (a5):

This step can be carried out in the presence of Brönsted acids (such as polyphosphoric acid) or Lewis acids (such as BBr$_3$).

The reaction can be carried out at a temperature between 0° C. and 200° C., in particular at the boiling point of the solvent.

This reaction can be carried out more particularly on compounds of formula (XI) wherein R$_1$ and R$_2$ together form, with the carbon atoms which carry them, an aryl or heteroaryl ring, in particular an aryl ring, optionally substituted as indicated above (in the definition of R$_1$ and R$_2$).

Additional protection/deprotection steps can be carried out if necessary to protect the sensitive functional groups under the reaction conditions and to deprotect them once the reaction is carried out.

The compounds of formula (XI) can be prepared by methods well-known to those persons skilled in the art (see experimental section in particular).

Step (b5): see preceding step (b1).

Step (c5): see preceding step (c1).

It should be noted that the compounds (I) wherein X$_1$=S can be obtained from compounds (I) wherein X$_1$=O, by reaction with Lawesson's reagent (*Tetrahedron* 1991, 47, 10119).

The compounds (I) wherein

can give access to compounds (I) wherein

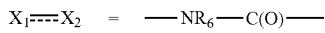

or —N═C(OR$_7$)— (with R$_6$ and R$_7$≠H) by a substitution reaction in the presence of a reagent of formula R$_6$A$_9$ or R$_7$A$_9$, wherein A$_9$ represents a halogen atom, and in the presence of a strong base such as NaH.

The compounds (I) wherein

can give access to compounds (I) wherein

with R═OR$_7$, NR$_8$R$_9$ or SR$_{10}$:
  by chlorination of the amide functional group, in particular in the presence of POCl$_3$, to yield compounds (I) wherein

then
  by nucleophilic substitution of the chlorine atom with a reagent of formula RA$_{10}$ with A$_{10}$ representing notably a halogen atom, optionally in the presence of a base.

The compounds (I) wherein

can also give access to compounds (I) wherein

by reduction of the amide functional group into amine in the presence of a reducer such as lithium aluminum hydride, optionally in the presence of AlCl$_3$ or borohydride, followed by an aromatization step in the presence of an oxidizer such as ceric ammonium nitrate (CAN), 2,3-dichloro-5,6-dicyano-1,4-benzoquinone (DDQ) or oxygen from air, or by heating under acidic conditions.

The present invention will be better understood in view of the following examples which are used only to illustrate the invention and not to limit it in any way.

EXAMPLES

I. Synthesis of the Compounds of the Invention

Depending on the substituents, the polycyclic compounds of the invention can be obtained by various chemical pathways which are distinguished in the general case by the location and nature of the last ring formed. Thus, four principal synthesis pathways were studied wherein the last ring formed is, respectively:

Pathway A: a pyridone or pyranone ring A
Pathway B: a pyridine ring B
Pathway C: a pyrazole ring C
Pathway D: a cyclopentadienone ring A The synthesis pathways indicated below relate to compounds according to the invention with R$_5$═H, the compounds thus obtained being able to easily give access to compounds with R$_5$≠H by nucleophilic substitution.

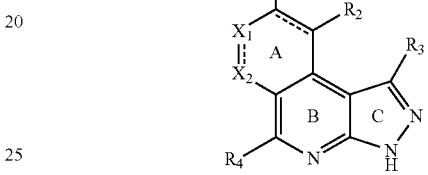

Synthesis Pathway A

The compounds of the invention I can be obtained according to the following diagram, with the key step being an intramolecular cyclization reaction of a 4-(2-fluorophenyl)-1H-pyrazolo[3,4-b]pyridine-5-carbonitrile compound III correctly substituted via the formation of an intermediate carboxamide IV.

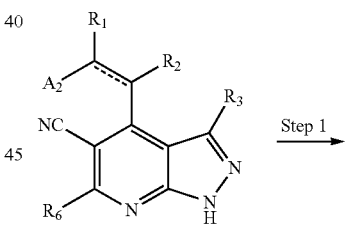

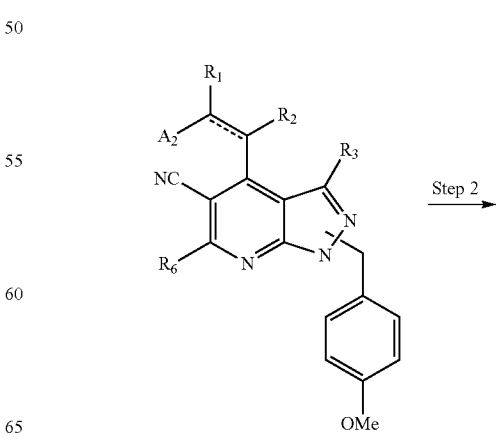

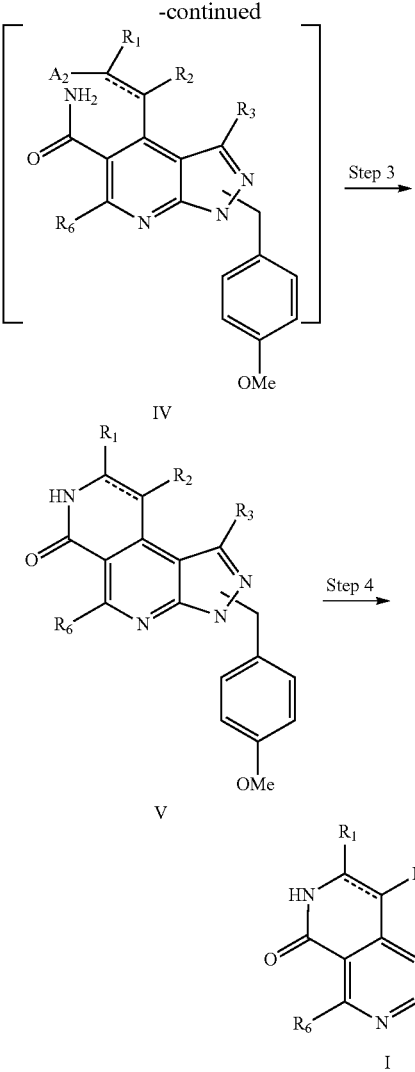

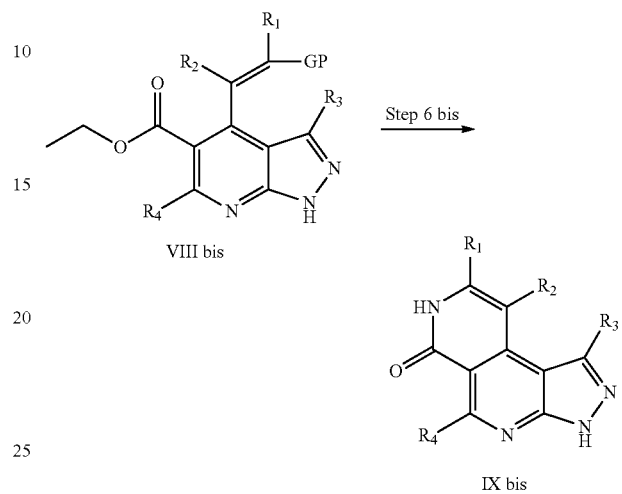

Synthesis Pathway A-bis

The products of the invention I can also be obtained according to the following diagram, with the key step being an intramolecular cyclization reaction between an ester and an amine obtained by deprotection of the GP group of compound VIIIbis, with GP representing an NO$_2$ or an NHP functional group of amide or carbamate type.

Step 6 bis corresponds to the deprotection of the amine on compound VIIIbis in the presence of a strong acid such as trifluoroacetic acid, in the presence of an aprotic solvent such as dichloromethane, at a temperature comprised between 0° C. and the boiling point of the solvent, followed by an intramolecular cyclization of the amine functional group thus deprotected on the —COA$_3$ functional group in the presence of a strong base such as sodium hydride in an aprotic solvent such as tetrahydrofurane or dimethylformamide at temperatures comprised between 0° C. and the boiling point of the solvent.

Synthesis Pathway B

Alternatively, the products of the invention I can be obtained according to the following diagram, with the key step being a cyclization reaction between a 3-ketopyranone or 3-ketopyridone intermediate VI and an aminopyrazole VII.

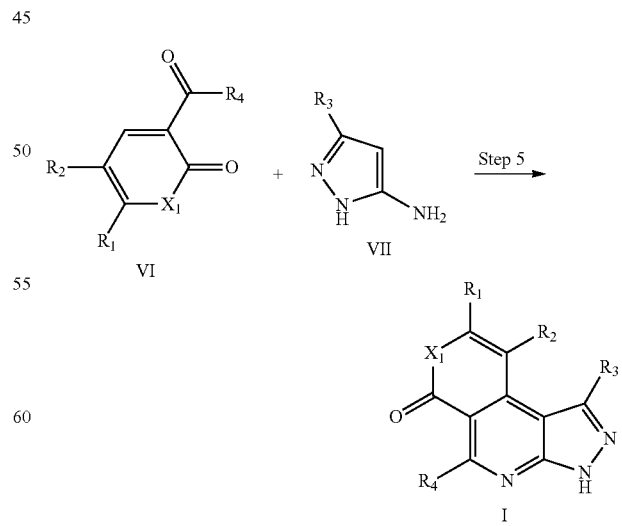

Step 1 corresponds to a protection step of the pyrazole of compounds II by a para-methoxybenzyl group in the presence of a base such as potassium carbonate. The reaction is carried out in rather polar solvents (acetone, dimethylformamide, etc.) notably at a temperature between 0° C. and the boiling point of the solvent.

Step 2 corresponds to partial hydrolysis of the nitrile group of compound III in the presence of a strong base (sodium hydroxide, potassium hydroxide, etc.) in a high boiling-point polar solvent (ethylene glycol, dimethylsulfoxide) in the presence of water at temperatures between 20° C. and the boiling point of the solvents.

Step 3 corresponds to nucleophilic substitution intramolecular cyclization of compound IV between a carboxamide and a phenyl substituted in an adequate position by a leaving group (fluorine, tosyl, etc.) in the presence of a strong base (sodium hydroxide, potassium hydroxide, etc.) in a high boiling-point polar solvent (ethylene glycol, dimethylsulfoxide).

Step 4 corresponds to deprotection of the para-methoxybenzyl group of compound V in strong acids (trifluoroacetic acid, hydrobromic acid dissolved in acetic acid, sulfuric acid) at temperatures between 20° C. and the boiling point of the solvent.

Step 5 corresponds to a cyclization and oxidation condensation between the intermediate of formula VI (accessible by well-known methods) with the aminopyrazole VII. The reaction is carried out in the presence of ammonium acetate, in weak acids, namely acetic acid, or without solvent at temperatures between 20° C. and 200° C. or at the boiling point of the solvent.

Synthesis Pathway C

Alternatively, the products of the invention I can be obtained according to the following diagram, with the key steps being intramolecular cyclization between an ester and an amine obtained by reduction of the $NO_2$ functional group of compound VIII followed by cyclization condensation with hydrazine on intermediate IX.

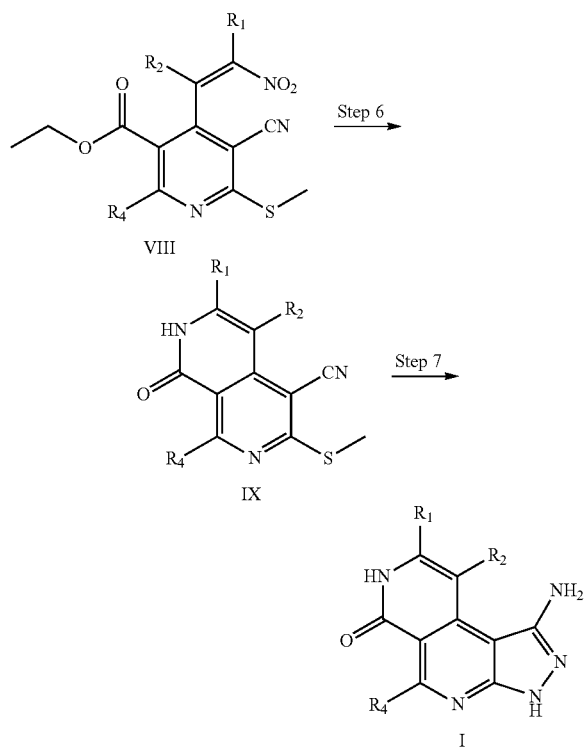

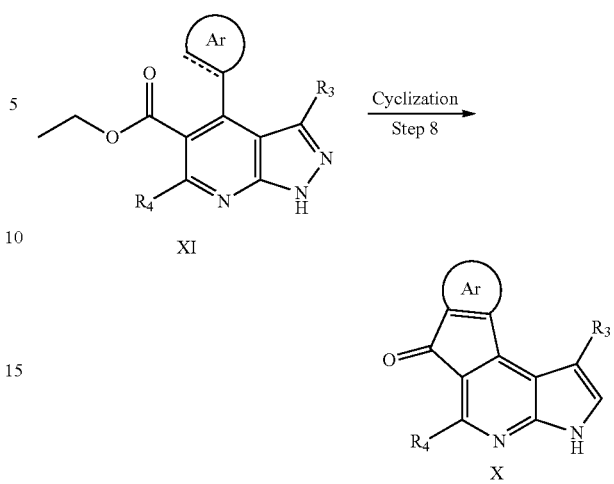

Step 8 corresponds to intramolecular cyclization with cyclopentadienone ring formation. The reaction takes place in solvents of any type in the presence of Brönsted or Lewis acids at temperatures between 0° C. and the boiling point of the reaction medium.

A) Synthesis of Reaction Intermediates

A-1 Synthesis of β-Ketonitriles and β-Ketoesters

The starting activated methylene compounds of formula (A) are well-known products and can be prepared by various methods described in the literature.

Procedure A1a: Standard Synthesis of β-Ketonitriles

Thus, the cyanomethyl derivatives used as starting products for preparing pyrazolopyridines can be prepared by the method described in the literature (*Synthesis* 2008, 7, 1094; *J. Med. Chem.* 2003, 46, 794; *Tetrahedron Lett.* 1983, 24, 5023, whose teachings are incorporated by reference in the present application), by reacting an ester and a ketonitrile in the presence of an alkyllithium or alkylpotassium organometallic derivative, in an organic solvent such as tetrahydrofuran, at low temperature.

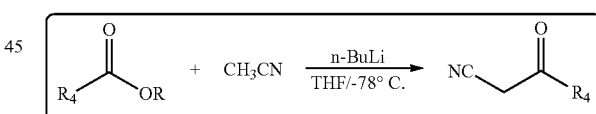

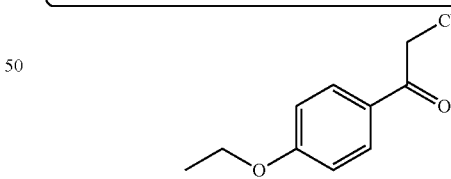

3-(4-ethoxyphenyl)-3-oxopropanenitrile

Step 6 corresponds to a reduction of the nitro group of derivative VIII followed by intramolecular cyclization in the presence of a reducer such as iron, zinc or tin, in a solvent (acetic acid), at temperatures between 20° C. and the boiling point of the solvents. Alternatively, this step can be carried out sequentially with a first catalytic hydrogenation step followed by a second cyclization step under acid or basic catalysis conditions.

Step 7 corresponds to nucleophilic substitution of the hydrazine on compound IX followed by intramolecular cyclization. The reaction takes place in polar solvents (alcohols in particular) at temperatures between 0° C. and the boiling point of the solvent. A dimethylsulfoxide or dimethylacetamide co-solvent can be added in order to improve the reaction conditions.

Alternatively, steps 6 and 7 can be reversed.

Synthesis Pathway D

Alternatively, the products of the invention X can be obtained according to the following diagram by an intramolecular cyclization reaction of compound XI.

27.1 ml (67.8 mmol) of a 2.5 M solution of n-butyllithium in hexane is added drop by drop at −78° C. under argon to a solution of 4.4 g (108.6 mmol) of acetonitrile in 50 ml of anhydrous tetrahydrofuran. The reaction mixture is stirred for 30 min at −78° C., then a solution of 5.2 g (27.15 mmol) of ethyl 4-ethoxybenzoate diluted in 30 ml of tetrahydrofuran is added at −78° C. drop by drop to the reaction mixture. The reaction mixture is stirred for 2 h at −78° C., then 1 M hydrochloric acid solution is added, and the product is extracted several times with ethyl acetate. The organic phases are combined, dried on magnesium sulfate and concentrated. The solid is triturated in 15 ml of methanol to yield 4.4 g (80%) of 4-ethoxyphenyl-3-oxopropanenitrile in the form of a white solid.

LCMS (ESI, m/z): (M+1) 212.18

$^1$H NMR: $\delta_H$ pm 400 MHz, CDCl$_3$: 7.91 (2H, d, CH$_{arom}$), 7.08 (2H, d, CH$_{arom}$), 4.68 (2H, s, CH$_2$), 4.17 (2H, q, CH$_2$), 1.35 (3H, t, CH$_3$).

The compounds below are obtained according to procedure A1a

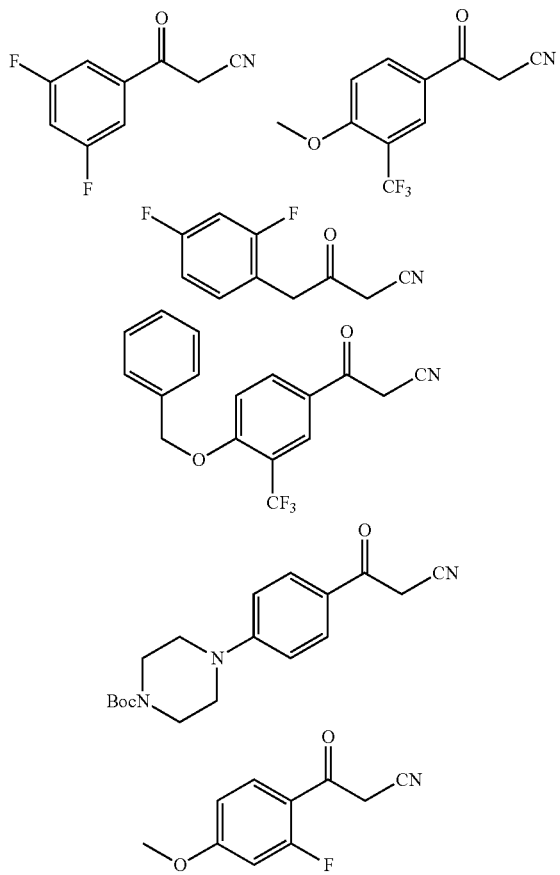

Procedure A1b: Standard Synthesis of β-Ketoesters

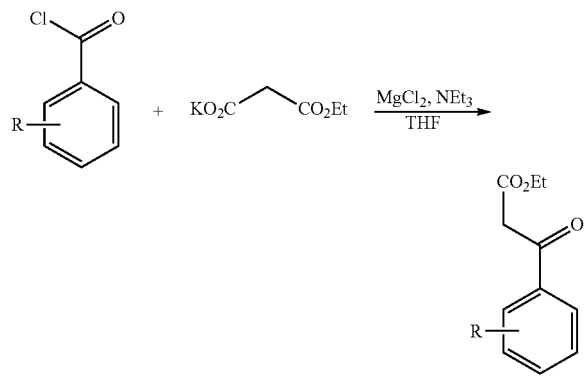

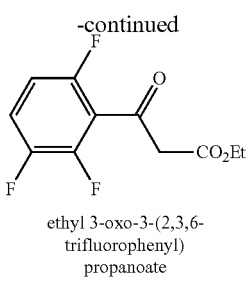

ethyl 3-oxo-3-(2,3,6-trifluorophenyl)propanoate 7.16 ml (51.4 mmol) of triethylamine and 6.12 g (64.25 mmol) of magnesium chloride (II) are added at 0° C. under argon to a solution of 8.75 g (51.4 mmol) of potassium 3-ethoxy-3-oxopropanoate in suspension in 70 ml of anhydrous acetonitrile. The reaction mixture is stirred for 5 hours at room temperature. A solution of 5 g (25.7 mmol) of 2,3,6-trifluorobenzoyle chloride and 3.94 ml (28.3 mmol) of triethylamine is added at 0° C. The reaction mixture is stirred for 18 hours at room temperature and then 1 M hydrochloric acid solution is added until complete solubilization occurs. The product is extracted several times with ethyl acetate. The organic phases are combined, dried on magnesium sulfate and concentrated. The residue is purified by silica gel chromatography (eluent: 92:8 cyclohexane/ethyl acetate) to yield 5.6 g (88%) of ethyl 3-(2,3,6-trifluoro)-3-oxopropanoate (in two mesomeric forms) in the form of a yellow solid.

$^1$H NMR (of the majority form): $\delta_H$ pm 400 MHz, CDCl$_3$: 7.23-7.34 (1H, m, CH$_{arom}$), 6.86-6.98 (1H, m, CH$_{arom}$), 4.19 (2H, q, CH$_2$), 3.91 (2H, s, CH$_2$), 1.24 (3H, t, CH$_3$).

A-2 Standard Synthesis of Aldehydes

The starting aldehydes of formula (B) are well-known products which can be prepared by various methods of the literature. The original aldehydes as well as the methods for obtaining same are described below.

Procedure A2a:

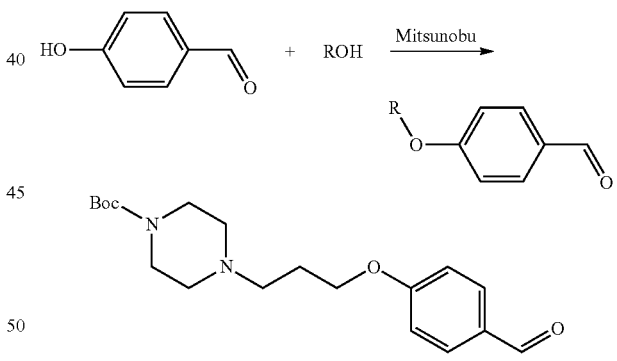

tert-butyl 4-(3-(4-formylphenoxy)propyl)piperazine-1-carboxylate 0.61 ml (3.07 mmol) of diisopropyl diazene-1,2-dicarboxylate is added drop by drop at 0° C. under argon to 0.5 g (2.05 mmol) of tert-butyl 4-(3-hydroxypropyl)piperazine-1-carboxylate, 0.3 g (2.46 mmol) of 4-hydroxybenzaldehyde and 1 g (3.07 mmol) of supported triphenylphosphine (3 mmol/g of resin) diluted in 14.5 ml of anhydrous tetrahydrofuran. The reaction mixture is stirred at room temperature for 20 hours, and then the solid is filtered and rinsed with dichloromethane. The filtrate is concentrated and diluted in sodium hydroxide solution (1 M), the product is extracted several times with ethyl acetate, and then the organic phases are combined, dried on magnesium sulfate and concentrated. The residue is purified by silica gel chromatography (eluent: 4:6 cyclohexane/ethyl acetate to 100% ethyl acetate) to yield 0.58 g of tert-butyl 4-(3-(4-formylphenoxy)propyl)piperazine-1-carboxylate in the form of a colorless oil.

LCMS (ESI, m/z): (M+1) 348.9

$^1$H NMR: $\delta_H$ pm 400 MHz, DMSO: 9.87 (1H, s, CHO), 7.86 (2H, d, CH$_{arom}$), 7.12 (2H, d, CH$_{arom}$), 4.13 (2H, t, CH$_2$), 3.28-3.31 (4H, m, 2CH$_2$), 2.44 (2H, t, CH$_2$), 2.31-2.34 (4H, m, 2CH$_2$), 1.91 (2H, q, CH$_2$), 1.40 (9H, s, 3CH$_3$).

Procedure A2b:

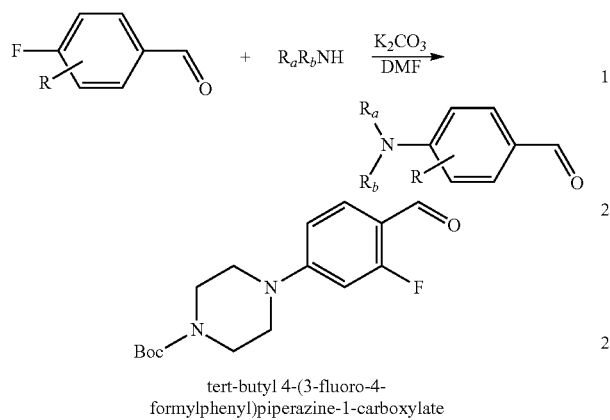

tert-butyl 4-(3-fluoro-4-formylphenyl)piperazine-1-carboxylate 9.17 g (49.3 mmol) of tert-butyl piperazine-1-carboxylate and then 6.81 g (49.3 mmol) of potassium carbonate, respectively, are added to 7 g (49.3 mmol) of 2,4-difluorobenzaldehyde diluted in 60 ml of dimethylsulfoxide. The solution is carried at 60° C. for 8 hours and then water is added and the product is extracted several times with ethyl acetate. The organic phases are combined, dried on magnesium sulfate and concentrated. The residue obtained is purified by silica gel chromatography (eluent: 7:3 cyclohexane/ethyl acetate) to yield 7.4 g (48%) of tert-butyl 4-(3-fluoro-4-formylphenyl)piperazine-1-carboxylate in the form of a white solid.

LCMS (ESI, m/z): (M+1) 309.3

$^1$H NMR: $\delta_H$ pm 400 MHz, DMSO: 9.93 (1H, s, CHO), 7.57-7.68 (1H, m, CH$_{arom}$), 6.72-6.91 (2H, m, CH$_{arom}$), 3.40-3.49 (8H, m, 4CH$_2$), 1.42 (9H, s, 3CH$_3$).

The compounds below are obtained according to procedure A2b

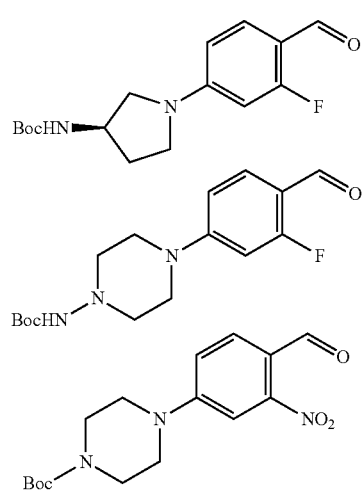

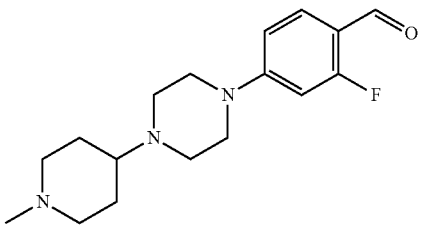

Procedure A2c:

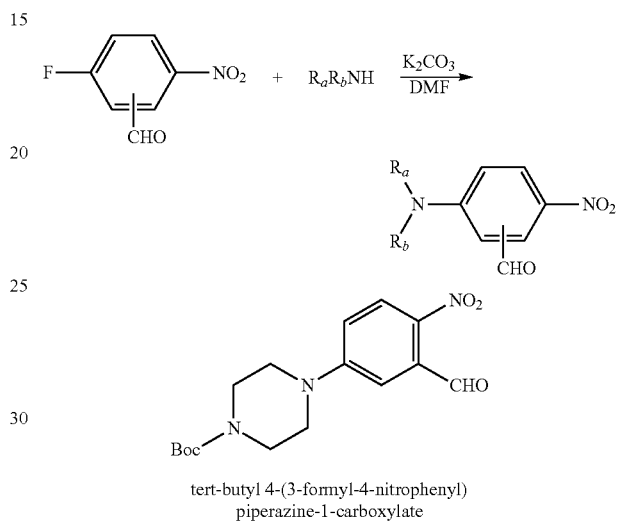

tert-butyl 4-(3-formyl-4-nitrophenyl)piperazine-1-carboxylate 15 ml of dimethylsulfoxide, 4.2 g (30.4 mmol) of potassium carbonate and 5.66 g (30.4 mmol) of tert-butyl piperazine-1-carboxylate, respectively, are added to 5 g (29.6 mmol) of 5-fluoro-2-nitrobenzaldehyde. The solution is carried at 90° C. under stirring for 8 h. After cooling, the reaction mixture is poured over crushed ice. The yellow precipitate formed is filtered, rinsed with water, and then dried to yield 8.6 g (88%) of tert-butyl 4-(3-formyl-4-nitrophenyl)piperazine-1-carboxylate in the form of a yellow solid.

LCMS (ESI, m/z): (M+1) 336.36

$^1$H NMR: $\delta_H$ pm 400 MHz, DMSO: 10.33 (1H, s, CHO), 8.10 (1H, d, CH$_{arom}$), 7.19 (1H, dd, CH$_{arom}$), 7.04 (1H, dd, CH$_{arom}$), 3.48-3.54 (8H, m, 4CH$_2$), 1.42 (9H, s, 3CH$_3$).

A-3 Synthesis of Aminopyrazoles

The aminopyrazoles of formula (C) are well-known products which can be prepared by various methods described in the literature. The aminopyrazoles and the methods for obtaining same used in the present invention appear below.

Procedure A3a:

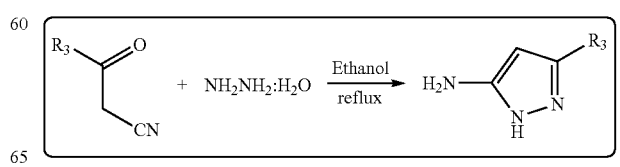

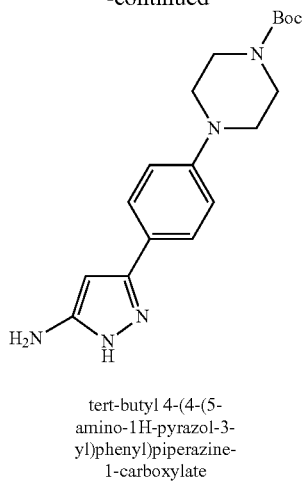

tert-butyl 4-(4-(5-
amino-1H-pyrazol-3-
yl)phenyl)piperazine-
1-carboxylate 2.36 ml (29 mmol) of hydrazine hydrate is added to a solution of 1.6 g (4.86 mmol) of tert-butyl 4-(4-(2-cyanoacetyl)phenyl)piperazine-1-carboxylate dissolved in 30 ml of ethanol. The reaction medium is carried at reflux for 12 hours and then concentrated to a third of its volume. The solid is then triturated, filtered and dried to yield 1.35 g (80%) of tert-butyl 4-(4-(5-amino-1H-pyrazol-3-yl)phenyl)piperazine-1-carboxylate in the form of a beige solid.

LCMS (ESI, m/z): (M+1) 344.2

$^1$H NMR: $\delta_H$ pm 400 MHz, DMSO: 7.49 (2H, d, $CH_{arom}$), 6.95 (2H, d, $CH_{arom}$), 4.64 (2H, m, $NH_2$), 3.40-3.55 (4H, m, $2CH_2$), 3.04-3.22 (4H, m, $2CH_2$), 1.42 (9H, s, $3CH_3$).

Procedure A3b:

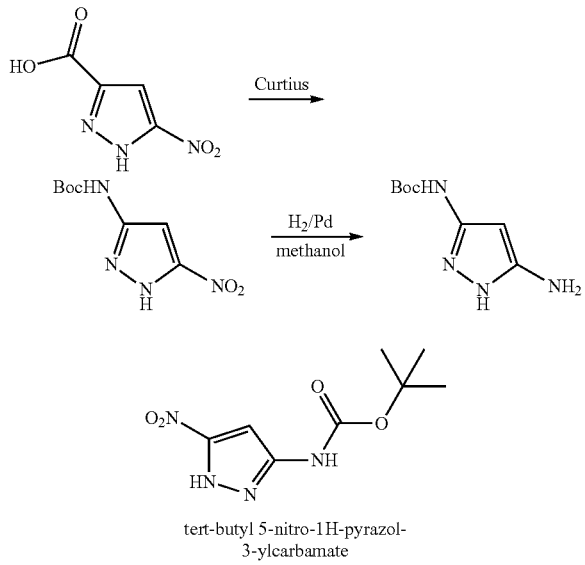

tert-butyl 5-nitro-1H-pyrazol-
3-ylcarbamate 39 ml of tert-butanol, 27.44 ml (127.3 mmol) of diphenyl phosphorazidate and 17.7 ml (127.32 mmol) of triethylamine are added respectively to 10 g (63.66 mmol) of 5-nitro-1H-pyrazol-3-carboxylic acid. The solution is carried at reflux for 8 hours and then saturated aqueous potassium carbonate solution is added until pH=8 and the product is extracted several times with ethyl acetate. The organic phases are combined, dried on magnesium sulfate and concentrated. The residue obtained is triturated in methanol to yield 4.38 g (30.1%) of tert-butyl 5-nitro-1H-pyrazol-3-ylcarbamate in the form of a yellow solid. The filtrate is concentrated and purified by silica gel chromatography (eluent: 7:3 cyclohexane/ethyl acetate) to yield an additional 1.49 g (10.3%) of the desired product.

LCMS (ESI, m/z): (M−1) 227.2

$^1$H NMR: $\delta_H$ pm 400 MHz, DMSO: 13.47 (1H, bs, NH), 10.35 (1H, bs, NH), 6.46 (1H, s, $CH_{arom}$), 1.49 (9H, s, $3CH_3$).

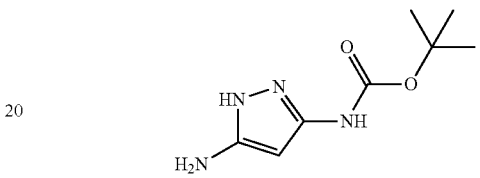

tert-butyl 5-amino-1H-pyrazol-3-ylcarbamate 600 mg (10%) palladium on carbon is added under inert atmosphere to 5.88 g (25.77 mmol) of tert-butyl 5-nitro-1H-pyrazol-3-ylcarbamate diluted in 145 ml of methanol and then the reaction mixture is stirred under hydrogen atmosphere for 24 hours. The solution is filtered on Celite and then rinsed with ethyl acetate. The filtrate is concentrated to yield 4.93 g (96%) of tert-butyl 5-amino-1H-pyrazol-3-ylcarbamate in the form of a gray solid.

LCMS (ESI, m/z): (M+1) 199.2

$^1$H NMR: $\delta_H$ pm 400 MHz, DMSO: 10.70 (1H, bs, NH), 9.12 (1H, bs, NH), 5.32 (1H, s, $CH_{arom}$), 4.82 (2H, bs, $NH_2$), 1.42 (9H, s, $3CH_3$).

B) Synthesis of Polycyclic Systems by Pathway A or Abis

B-1 Synthesis of Precursors

B-1a Synthesis of Precursors for Pathway A

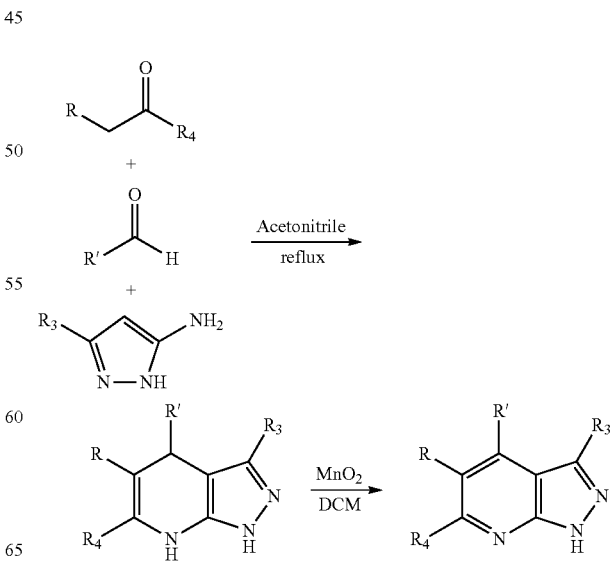

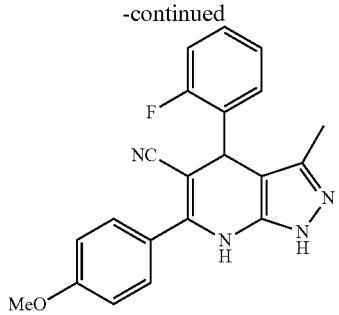

4-(2-fluorophenyl)-6-
(4-methoxyphenyl)-3-
methyl-4,7-dihydro-1H-
pyrazolo[3,4-b]pyridine-5-carbonitrile 1.5 ml (14.27 mmol) of 2-fluorobenzaldehyde and 1.66 g (5.18 mmol) of 3-methyl-1H-pyrazol-5-amine are added respectively to a solution of 2.5 g (14.27 mmol) of 3-(4-methoxyphenyl)-3-oxopropanenitrile in 60 ml of acetonitrile. The reaction mixture is carried at reflux for 16 hours. The solution is allowed to return to room temperature and then the solid is filtered and rinsed several times with acetonitrile to yield 4.5 g (87%) of 4-(2-fluorophenyl)-6-(4-methoxyphenyl)-3-methyl-4,7-dihydro-1H-pyrazolo[3,4-b]pyridine-5-carbonitrile in the form of a white solid.

LCMS (ESI, m/z): (M+1) 361.3

$^1$H NMR: $\delta_H$ pm 400 MHz, DMSO: 11.92 (1H, bs, NH), 9.83 (1H, bs, NH), 7.49 (2H, d, CH$_{arom}$), 7.25-7.33 (2H, m, CH$_{arom}$), 7.14-7.23 (2H, m, CH$_{arom}$), 7.02 (2H, d, CH$_{arom}$), 5.20 (1H, s, CH), 3.80 (3H, s, CH$_3$), 1.81 (3H, s, CH$_3$).

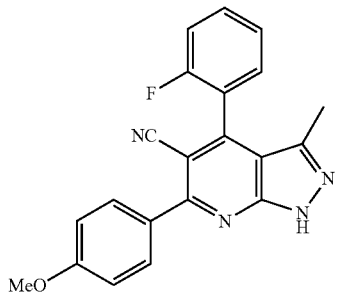

4-(2-fluorophenyl)-6-(4-methoxyphenyl)-
3-methyl-1H-pyrazolo[3,4-b]pyridine-5-carbonitrile 5.43 g (62.4 mmol) of manganese oxide is added to 4.5 g (12.49 mmol) of 4-(2-fluorophenyl)-6-(4-methoxyphenyl)-3-methyl-4,7-dihydro-1H-pyrazolo[3,4-b]pyridine-5-carbonitrile in solution in 60 ml of dichloromethane and 15 ml of methanol. The reaction mixture is placed in an ultrasonic bath for 5 minutes and then stirred at room temperature for 20 hours before being filtered on Dicalite. The filtrate is evaporated to yield 4.1 g (92%) of 4-(2-fluorophenyl)-6-(4-methoxyphenyl)-3-methyl-1H-pyrazolo[3,4-b]pyridine-5-carbonitrile in the form of a yellow solid.

LCMS (ESI, m/z): (M+1) 358.8

$^1$H NMR: $\delta_H$ pm 400 MHz, DMSO: 14.02 (1H, bs, NH), 7.87 (2H, d, CH$_{arom}$), 7.64-7.74 (2H, m, CH$_{arom}$), 7.40-7.56 (2H, m, CH$_{arom}$), 7.13 (2H, d, CH$_{arom}$), 3.86 (3H, s, CH$_3$), 2.01 (3H, s, CH$_3$).

The product below was obtained by procedure B1

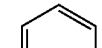

(Z)-4-(2-chloro-2-phenylvinyl)-6-(4-methoxyphenyl)-
3-methyl-1H-pyrazolo[3,4-b]pyridine-5-carbonitrile $^1$H NMR: $\delta_H$ pm 400 MHz, CDCl$_3$: 7.85 (2H, d, CH$_{arom}$), 7.83-7.85 (2H, m, CH$_{arom}$), 7.51-7.55 (3H, m, CH$_{arom}$), 7.40 (1H, s, CH), 7.11 (2H, d, CH$_{arom}$), 3.94 (3H, s, CH$_3$), 2.68 (3H, s, CH$_3$).

B-1b Synthesis of Precursors for Pathway Abis

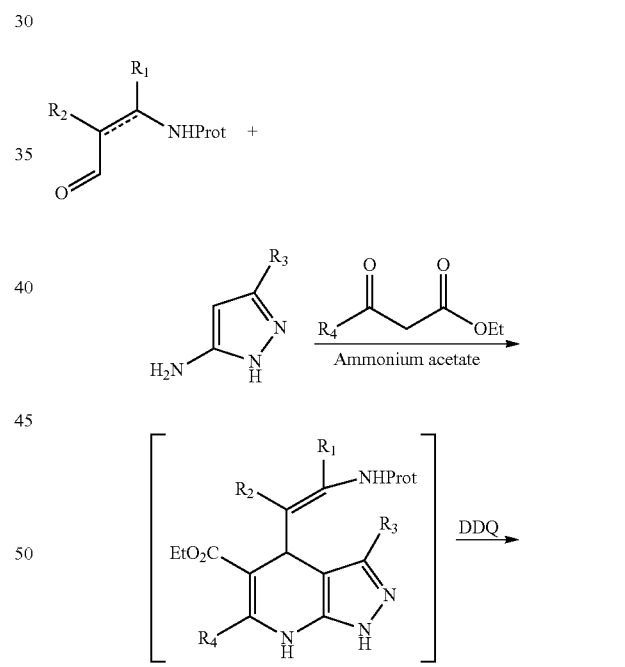

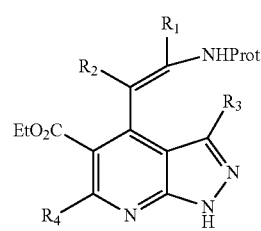

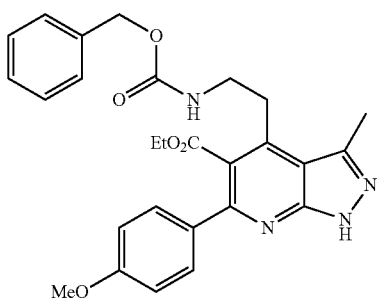

ethyl 4-(2-(benzyloxycarbonylamino)
ethyl)-6-(4-methoxyphenyl)-
3-methyl-1H-pyrazolo[3,4-b]
pyridine-5-carboxylate 578 mg (7.5 mol) of ammonium acetate, 667 mg (3 mmol) of ethyl 3-(4-methoxyphenyl)-3-oxopropanoate, 622 mg (3 mmol) of benzyl 3-oxopropylcarbamate and 291 mg (3 mmol) of 5-methyl-1H-pyrazol-3-amine are introduced in a tube which is then sealed. The tube is placed in an oil bath preheated at 130° C. for 30 minutes. The crude product is partitioned between water and ethyl acetate. The organic phase is dried on magnesium sulfate and concentrated. The product is purified by silica gel chromatography (eluent: cyclohexane/AcOEt 7:3) to yield ethyl 4-(2-(((benzyloxycarbonyl)amino)ethyl)-6-(4-methoxyphenyl)-3-methyl-4,7-dihydro-1H-pyrazolo[3,4-b]pyridine-5-carboxylate. The latter is dissolved in 15 mL of dichloromethane. 885 mg (3.9 mmol) of 2,3-dichloro-5,6-dicyano-1,4-benzoquinone (1.3 eq) is added. The reaction medium is stirred at room temperature for 18 hours. The medium is partitioned between water and dichloromethane. The organic phase is dried on magnesium sulfate and concentrated. The residue is then purified by silica gel chromatography (eluent: cyclohexane/ethyl acetate 7:3) to yield 220 mg (15%) of ethyl 4-(2-(((benzyloxycarbonyl)amino)ethyl)-6-(4-methoxyphenyl)-3-methyl-1H-pyrazolo[3,4-b]pyridine-5-carboxylate.

LCMS (ESI, m/z): (M+1) 489.53

$^1$H NMR: $\delta_H$ pm 400 MHz, DMSO: 13.39 (1H, sl, NH), 7.65 (1H, t, NH), 7.52 (2H, d, CH$_{arom}$), 7.33 (5H, m, CH$_{arom}$), 6.99 (2H, d, CH$_{arom}$), 5.01 (2H, s, CH$_2$), 4.11 (2H, q, CH$_2$), 3.76 (3H, s, OMe), 3.33-3.04 (4H, m, 2CH$_2$), 2.69 (3H, s, CH$_3$), 1.03 (3H, t, CH$_3$).

B-2 Cyclization by Pathway A

B-2a General Case

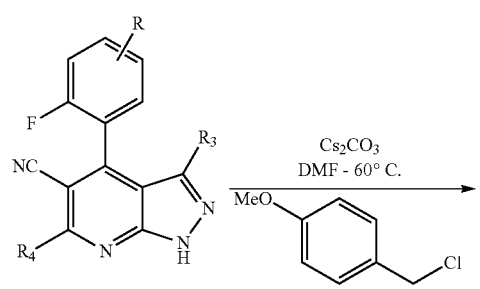

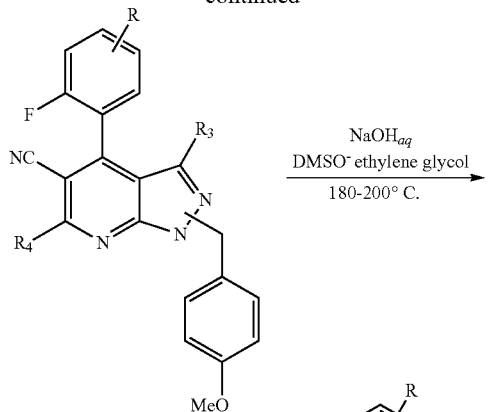

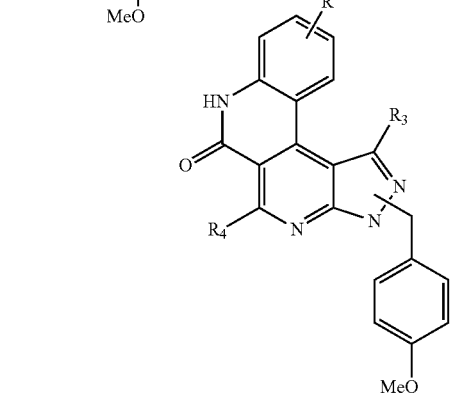

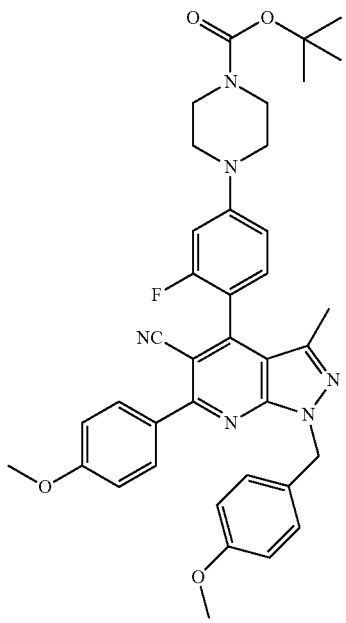

tert-butyl 4-(4-(5-cyano-1-(4-
methoxybenzyl)-6-
(4-methyloxyphenyl)-3-methyl-1H-
pyrazolo[3,4-b]pyridin-4-yl)-3-
fluorophenyl)piperazine-
1-carboxylate 10.48 g (32.2 mmol) of cesium carbonate is added to 8.73 g (16.09 mmol) of tert-butyl 4-(4-(5-cyano-6-(4-methoxyphenyl)-3-methyl-1H-pyrazolo[3,4-b]pyridin-4-yl-3-fluorophenyl)piperazine-1-carboxylate diluted in 80 ml of anhydrous dimethylformamide. The reaction mixture is stirred at room temperature for 30 minutes and then 2.63 ml (19.31 mmol) of 4-methoxybenzyl chloride is added. The reaction mixture is carried at 50° C. for 4 hours. After returning to room temperature, water is added until a stable precipitate appears. The reaction medium is stirred at room temperature for 1 hour and then the precipitate formed is filtered, dried under vacuum and triturated in methanol (40 ml). The solid is filtered and dried to yield 9.88 g (93%) of a mixture comprising tert-butyl 4-(4-(5-cyano-1-(4-methoxybenzyl)-6-(4-methoxyphenyl)-3-methyl-1H-pyrazolo[3,4-b]pyridin-4-yl-3-fluorophenyl)piperazine-1-carboxylate and its regioisomer tert-butyl 4-(4-(5-cyano-2-(4-methoxybenzyl)-6-(4-methoxyphenyl)-3-methyl-1H-pyrazolo[3,4-b]pyridin-4-yl-3-fluorophenyl)piperazine-1-carboxylate in the form of a yellow solid. The isomer mixture is used without prior purification.

LCMS (ESI, m/z): (M+1) 663.4

$^1$H NMR of the majority product: $\delta_H$ pm 400 MHz, DMSO: 7.91 (2H, d, $CH_{arom}$), 7.43-7.51 (1H, m, $CH_{arom}$), 7.29 (2H, d, $CH_{arom}$), 7.15 (2H, d, $CH_{arom}$), 6.93-7.04 (2H, m, $CH_{arom}$), 6.89 (2H, d, $CH_{arom}$), 5.57 (2H, s, $CH_2$), 3.86 (3H, s, $CH_3$), 3.70 (3H, s, $CH_3$), 3.43-3.52 (4H, m, $2CH_2$), 3.30-3.38 (4H, m, $2CH_2$), 2.09 (3H, s, $CH_3$), 1.43 (9H, s, $3CH_3$).

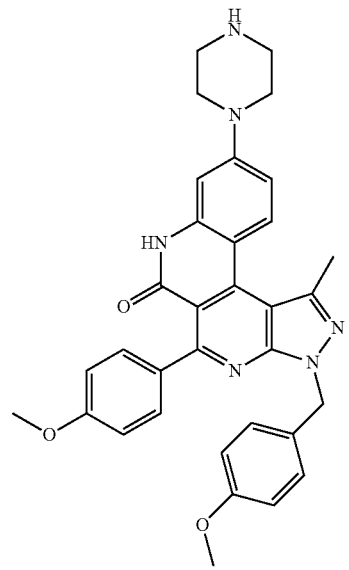

3-(4-methoxybenzyl)-5-(4-methoxyphenyl)-1-methyl-9-(piperazin-1-yl)-3H-benzo[f]pyrazolo[3,4-c][2,7]naphthyridin-6(7H)-one 22 ml (66 mmol) of 3 M aqueous sodium hydroxide solution is added to 4.8 g (7.25 mmol) of the mixture of the two regioisomers tert-butyl 4-(4-(5-cyano-1-(4-methoxybenzyl)-6-(4-methoxyphenyl)-3-methyl-1H-pyrazolo[3,4-b]pyridin-4-yl-3-fluorophenyl)piperazine-1-carboxylate and tert-butyl 4-(4-(5-cyano-2-(4-methoxybenzyl)-6-(4-methoxyphenyl)-3-methyl-1H-pyrazolo[3,4-b]pyridin-4-yl-3-fluorophenyl)piperazine-1-carboxylate dissolved in 75 ml of ethylene glycol and 50 ml of dimethylsulfoxide. The reaction mixture is carried at 200° C. for 24 hours, cooled to 150° C. and poured delicately over crushed ice. The precipitate obtained is filtered to yield 6.1 g (75%) of a mixture of the two regioisomers 3-(4-methoxybenzyl)-5-(4-methoxyphenyl)-1-methyl-9-(piperazin-1-yl)-3H-benzo[f]pyrazolo[3,4-c][2,7]naphthyridin-6(7H)-one and 2-(4-methoxybenzyl)-5-(4-methoxyphenyl)-1-methyl-9-(piperazin-1-yl)-3H-benzo[f]pyrazolo[3,4-c][2,7]naphthyridin-6(7H)-one. Trituration in a methanol/acetonitrile mixture after filtration yields 4.5 g (55%) of 3-(4-methoxybenzyl)-5-(4-methoxyphenyl)-1-methyl-9-(piperazin-1-yl)-3H-benzo[f]pyrazolo[3,4-c][2,7]naphthyridin-6(7H)-one in the form of a yellow solid.

LCMS (ESI, m/z): (M+1) 561.4

$^1$H NMR: $\delta_H$ pm 400 MHz, DMSO: 11.21 (1H, bs, NH), 8.14 (1H, d, $CH_{arom}$), 7.50 (2H, d, $CH_{arom}$), 7.27 (2H, d, $CH_{arom}$), 6.91-6.97 (3H, m, $CH_{arom}$), 6.88 (2H, d, $CH_{arom}$), 6.72-6.76 (1H, m, $CH_{arom}$), 5.55 (2H, s, $CH_2$), 3.82 (3H, s, $CH_3$), 3.70 (3H, s, $CH_3$), 3.20-3.28 (4H, m, $2CH_2$), 2.80-2.90 (4H, m, $2CH_2$), 2.73 (3H, s, $CH_3$).

B-2b Specific Cases

During this step, secondary reactions can take place. For example, the following reaction was observed:

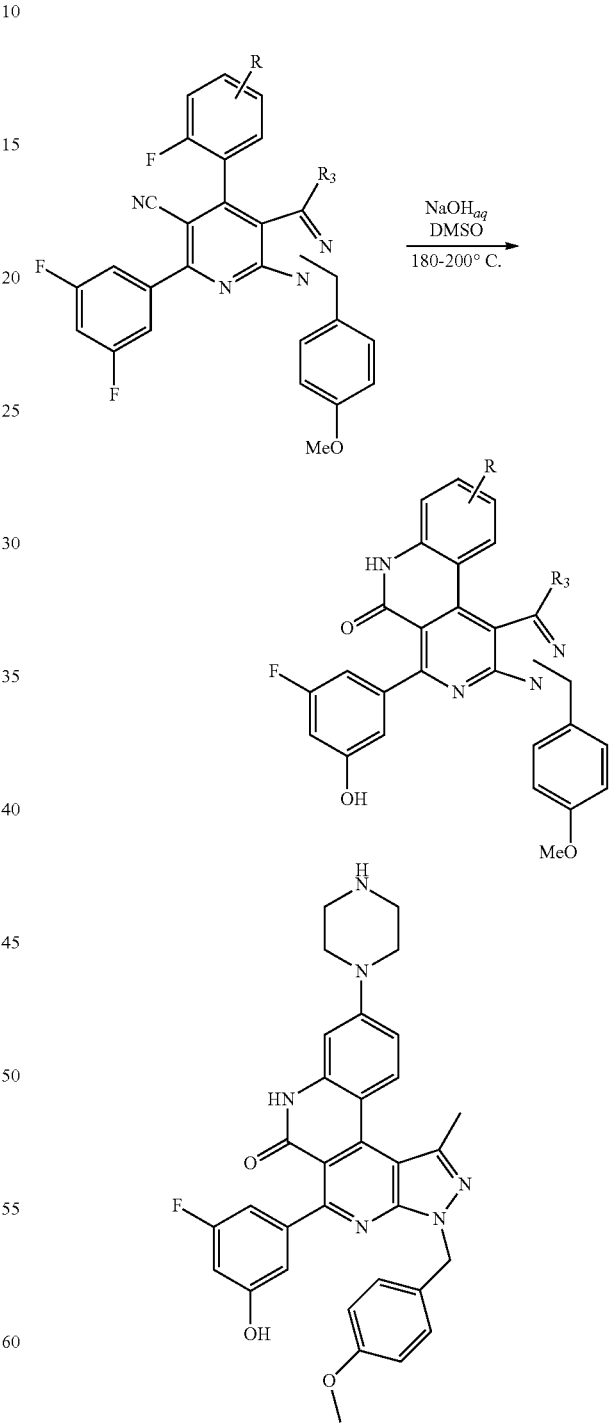

5-(3-fluoro-5-hydroxyphenyl)-3-(4-methoxybenzyl)-1-methyl-9-(piperazin-1-yl)-3H-benzo[f]pyrazolo[3,4-c][2,7]naphthyridin-6(7H)-one 12 ml (60 mmol) of 5 M aqueous sodium hydroxide solution is added to 4 g (5.98 mmol) of the mixture of the two regioisomers tert-butyl 4-(4-(5-cyano-6-(3,5-difluorophenyl)-1-(4-methoxybenzyl)-3-methyl-1H-pyrazolo[3,4-b]pyridin-4-yl-3-fluorophenyl)piperazine-1-carboxylate and tert-butyl 4-(4-(5-cyano-6-(3,5-difluorophenyl)-2-(4-methoxybenzyl)-3-methyl-1H-pyrazolo[3,4-b]pyridin-4-yl-3-fluorophenyl)piperazine-1-carboxylate dissolved in 80 ml of dimethylsulfoxide. The reaction mixture is carried at 190° C. for 5 hours, cooled to room temperature and then poured over crushed ice. The product is extracted with ethyl acetate. The inhomogeneous organic phases are concentrated and dried under vacuum and then the residue is triturated several times with ethyl acetate. The precipitate obtained is filtered to yield 1.6 g (42%) of the mixture of the two regioisomers 5-(3-fluoro-5-hydroxyphenyl)-3-(4-methoxybenzyl)-1-methyl-9-(piperazin-1-yl)-3H-benzo[f]pyrazolo[3,4-c][2,7]naphthyridin-6(7H)-one and 5-(3-fluoro-5-hydroxyphenyl)-2-(4-methoxybenzyl)-1-methyl-9-(piperazin-1-yl)-3H-benzo[f]pyrazolo[3,4-c][2,7]naphthyridin-6(7H)-one in the form of a brown solid.

LCMS (ESI, m/z): (M+1) 565.3

$^1$H NMR of the majority product: $\delta_H$ pm 400 MHz, DMSO: 11.25 (1H, bs, NH), 9.88 (1H, bs, OH), 8.17 (1H, d, $CH_{arom}$), 7.25 (2H, d, $CH_{arom}$), 6.94-7.02 (1H, m, $CH_{arom}$), 6.87 (2H, d, $CH_{arom}$), 6.65-6.77 (3H, m, $CH_{arom}$), 6.53-6.61 (1H, m, $CH_{arom}$), 5.55 (2H, s, $CH_2$), 3.70 (3H, s, $CH_3$), 3.20-3.30 (4H, m, $2CH_2$), 2.81-2.90 (4H, m, $2CH_2$), 2.74 (3H, s, $CH_3$).

B-2c Formation of a Pyranone Ring

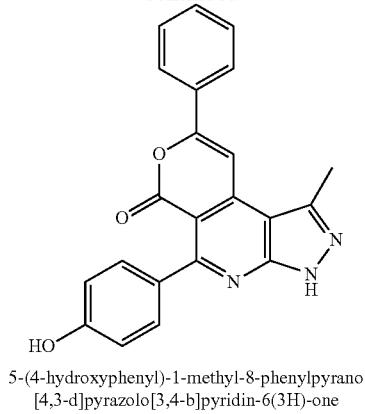

5-(4-hydroxyphenyl)-1-methyl-8-phenylpyrano[4,3-d]pyrazolo[3,4-b]pyridin-6(3H)-one A solution of 6 g (15 mmol) of Z-4-(2-chloro-2-phenylvinyl)-6-(4-methoxyphenyl)-3-methyl-1H-pyrazolo[3,4-b]pyridine-5-carbonitrile dissolved in 70 ml of 70% sulfuric acid is carried at 100° C. for 36 hours. The reaction medium is cooled to room temperature and then poured over crushed ice. The precipitate obtained is filtered and then purified by silica gel chromatography (eluent: 1:1 ethyl acetate/cyclohexane to 1:1 dichloromethane/methanol) to yield 562 mg (10%) of 5-(4-hydroxyphenyl)-1-methyl-8-phenylpyrano[4,3-d]pyrazolo[3,4-b]pyridin-6(3H)-one in the form of a yellow solid.

$^1$H NMR: $\delta_H$ pm 400 MHz, DMSO: 13.69 (1H, bs, NH), 9.66 (1H, bs, OH), 8.07-8.10 (2H, m, $CH_{arom}$), 7.60-7.65 (4H, m, $CH_{arom}$), 7.43 (2H, d, $CH_{arom}$), 6.83 (2H, d, $CH_{arom}$), 2.86 (3H, s, $CH_3$).

B-2d Formation of a Pyridone Ring

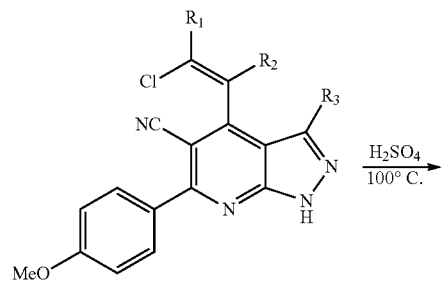

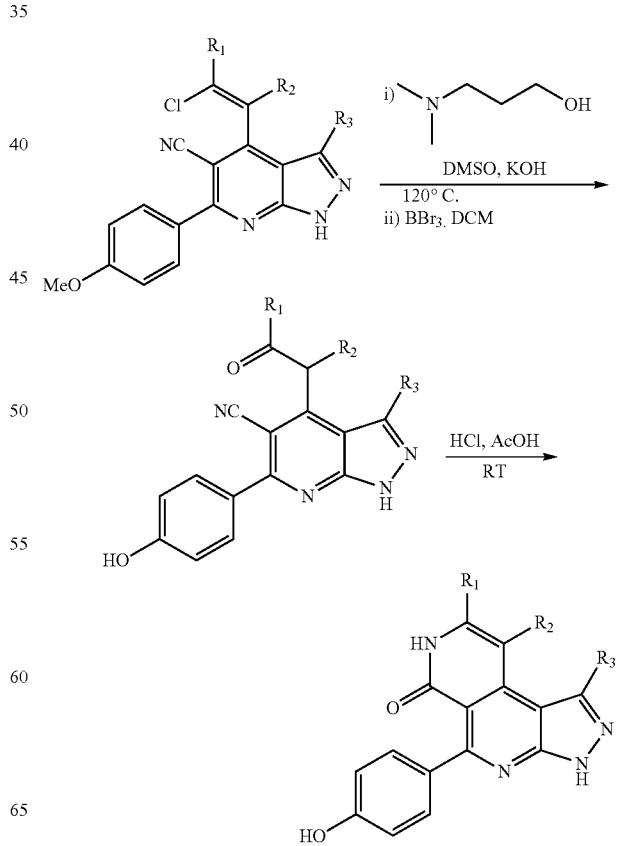

-continued

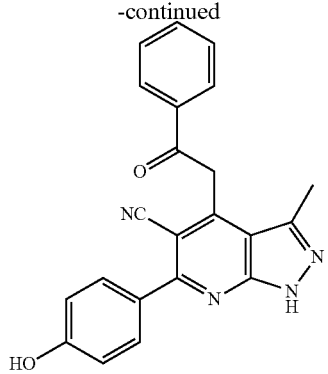

6-(4-hydroxyphenyl)-3-methyl-4-(2-oxo-2-phenylethyl)-
1H-pyrazolo[3,4-b]pyridine-5-carbonitrile 36 g (350 mmol) of 3-(dimethylamino)propan-1-ol and 12 g (21.4 mmol) of potassium hydroxide are added to 12 g (30 mmol) of Z-4-(2-chloro-2-phenylvinyl)-6-(4-methoxyphenyl)-3-methyl-1H-pyrazolo[3,4-b]pyridine-5-carbonitrile dissolved in 100 ml of dimethylsulfoxide and 36 ml of water. The reaction mixture is carried at 120° C. for 3 hours. The reaction medium is cooled to room temperature and then poured over crushed ice. The product is extracted with ethyl acetate. The organic phases are dried on sodium sulfate, filtered and then concentrated. The residue is purified immediately by silica gel chromatography (eluent: 95:5 dichloromethane/methanol). The product is then dissolved in 100 ml of dichloromethane. The reaction medium is cooled in an ice bath before 36 ml (376.5 mmol) of boron tribromide is added slowly. The reaction medium is stirred at room temperature for 3 hours and then added slowly to crushed ice. The solid is filtered, rinsed with water, dried and then purified by silica gel chromatography (eluent: 5:5 cyclohexane/ethyl acetate) to yield 6 g (54%) of 6-(4-hydroxyphenyl)-3-methyl-4-(2-oxo-2-phenylethyl)-1H-pyrazolo[3,4-b]pyridine-5-carbonitrile in the form of a yellow solid.

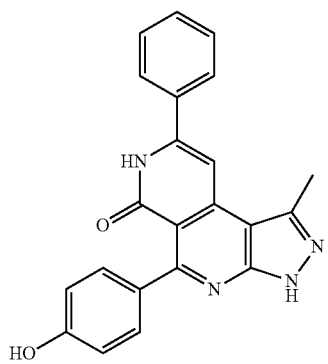

5-(4-hydroxyphenyl)-1-methyl-8-phenyl-3H-
pyrazolo[3,4-c][2,7]naphthyridin-6(7H)-one 2 ml of concentrated hydrochloric acid is added to 4 g (10.87 mmol) of 6-(4-hydroxyphenyl)-3-methyl-4-(2-oxo-2-phenylethyl)-1H-pyrazolo[3,4-b)]pyridine-5-carbonitrile dissolved in 20 ml of acetic acid. The reaction mixture is stirred at room temperature for 20 hours. The reaction medium is poured over crushed ice. The solid is filtered and then purified by reverse-phase preparative HPLC to yield 30 mg (0.75%) of 5-(4-hydroxyphenyl)-1-methyl-8-phenyl-3H-pyrazolo[3,4-c][2,7]naphthyridin-6(7H)-one in the form of a yellow solid.

$^1$H NMR: $\delta_H$ pm 400 MHz, CDCl$_3$: 13.43 (1H, bs, NH), 11.65 (1H, bs, NH), 9.51 (1H, bs, OH), 7.88-7.94 (2H, m, CH$_{arom}$), 7.49-7.65 (3H, m, CH$_{arom}$), 7.30-7.40 (2H, m, CH$_{arom}$), 7.12-7.18 (1H, s, CH$_{arom}$), 6.72-6.80 (2H, m, CH$_{arom}$), 2.78 (3H, s, CH$_3$).

B-3 Cyclization by Pathway Abis

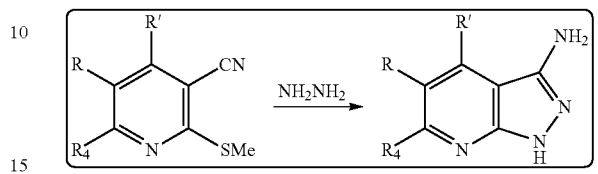

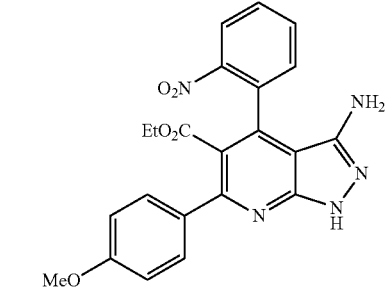

ethyl 3-amino-6-(4-methoxyphenyl)-4-(2-nitrophenyl)-
1H-pyrazolo[3,4-b)]pyridine-5-carboxylate 0.5 ml of hydrazine is added to a solution of 0.21 g (0.46 mmol) of ethyl 5-cyano-2-(4-methoxyphenyl)-4-(2-nitrophenyl)-6-thioxo-1,6-dihydropyridine-3-carboxylate dissolved in 2 ml of ethanol. The reaction medium is carried at 90° C. for 5 hours. The precipitate obtained is filtered and then recrystallized in a methanol/diethyl ether mixture to yield 0.20 g (74%) of ethyl 3-amino-6-(4-methoxyphenyl)-4-(2-nitrophenyl)-1H-pyrazolo[3,4-b]pyridine-5-carboxylate in the form of a yellow solid.

LCMS (ESI, m/z): (M+1) 434.42

$^1$H NMR: $\delta_H$ pm 400 MHz, DMSO: 12.73 (1H, bs, NH), 8.30 (1H, d, CH$_{arom}$), 7.54-7.58 (2H, m, CH$_{arom}$), 7.45-7.52 (3H, m, CH$_{arom}$), 6.91 (2H, d, CH$_{arom}$), 4.22 (2H, bs, NH$_2$), 3.80 (3H, s, CH$_3$), 3.45-3.65 (2H, m, CH$_2$), 0.8 (3H, t, CH$_3$).

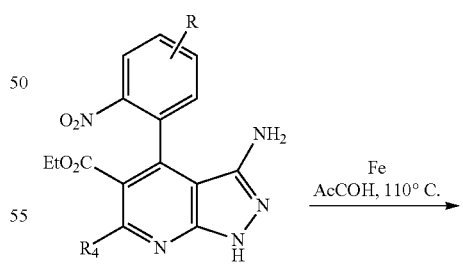

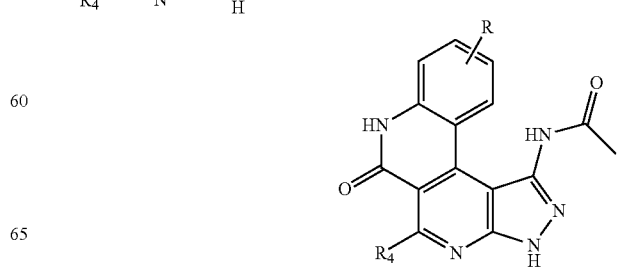

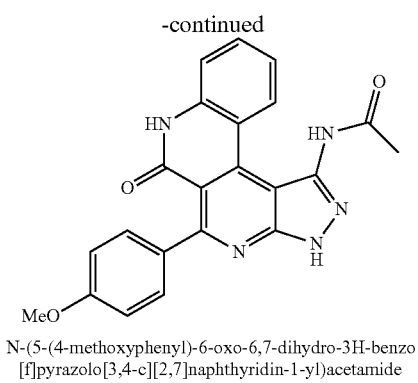

N-(5-(4-methoxyphenyl)-6-oxo-6,7-dihydro-3H-benzo[f]pyrazolo[3,4-c][2,7]naphthyridin-1-yl)acetamide 55 mg (1 mmol) of iron is added to a solution of 87 mg (0.2 mmol) of ethyl 3-amino-6-(4-methoxyphenyl)-4-(2-nitrophenyl)-1H-pyrazolo[3,4-b]pyridine-5-carboxylate dissolved in 2 ml of acetic acid. The reaction medium is carried at 90° C. for 5 hours, and then the precipitate obtained is filtered on Dicalite and rinsed with a 98:2 dichloroethane/methanol mixture. The filtrate is concentrated to yield 45 mg (56%) of N-(5-(4-methoxyphenyl)-6-oxo-6,7-dihydro-3H-benzo[f]pyrazolo[3,4-c][2,7]naphthyridin-1-yl)acetamide in the form of a yellow solid.

LCMS (ESI, m/z): (M+1) 400.4

$^1$H NMR: $\delta_H$ pm 400 MHz, DMSO: 14.0 (1H, bs, NH), 11.6 (1H, bs, NH), 10.6 (1H, bs, NH), 8.45 (1H, d, CH$_{arom}$), 7.20-7.59 (5H, m, CH$_{arom}$), 6.95 (2H, d, CH$_{arom}$), 3.83 (3H, s, CH$_3$), 2.10 (3H, s, CH$_3$).

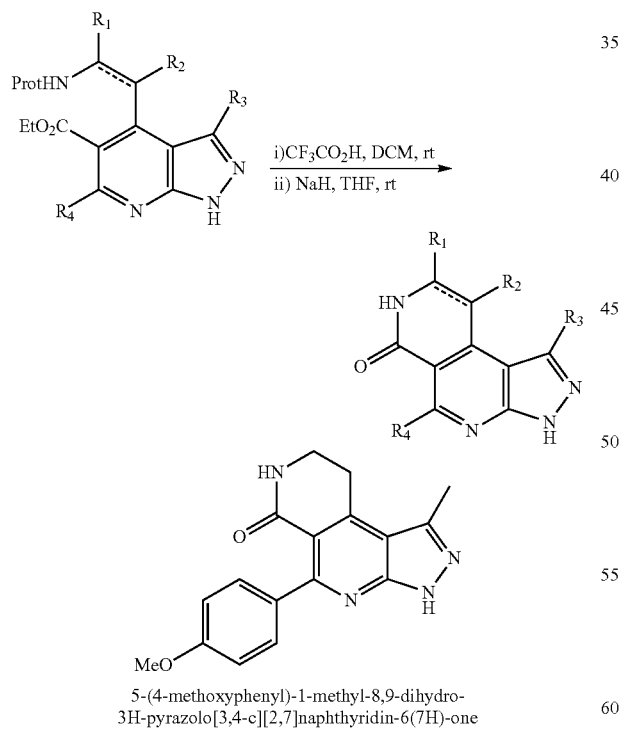

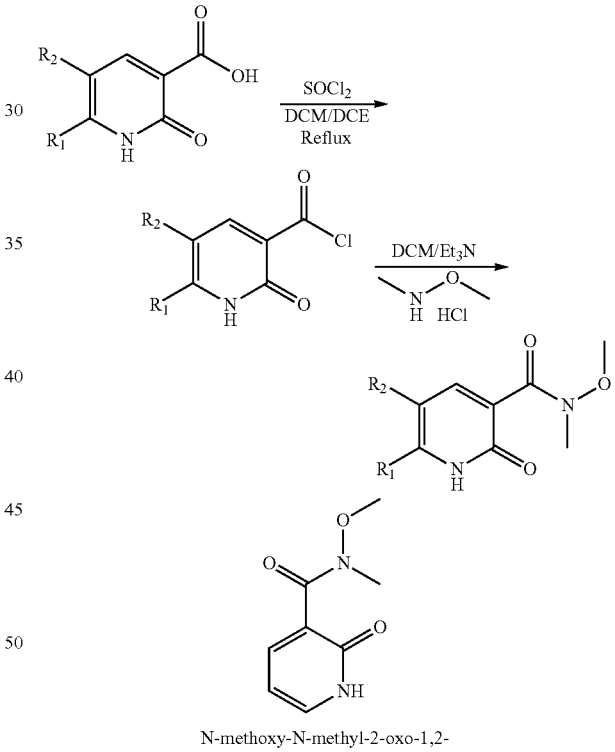

5-(4-methoxyphenyl)-1-methyl-8,9-dihydro-3H-pyrazolo[3,4-c][2,7]naphthyridin-6(7H)-one 8 mL of trifluoroacetic acid is added to a solution of 220 mg (0.45 mmol) of ethyl 4-(2-(benzyloxycarbonylamino)ethyl)-6-(4-methoxyphenyl)-3-methyl-1H-pyrazolo[3,4-b]pyridine-5-carboxylate dissolved in 5 mL of dichloromethane. The reaction medium is stirred at room temperature for 3 hours and then quenched by addition of 1M soda until pH=8 is reached. The product is extracted with ethyl acetate. The organic phases are dried on magnesium sulfate and concentrated to yield ethyl 4-(2-aminoethyl)-6-(4-methoxyphenyl)-3-methyl-1H-pyrazolo[3,4-b]pyridine-5-carboxylate in the form of a yellow oil. The latter is dissolved in 10 mL of anhydrous tetrahydrofurane before adding 15 mg of sodium hydride (60% dispersion in oil). The reaction medium is stirred at 25° C. for 48 hours. The product is extracted with ethyl acetate. The organic phases are dried on magnesium sulfate and concentrated to yield 123 mg (88%) of 5-(4-methoxyphenyl)-1-methyl-8,9-dihydro-3H-pyrazolo[3,4-c][2,7]naphthyridin-6(7H)-one in the form of a yellow oil.

LCMS (ESI, m/z): (M+1) 309.13

$^1$H NMR: $\delta_H$ pm 400 MHz, DMSO: 12.70 (1H, sl, NH), 7.40 (2H, d, CHarom), 6.80 (2H, d, CHarom), 3.80 (3H, s, OMe), 3.40 (2H, m, CH$_2$), 3.05 (2H, t, CH$_2$), 2.62 (3H, s, CH$_3$).

C) Pathway B: Synthesis of Polycyclic Systems by Formation of Pyridine Ring B
C-1 Synthesis of Precursors
C-1a Synthesis of Non-Alkylated Keto-Pyridone Precursors
Step 1:

N-methoxy-N-methyl-2-oxo-1,2-dihydropyridine-3-carboxamide 20 ml (270 mmol) of thionyl chloride and 1 ml of dimethylformamide are added respectively to 12.5 g (90 mmol) of 2-hydroxynicotinic acid in suspension in a mixture of 80 ml of dichloromethane and 20 ml of 1,2-dichloroethane. The suspension is stirred at reflux for 2.5 hours. The reaction mixture is cooled to room temperature and the precipitate formed is filtered to yield (11.98 g) of 2-hydroxynicotinic chloride. The solid is suspended in 150 ml of dichloromethane, and then 7.42 g (76 mmol) of N,O-dimethylhydroxylamine hydrochloride and 21.37 ml (152 mmol) of triethylamine are added successively. The reaction mixture is stirred for 2 hours at room temperature, the solvent is evaporated, and then the solid is taken up in a minimum of ethyl acetate (70 ml). The solid is filtered (triethylamine salt) and the filtrate is concentrated to yield after purification by silica gel chromatography (eluent: 10:1 dichloromethane/methanol) 10.5 g (64%) of N-methoxy-N-methyl-2-oxo-1,2-dihydropyridine-3-carboxamide in the form of a white solid.

LCMS (ESI, m/z): (M+1) 183.15

$^1$H NMR: $\delta_H$ pm 400 MHz, DMSO: 11.89 (1H, bs, NH), 7.44-7.49 (2H, m, CH$_{arom}$), 6.21 (1H, dd, CH$_{arom}$), 3.58 (3H, s, CH$_3$), 3.16 (3H, s, CH$_3$).

Step 2:

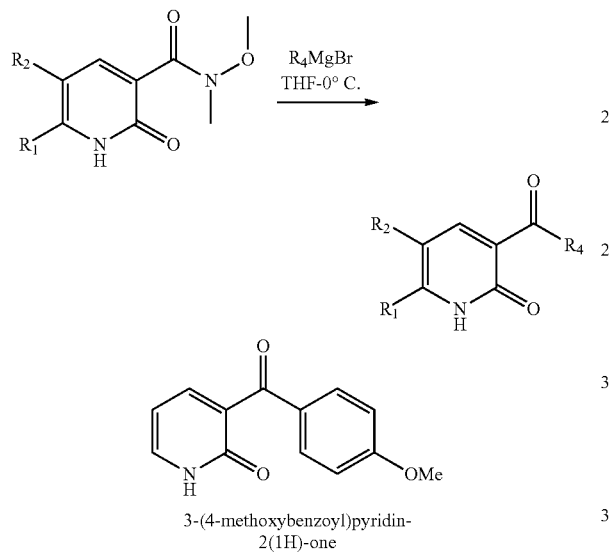

3-(4-methoxybenzoyl)pyridin-2(1H)-one 99 ml (49.4 mmol) of a 0.5 M solution of 4-(methoxyphenyl)magnesium bromide in hexane is added drop by drop at 0° C. under argon to a solution of 4.5 g (24.7 mmol) of N-methoxy-N-methyl-2-oxo-1,2-dihydropyridine-3-carboxamide in 100 ml of anhydrous tetrahydrofuran. The reaction mixture is stirred for 30 min at 0° C. and then for 1.5 hours at room temperature. 1 M hydrochloric acid solution is added, and the product is extracted several times with ethyl acetate. The organic phases are combined, dried on magnesium sulfate and concentrated. The solid is triturated in a minimum of methanol to yield 2.8 g (50%) of 4-ethoxyphenyl-3-oxopropanenitrile in the form of a white solid.

LCMS (ESI, m/z): (M+1) 230.15

$^1$H NMR: $\delta_H$ pm 400 MHz, DMSO: 12.04 (1H, bs, NH), 7.75 (2H, d, CH$_{arom}$), 7.03 (2H, d, CH$_{arom}$), 7.61-7.65 (2H, m, CH$_{arom}$), 6.32 (1H, dd, CH$_{arom}$), 3.84 (3H, s, CH$_3$).

C-1b Synthesis of Alkylated 3-Keto-Pyridone Precursors

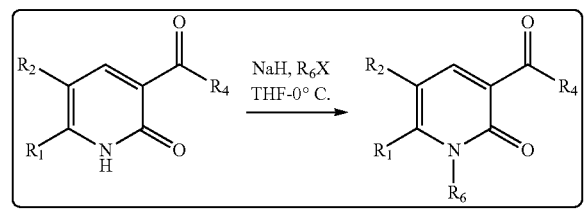

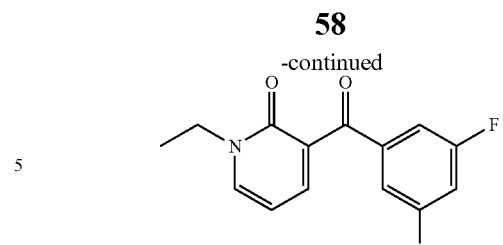

3-(3,5-difluorobenzoyl)-1-ethylpyridin-2(1H)-one 187 mg (4.68 mmol) of sodium hydride 60% dispersion in oil is added to 0.44 g (1.87 mmol) of 3-(3,5-difluorobenzoyl)pyridin-2(1H)-one dissolved in 15 ml of anhydrous dimethylformamide at 0° C. 379 mg (2.43 mmol) of iodoethane is added to this mixture. The reaction mixture is stirred at 0° C. for 10 minutes and then for 1 hour at room temperature. 1 N HCl solution is added and then the product is extracted several times with ethyl acetate. The organic phases are combined, washed with saturated sodium chloride solution, dried on magnesium sulfate and concentrated. The residue is purified by silica gel chromatography (eluent: 10:1 dichloromethane/methanol) to yield 221 mg (50%) of 3-(3,5-difluorobenzoyl)-1-ethylpyridin-2(1H)-one in the form of a yellow solid.

LCMS (ESI, m/z): (M+1) 264.21

$^1$H NMR: $\delta_H$ pm: 400 MHz, DMSO: 7.95 (1H, dd, CH$_{arom}$), 7.59 (1H, dd, CH$_{arom}$), 7.32 (2H, bd, CH$_{arom}$), 7.00 (1H, ddd, CH$_{arom}$), 6.36 (1H, dd, CH$_{arom}$), 4.06 (2H, q, CH$_2$), 1.40 (3H, t, CH$_3$).

C-1c Synthesis of 3-Benzoyl-Pyranone Precursors

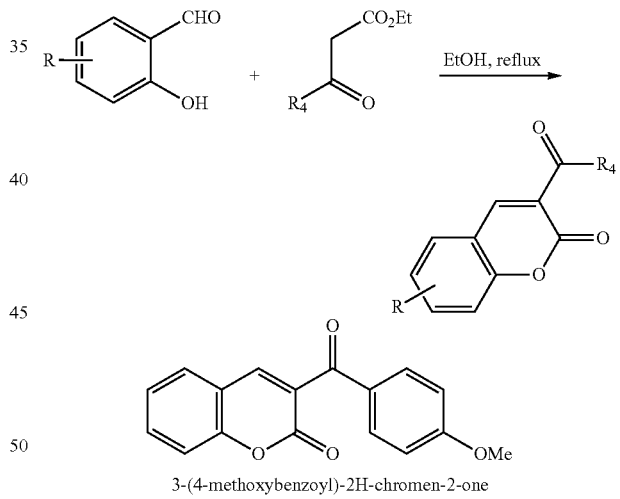

3-(4-methoxybenzoyl)-2H-chromen-2-one 3.64 g (16.38 mmol) of ethyl 3-(4-methoxyphenyl)-3-oxopropanoate and 1.39 g of piperidine (16.38 mmol) are added to a solution of 2 g (16.38 mmol) of 2-hydroxybenzaldehyde in 15 ml of ethanol. The reaction mixture is stirred for 8 hours at reflux. The solution is cooled, and then the white solid formed is filtered and rinsed with a minimum of ethanol to yield 4.02 g (88%) of 3-(4-methoxybenzoyl)-2H-chromen-2-one.

LCMS (ESI, m/z): (M+1) 281.17

$^1$H NMR: $\delta_H$ pm 400 MHz, DMSO: 8.36 (1H, s, CH$_{arom}$), 7.95 (2H, d, CH$_{arom}$), 7.84 (1H, d, CH$_{arom}$), 7.73 (1H, dd, CH$_{arom}$), 7.50 (1H, d, CH$_{arom}$), 7.43 (1H, dd, CH$_{arom}$), 7.07 (2H, d, CH$_{arom}$), 3.87 (3H, s, CH$_3$).

C-2 Cyclization

Procedure C2a: Case of Non-Alkylated Compounds

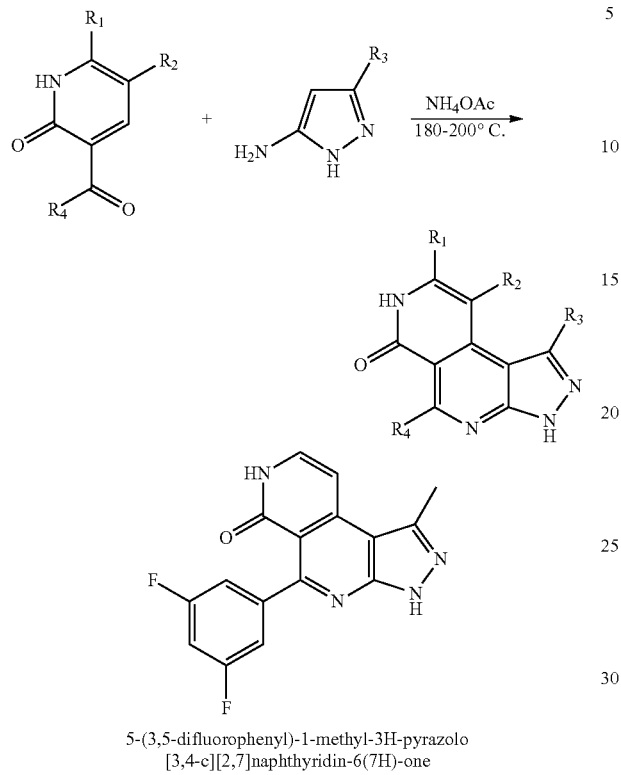

5-(3,5-difluorophenyl)-1-methyl-3H-pyrazolo[3,4-c][2,7]naphthyridin-6(7H)-one

A mixture of 1.09 g (5.47 mmol) of (2-hydroxypyridin-3-yl)(phenyl)methanone, 531 mg (5.47 mmol) of 3-amino-5-methyl-pyrazole and 8.44 mg (109 mmol) of ammonium acetate is carried at 200° C. without solvent for 12 h. The solution is placed at room temperature, and then the solid is dissolved in a water/ethyl acetate mixture. The phases are separated and the aqueous phase is extracted several times with ethyl acetate. The organic phases are mixed, dried on magnesium sulfate and concentrated. The solid residue is taken up in a minimum of methanol and then filtered to yield 0.3 g (17.5%) of 5-(3,5-difluorophenyl)-1-methyl-3H-pyrazolo[3,4-c][2,7]naphthyridin-6(7H)-one in the form of a yellow powder.

LCMS (ESI, m/z): (M+1) 313.11

$^1$H NMR: $\delta_H$ pm 400 MHz, DMSO: 13.46 (1H, bs, NH), 11.01 (1H, bd, NH), 7.40 (1H, ddd, CH$_{arom}$), 7.31 (1H, ddd, CH$_{arom}$), 7.11-7.13 (2H, m, CH$_{arom}$), 6.58 (1H, dd, CH$_{arom}$), 1.83 (3H, s, CH$_3$).

Procedure C2b: Case of Alkylated Compounds

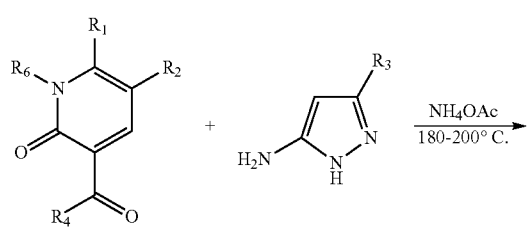

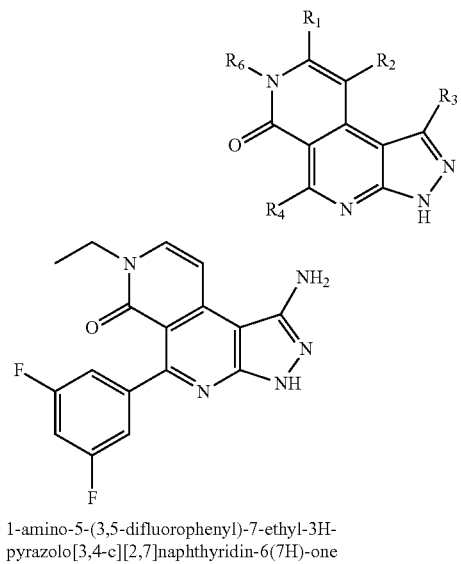

1-amino-5-(3,5-difluorophenyl)-7-ethyl-3H-pyrazolo[3,4-c][2,7]naphthyridin-6(7H)-one 91 mg (0.346 mmol) of 3-(3,5-difluorobenzoyl)-1-ethylpyridin-2(1H)-one with 69 mg (0.346 mmol) of tert-butyl 3-amino-1H-pyrazol-5-ylcarbamate and 533 mg (6.91 mmol) of ammonium acetate are added to a boiling flask. The mixture is carried at 200° C. dry (i.e., without solvent) for 15 minutes. The solution is placed at room temperature, and then the solid is dissolved in a water/ethyl acetate mixture. The phases are separated and the aqueous phase is extracted several times with ethyl acetate. The organic phases are mixed, dried on magnesium sulfate and concentrated. The product is purified by silica gel chromatography (eluent: 10:1 dichloromethane/methanol) to yield 32 mg (27%) of 1-amino-5-(3,5-difluorophenyl)-7-ethyl-3H-pyrazolo[3,4-c][2,7]naphthyridin-6(7H)-one.

LCMS (ESI, m/z): (M+1) 342.22

$^1$H NMR: $\delta_H$ pm 400 MHz, DMSO: 12.40 (1H, bs, NH), 7.70 (1H, d, CH$_{arom}$), 7.35 (1H, ddd, CH$_{arom}$), 7.11-7.14 (2H, m, CH$_{arom}$), 6.58 (1H, d, CH$_{arom}$), 4.33 (2H, bs, NH$_2$), 3.79 (2H, q, CH$_2$), 1.51 (3H, t, CH$_3$).

Procedure C2c: Case of Tricyclic Pyranones

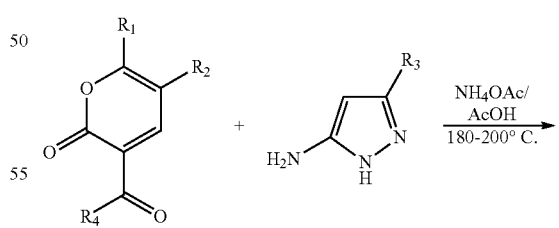

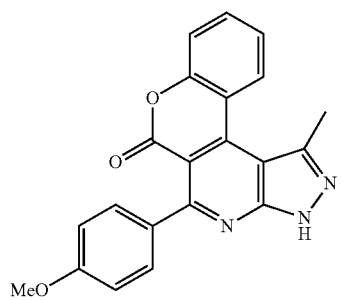

5-(4-methoxyphenyl)-1-methylchromeno
[4,3-d]pyrazolo[3,4-b]pyridin-6(3H)-one

A mixture of 2.1 g (7.49 mmol) of 3-(4-methoxybenzoyl)-2H-chromen-2-one with 728 mg (7.49 mmol) of 3-amino-5-methyl-pyrazole in 15 ml of acetic acid is heated at 110° C. for 10 minutes. 2.3 g (30 mmol) of ammonium acetate is then added and then the mixture is carried at 150° C. for 3 h. The solution is placed at room temperature and then 30 ml of ethyl ether and 5 ml of methanol are added. The white solid formed is filtered and then rinsed with diethyl ether to yield 810 mg of 5-(4-methoxyphenyl)-1-methylchromeno[4,3-d]pyrazolo[3,4-b]pyridin-6(3H)-one.

LCMS (ESI, m/z): (M+1) 342.22

$^1$H NMR: $\delta_H$ pm 400 MHz, DMSO: 14.00 (1H, bs, NH), 8.42 (1H, d, $CH_{arom}$), 7.68 (1H, ddd, $CH_{arom}$), 7.60 (2H, dd, $CH_{arom}$), 7.52 (1H, d, $CH_{arom}$), 7.50 (1H, d, $CH_{arom}$), 6.98 (2H, d, $CH_{arom}$), 3.84 (3H, s, $CH_3$), 2.83 (3H, t, $CH_3$).

D) Pathway C: Synthesis of Polycyclic Systems by Formation of Pyrazole Ring C

D-1 Synthesis of Precursors

D-1a General Pathway

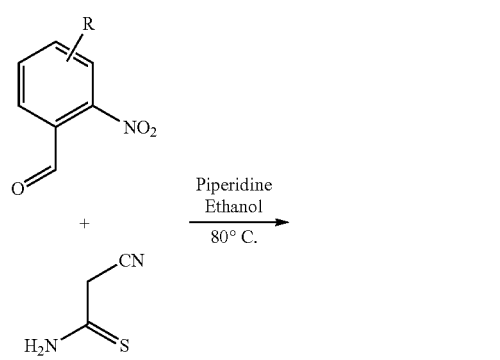

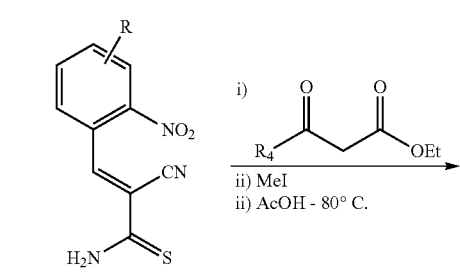

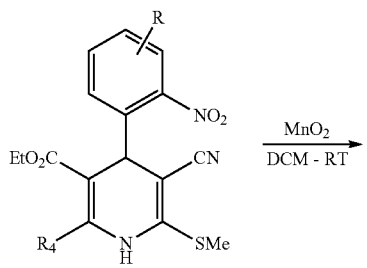

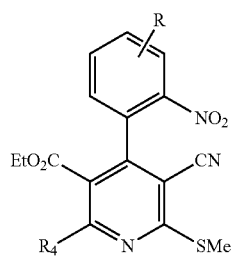

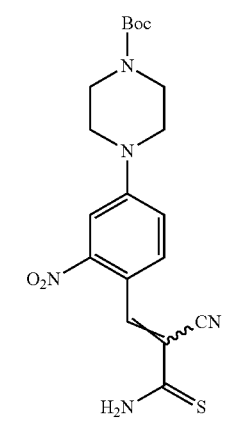

tert-butyl 4-(4-(3-amino-2-cyano-3-thioxoprop-1-enyl)-3-nitrophenyl)piperazine-1-carboxylate 1.5 g (15 mmol) of 2-cyanoethanethioamide, 60 ml of ethanol and one drop of piperidine are added respectively to 5 g (15 mmol) of tert-butyl 4-(4-formyl-3-nitrophenyl)piperazine-1-carboxylate. The reaction mixture is stirred at room temperature for 12 hours. The precipitate obtained is filtered to yield 5.2 g (83%) of tert-butyl 4-(4-(3-amino-2-cyano-3-thioxoprop-1-enyl)-3-nitrophenyl)piperazine-1-carboxylate in the form of a yellow solid.

LCMS (ESI, m/z): (M+1) 418.48

$^1$H NMR: $\delta_H$ pm 400 MHz, DMSO: 10.10 (1H, bs, NH), 9.45 (1H, bs, NH), 8.25 (1H, s, $CH_{arom}$), 7.95 (1H, d, $CH_{arom}$), 7.60 (1H, d, $CH_{arom}$), 6.35 (1H, dd, $CH_{arom}$), 3.50 (8H, m, $4CH_2$), 1.42 (9H, s, $3CH_3$).

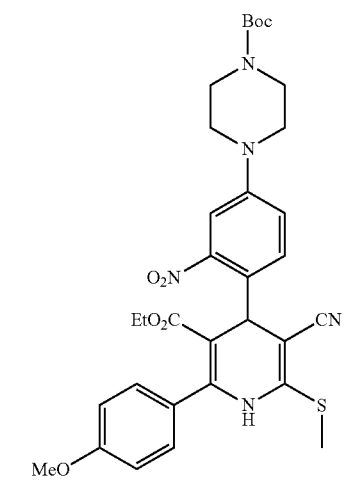

tert-butyl 4-(4-(3-cyano-5-(ethoxycarbonyl)-6-(4-methoxyphenyl)-2-(methylthio)-1,4-dihydropyridin-4-yl)-3-nitrophenyl)piperazine-1-carboxylate 0.55 g (2.5 mmol) of ethyl 3-(4-methoxyphenyl)-3-oxopropanoate, 10 ml of ethanol and 0.3 ml (3 mmol) of piperidine are added respectively to 1 g (2.5 mmol) of tert-butyl 4-(4-(3-amino-2-cyano-3-thioxoprop-1-enyl)-3-nitrophenyl)piperazine-1-carboxylate. The reaction mixture is stirred at room temperature for 5 h and then 0.31 ml (5 mmol) of methyl iodide is added. After 12 h of stirring, 3 ml of acetic acid is added and the reaction medium is carried at 50° C. for 24 hours. After returning to room temperature, the solvents are evaporated and the residue is purified by silica gel chromatography (eluent: 3:7 cyclohexane/ethyl acetate) to yield 1.3 g (83%) of tert-butyl 4-(4-(3-cyano-5-(ethoxycarbonyl)-6-(4-methoxyphenyl)-2-(methylthio)-1,4-dihydropyridine-4-yl)-3-nitrophenyl)piperazine-1-carboxylate in the form of a light yellow powder.

LCMS (ESI, m/z): (M+1) 636.24

$^1$H NMR: $\delta_H$ pm 400 MHz, DMSO: 9.80 (1H, s, NH), 7.34 (1H, s, CH$_{arom}$), 7.32 (1H, d, CH$_{arom}$), 7.30 (1H, d, CH$_{arom}$), 7.22 (2H, d, CH$_{arom}$), 6.96 (2H, d, CH$_{arom}$), 5.04 (1H, s, CH), 3.55 (3H, s, CH$_3$), 3.52-3.54 (2H, m, CH$_2$), 3.40-3.50 (4H, m, 2CH$_2$), 3.20-3.30 (4H, m, 2CH$_2$), 2.60 (3H, s, CH$_3$), 1.42 (9H, s, 3CH$_3$), 0.75 (3H, t, CH$_3$).

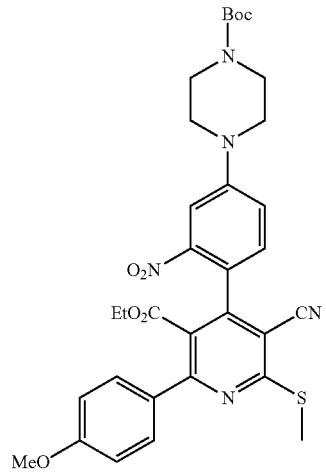

tert-butyl 4-(4-(3-cyano-5-(ethoxycarbonyl)-6-(4-methoxyphenyl)-2-(methylthio)pyridin-4-yl)-3-nitrophenyl)piperazine-1-carboxylate 89 mg (1 mmol) of manganese oxide is added to 0.13 g (0.20 mmol) of tert-butyl 4-(4-(3-cyano-5-(ethoxycarbonyl)-6-(4-methoxyphenyl)-2-(methylthio)-1,4-dihydropyridine-4-yl)-3-nitrophenyl)piperazine-1-carboxylate in solution in 3.25 ml of dichloromethane. The reaction mixture is placed in an ultrasonic bath for 30 minutes and then stirred at room temperature for 60 hours. It is then filtered on Dicalite and rinsed with dichloromethane to yield 110 mg (85%) of tert-butyl 4-(4-(3-cyano-5-(ethoxycarbonyl)-6-(4-methoxyphenyl)-2-(methylthio)pyridin-4-yl)-3-nitrophenyl) piperazine-1-carboxylate in the form of a yellow solid.

LCMS (ESI, m/z): (M+1) 634.71

$^1$H NMR: $\delta_H$ pm 400 MHz, DMSO: 7.70 (1H, s, CH$_{arom}$), 7.65 (2H, d, CH$_{arom}$), 7.37-7.43 (2H, m, CH$_{arom}$), 7.06 (2H, d, CH$_{arom}$), 3.85 (3H, s, CH$_3$), 3.75-3.85 (2H, m, CH$_2$), 3.30-3.45 (8H, m, 4CH$_2$), 2.73 (3H, s, CH$_3$), 1.43 (9H, s, 3CH$_3$), 0.75 (3H, t, CH$_3$).

D-1b Alternative Pathway

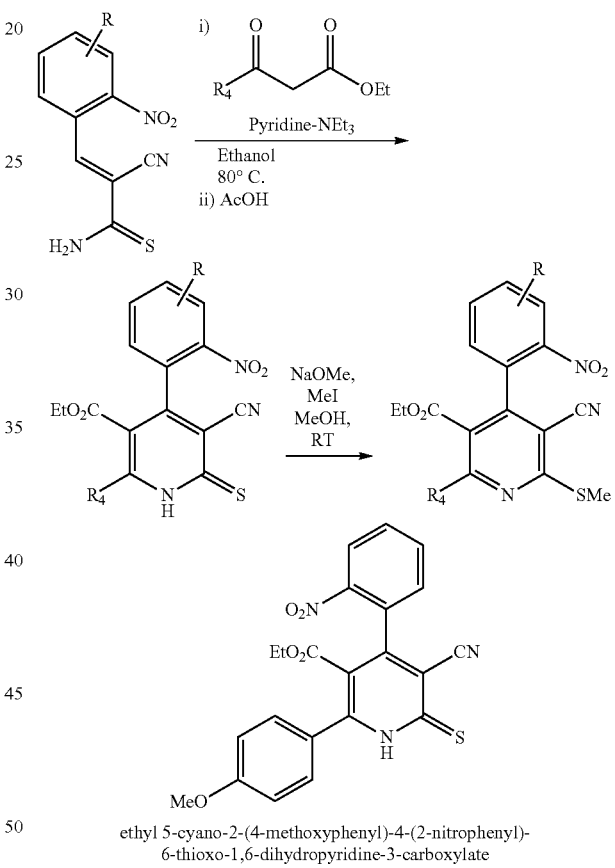

ethyl 5-cyano-2-(4-methoxyphenyl)-4-(2-nitrophenyl)-6-thioxo-1,6-dihydropyridine-3-carboxylate 2.22 g (10 mmol) of ethyl 3-(4-methoxyphenyl)-3-oxopropanoate, 50 ml of ethanol, 5 ml of pyridine and 0.5 ml of triethylamine are added respectively to 2.33 g (10 mmol) of 2-cyano-3-(2-nitrophenyl)prop-2-enethioamide. The reaction mixture is stirred at reflux for 5 hours. After returning to room temperature, the solvent is evaporated and the reaction mixture is poured over crushed ice. Acetic acid is added until an acidic pH (2 to 3) is obtained. The precipitate formed is filtered, rinsed with water and diethyl ether, and then dried under vacuum to yield 4.35 g (92%) of ethyl 5-cyano-2-(4-methoxyphenyl)-4-(2-nitrophenyl)-6-thioxo-1,6-dihydropyridine-3-carboxylate in the form of a yellow powder.

LCMS (ESI, m/z): (M+1) 436.45.

$^1$H NMR: $\delta_H$ pm 400 MHz, DMSO: 12.0 (1H, s, NH), 8.40 (1H, d, CH$_{arom}$), 7.86 (1H, dd, CH$_{arom}$), 7.82 (1H, dd, CH$_{arom}$), 7.64 (1H, d, CH$_{arom}$), 7.45 (2H, d, CH$_{arom}$), 6.96 (2H, d, CH$_{arom}$), 3.55 (3H, s, CH$_3$), 3.52 (2H, m, CH$_2$), 0.75 (3H, t, CH$_3$).

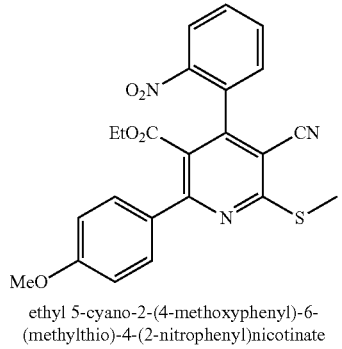 [SMILES: CCOC(=O)c1c(-c2ccc(OC)cc2)nc(SC)c(C#N)c1-c1ccccc1[N+](=O)[O-]]

ethyl 5-cyano-2-(4-methoxyphenyl)-6-(methylthio)-4-(2-nitrophenyl)nicotinate 69 mg (3 mmol) of sodium is added at room temperature in small portions to 0.4 ml of methanol. After the sodium disappears, 870 mg (2 mmol) of ethyl 5-cyano-2-(4-methoxyphenyl)-4-(2-nitrophenyl)-6-thioxo-1,6-dihydropyridine-3-carboxylate is added. The reaction mixture is stirred for 5 minutes, and then 0.18 ml (3 mmol) of methyl iodide is added and stirring is continued for 3 hours. The solvent is concentrated and the precipitate formed is filtered, rinsed with water and then diethyl ether and then dried under vacuum to yield 0.53 g (59%) of ethyl 5-cyano-2-(4-methoxyphenyl)-6-(methylthio)-4-(2-nitrophenyl)nicotinate in the form of a yellow powder.

LCMS (ESI, m/z): (M+1) 450.48

$^1$H NMR: δ$_H$ pm 400 MHz, DMSO: 8.37 (1H, dd, CH$_{arom}$), 7.97 (1H, dd, CH$_{arom}$), 7.85 (1H, dd, CH$_{arom}$), 7.64 (1H, d, CH$_{arom}$), 7.60 (2H, d, CH$_{arom}$), 7.10 (2H, d, CH$_{arom}$), 3.55 (3H, s, CH$_3$), 3.52 (2H, m, CH$_2$), 2.55 (3H, s, CH$_3$), 0.75 (3H, t, CH$_3$).

D-2 Pathway C: Sequential Formation of Rings A and C

D-2a Use of Iron as a Reducing Element

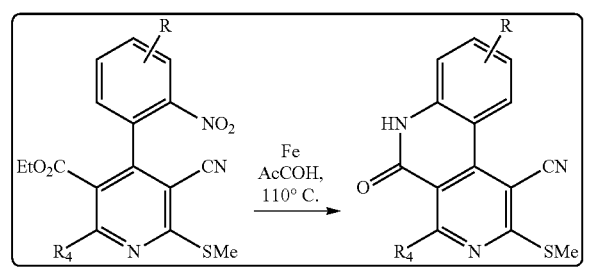

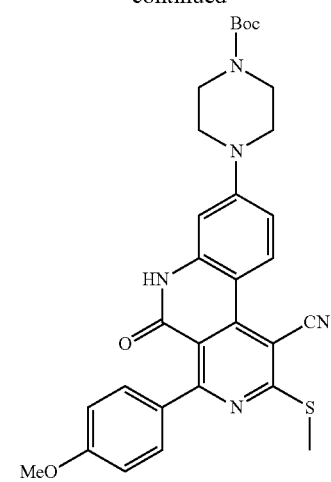

tert-butyl 4-(1-cyano-4-(4-methoxyphenyl)-2-(methylthio)-5-oxo-5,6-dihydrobenzo[c][2,7]naphthyridin-8-yl)piperazine-1-carboxylate 0.48 g (8.6 mmol) of iron is added to a solution of 1 g (1.7 mmol) of tert-butyl 4-(4-(3-cyano-5-(ethoxycarbonyl)-6-(4-methoxyphenyl)-2-(methylthio)pyridin-4-yl)-3-nitrophenyl)piperazine-1-carboxylate dissolved in 8.82 ml of acetic acid. The reaction medium is carried at 90° C. for 4 hours. The precipitate obtained is filtered on Dicalite and then rinsed with a 98:2 dichloroethane/methanol mixture. The filtrate is concentrated to yield 0.63 g (66%) of tert-butyl 4-(1-cyano-4-(4-methoxyphenyl)-2-(methylthio)-5-oxo-5,6-dihydrobenzo[c][2,7]naphthyridin-8-yl)piperazine-1-carboxylate in the form of a yellow solid.

LCMS (ESI, m/z): (M+1) 558.66

$^1$H NMR: δ$_H$ pm 400 MHz, DMSO: 11.41 (1H, bs, NH), 8.81 (1H, d, CH$_{arom}$), 7.59 (2H, d, CH$_{arom}$), 7.06 (1H, s, CH$_{arom}$), 6.95 (2H, d, CH$_{arom}$), 6.69 (1H, d, CH$_{arom}$), 3.83 (3H, s, CH$_3$), 3.26-3.34 (8H, m, 4CH$_2$), 2.50 (3H, s, CH$_3$), 1.43 (9H, s, 3CH$_3$).

D-2b Use of Tin Chloride as Reducing Element

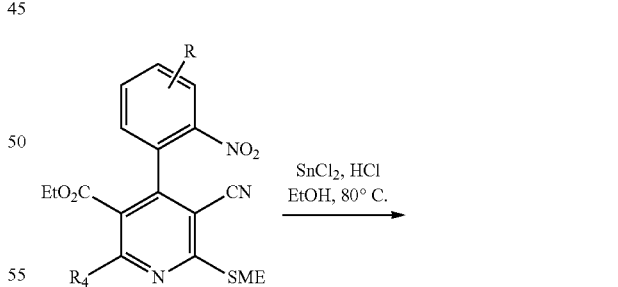

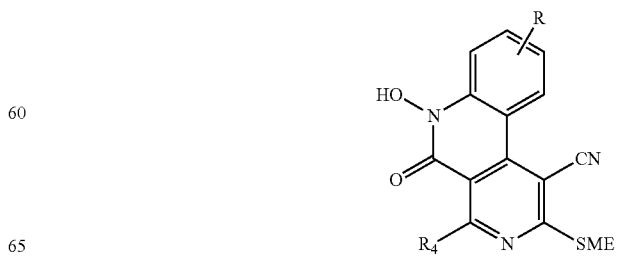

-continued

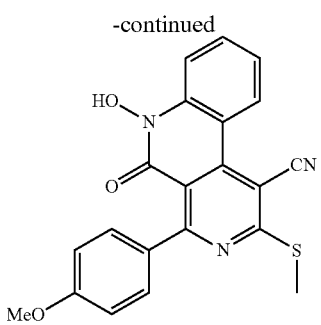

6-hydroxy-4-(4-methoxyphenyl)-2-(methylthio)-5-oxo-
5,6-dihydrobenzo[c][2,7]naphthyridine-1-carbonitrile 12.05 g (53.4 mmol) of tin chloride dihydrate and 14 ml of concentrated hydrochloric acid are added to 4 g (8.9 mmol) of ethyl 5-cyano-2-(4-methoxyphenyl)-4-(2-nitrophenyl)-6-thioxo-1,6-dihydropyridine-3-carboxylate dissolved in 160 ml of ethanol. The reaction medium is carried at 65° C. for 4 hours. The precipitate obtained is filtered, rinsed with isopropanol and then dried to yield 2.78 g (80%) of 6-hydroxy-4-(4-methoxyphenyl)-2-(methylthio)-5-oxo-5,6-dihydrobenzo[c][2,7]naphthyridine-1-carbonitrile in the form of a yellow solid.

$^1$H NMR: $\delta_H$ pm 400 MHz, DMSO: 11.48 (1H, bs, NH), 9.13 (1H, d, CH$_{arom}$), 7.80-7.86 (2H, m, CH$_{arom}$), 7.67 (2H, d, CH$_{arom}$), 7.45-7.50 (1H, m, CH$_{arom}$), 7.01 (2H, d, CH$_{arom}$), 3.85 (3H, s, CH$_3$), 2.72 (3H, s, CH$_3$).

D-2c Formation of Ring C

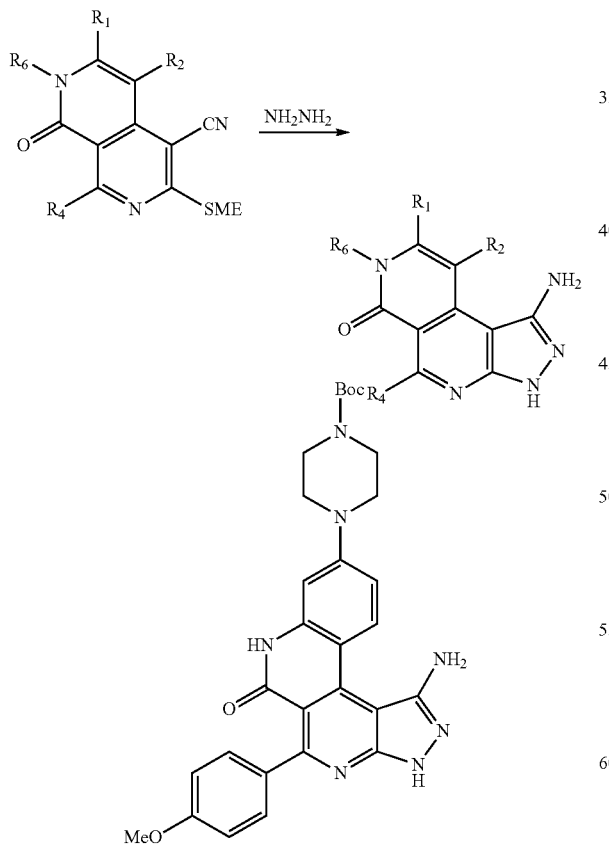

tert-butyl 4-(1-amino-5-(4-methoxyphenyl)-6-oxo-6,7-dihydro-3H
benzo[f]pyrazolo[3,4-c][2,7]naphthyridin-9-yl)piperazine-1-
carboxylate 3.4 ml (72 mmol) of hydrazine hydrate is added to a solution of 0.4 g (0.7 mmol) of tert-butyl 4-(1-cyano-4-(4-methoxyphenyl)-2-(methylthio)-5-oxo-5,6-dihydrobenzo[c][2,7]naphthyridin-8-yl)piperazine-1-carboxylate dissolved in 6.8 ml of butan-1-ol and 2.7 ml of dimethylsulfoxide. The reaction medium is carried at 150° C. for 12 hours. The precipitate obtained is filtered on Dicalite and then rinsed with dichloromethane. The filtrate is evaporated and then the residue is triturated in water to lead after filtration to 0.26 g (67%) of tert-butyl 4-(1-amino-5-(4-methoxyphenyl)-6-oxo-6,7-dihydro-3H-benzo[f]pyrazolo[3,4-c][2,7]-naphthyridin-9-yl)piperazine-1-carboxylate in the form of a yellow solid.

LCMS (ESI, m/z): (M+1) 542.6

$^1$H NMR: $\delta_H$ pm 400 MHz, DMSO: 12.73 (1H, bs, NH), 11.14 (1H, bs, NH), 8.90 (1H, d, CH$_{arom}$), 7.40 (2H, d, CH$_{arom}$), 7.01 (1H, s, CH$_{arom}$), 6.91 (2H, d, CH$_{arom}$), 6.73 (1H, d, CH$_{arom}$), 5.22 (2H, bs, NH$_2$), 3.80 (3H, m, CH$_3$), 3.33-3.49 (8H, m, 4CH$_2$), 1.43 (9H, s, 3CH$_3$).

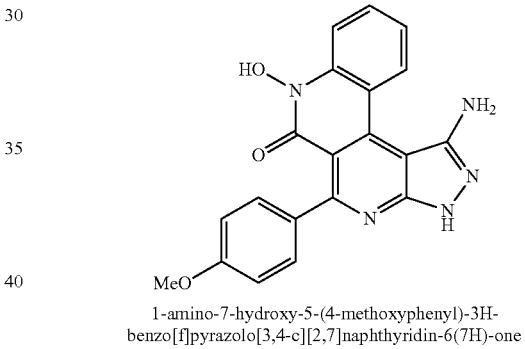

1-amino-7-hydroxy-5-(4-methoxyphenyl)-3H-
benzo[f]pyrazolo[3,4-c][2,7]naphthyridin-6(7H)-one 37.4 ml (770 mmol) of hydrazine hydrate is added to a solution of 3 g (7.7 mmol) of 6-hydroxy-4-(4-methoxyphenyl)-2-(methylthio)-5-oxo-5,6-dihydrobenzo[c][2,7]-naphthyridine-1-carbonitrile dissolved in 80 ml of butan-1-ol and 32 ml of dimethylsulfoxide. The reaction medium is carried at 150° C. for 3 hours and then is allowed to rest at room temperature overnight. The precipitate obtained is filtered and then rinsed with methanol to yield 1.14 g (39%) of 1-amino-7-hydroxy-5-(4-methoxyphenyl)-3H-benzo[f]pyrazolo[3,4-c][2,7]naphthyridin-6(7H)-one in the form of a yellow solid.

LCMS (ESI, m/z): (M+1) 374.2

$^1$H NMR: $\delta_H$ pm 400 MHz, DMSO: 9.15-9.22 (1H, m, CH$_{arom}$), 7.70-7.85 (2H, m, CH$_{arom}$), 7.33-7.51 (3H, m, CH$_{arom}$), 6.94 (2H, d, CH$_{arom}$), 5.36 (2H, bs, NH$_2$), 3.82 (3H, m, CH$_3$).

E) Pathway E: Synthesis of Polycyclic Systems by Formation of Cyclopentadienone Ring A E-1 Synthesis of Precursors

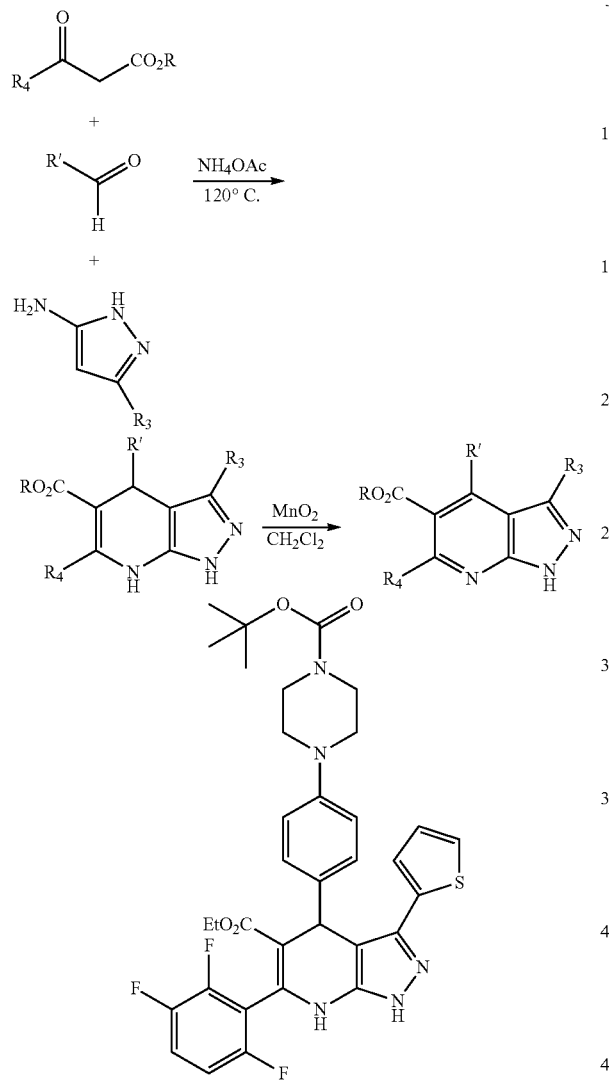

ethyl 4-(4-(4-(tertbutoxycarbonyl)piperazin-1-yl)phenyl)-3-(thiophen-2-yl)-6-(2,3,6-trifluorophenyl)-4,7-dihydro-1H-pyrazolo[3,4-b]pyridine-5-carboxylate 250 mg (1.02 mmol) of ethyl 3-oxo-3-(2,3,6-trifluorophenyl)propanoate, 295 mg (1.02 mmol) of tert-butyl 4-(4-formylphenyl)piperazine-1-carboxylate, 168 mg (1.02 mmol) of 3-(thiophen-2-yl)-1H-pyrazol-5-amine and 196 mg (2.54 mmol) of ammonium acetate are added to a test tube which is then sealed. The mixture is carried without solvent at 120° C. for 1 hour. After returning to room temperature, the solid is dissolved in a water/ethyl acetate mixture. The phases are separated and the aqueous phase is extracted several times with ethyl acetate. The organic phases are combined, dried on magnesium sulfate and concentrated. The residue is purified by silica gel chromatography (eluent: 6:4 cyclohexane/ethyl acetate) to yield 300 mg (44%) of ethyl 4-(4-(4-(tert-butoxycarbonyl)piperazin-1-yl)phenyl)-3-(thiophen-2-yl)-6-(2,3,6-trifluorophenyl)-4,7-dihydro-1H-pyrazolo[3,4-b]pyridine-5-carboxylate in the form of a light yellow powder.

$^1$H NMR: $\delta_H$ pm 400 MHz, DMSO: 12.68 (1H, bs, NH), 9.95 (1H, d, NH), 7.46-7.67 (2H, m, CH$_{arom}$), 7.27-7.35 (1H, m, CH$_{arom}$), 7.06-7.20 (4H, m, CH$_{arom}$), 6.78 (2H, dd, CH$_{arom}$), 5.26 (1H, d, CH), 3.66-3.84 (2H, m, CH$_2$), 3.35-3.44 (4H, m, 2CH$_2$), 2.96-3.08 (4H, m, 2CH$_2$), 1.40 (9H, s, 3CH$_3$), 0.85 (3H, t, CH$_3$).

ethyl 4-(4-(4-(tert-butoxycarbonyl)piperazin-1-yl)phenyl)-3-(thiophen-2-yl)-6-(2,3,6-trifluorophenyl)-1H-pyrazolo[3,4-b]pyridine-5-carboxylate 254 mg (2.93 mmol) of manganese oxide is added to 300 mg (0.45 mmol) of ethyl 4-(4-(4-(tert-butoxycarbonyl)piperazin-1-yl)phenyl)-3-(thiophen-2-yl)-6-(2,3,6-trifluorophenyl)-4,7-dihydro-1H-pyrazolo[3,4-b]pyridine-5-carboxylate in solution in 10 ml of dichloromethane. The reaction mixture is placed in an ultrasonic bath for 5 minutes and then stirred at room temperature for 20 hours. It is then filtered on silica (eluent: 65:35 cyclohexane/ethyl acetate) to yield 254 mg (85%) of ethyl 4-(4-(4-(tert-butoxycarbonyl)piperazin-1-yl)phenyl)-3-(thiophen-2-yl)-6-(2,3,6-trifluorophenyl)-1H-pyrazolo[3,4-b]pyridine-5-carboxylate in the form of a yellow solid.

LCMS (ESI, m/z): (M+1) 664.1

$^1$H NMR: $\delta_H$ pm 400 MHz, DMSO: 14.36 (1H, bs, NH), 7.63-7.76 (1H, m, CH$_{arom}$), 7.41-7.48 (1H, m, CH$_{arom}$), 7.27-7.37 (1H, m, CH$_{arom}$), 7.10 (2H, d, CH$_{arom}$), 6.89 (2H, d, CH$_{arom}$), 5.90-5.99 (1H, m, CH$_{arom}$), 3.79 (2H, q, CH$_2$), 3.41-3.52 (4H, m, 2CH$_2$), 3.10-3.22 (4H, m, 2CH$_2$), 1.43 (9H, s, 3CH$_3$), 0.72 (3H, t, CH$_3$).

The compound below is obtained according to procedure E1

E-2 Synthesis of Polycyclic Systems
Procedure E2a:

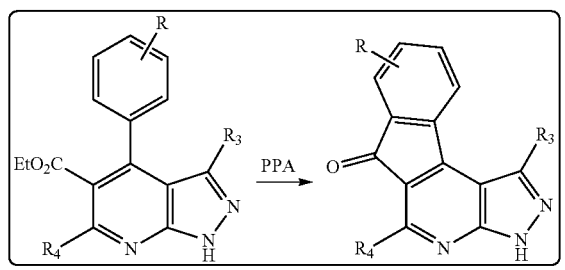

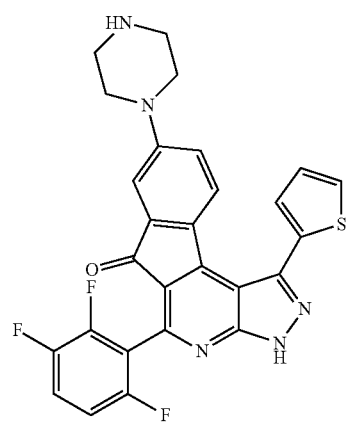

8-(piperazin-1-yl)-1-(thiophen-2-yl)-5-(2,3,6-trifluorophenyl)indeno[1,2-d]pyrazolo[3,4-b]pyridin-6(3H)-one8-(piperazin-1-yl)-1-(thiophen-2-yl)-5-(2,3,6-trifluorophenyl)indeno[1,2-d]pyrazolo[3,4-b]pyridin-6(3H)-one 10 g of polyphosphoric acid is added to a solution of 2 g (3 mmol) of ethyl 4-(4-(4-(tert-butoxycarbonyl)piperazin-1-yl)phenyl)-3-(thiophen-2-yl)-6-(2,3,6-trifluorophenyl)-4,7-dihydro-1H-pyrazolo[3,4-b]pyridine-5-carboxylate in xylene (20 ml). The reaction mixture is carried at 160° C. for 36 hours. After returning to room temperature, the reaction medium is poured over crushed ice. Saturated sodium bicarbonate solution is added until the reaction medium is neutralized and then the product is extracted with ethyl acetate. The organic phases are combined, dried on magnesium sulfate and concentrated. The residue is purified by silica gel chromatography (eluent: 88:12 dichloromethane/methanol) to yield 50 mg (3%) of 8-(piperazin-1-yl)-1-(thiophen-2-yl)-5-(2,3,6-trifluorophenyl)indeno[1,2-d]pyrazolo[3,4-b]pyridin-6(3H)-one in the form of a pinkish solid.

LCMS (ESI, m/z): (M+1) 518.3

$^1$H NMR: $\delta_H$ pm 500 MHz, DMSO: 7.88-7.93 (1H, m, $CH_{arom}$), 7.67-7.79 (1H, m, $CH_{arom}$), 7.44-7.50 (1H, m, $CH_{arom}$), 7.27-7.39 (2H, m, $CH_{arom}$), 7.09-7.15 (1H, m, $CH_{arom}$), 6.76-6.84 (1H, m, $CH_{arom}$), 6.33-6.41 (1H, m, $CH_{arom}$), 3.26-3.35 (4H, m, $2CH_2$), 2.79-2.91 (4H, m, $2CH_2$).

Procedure E2b:

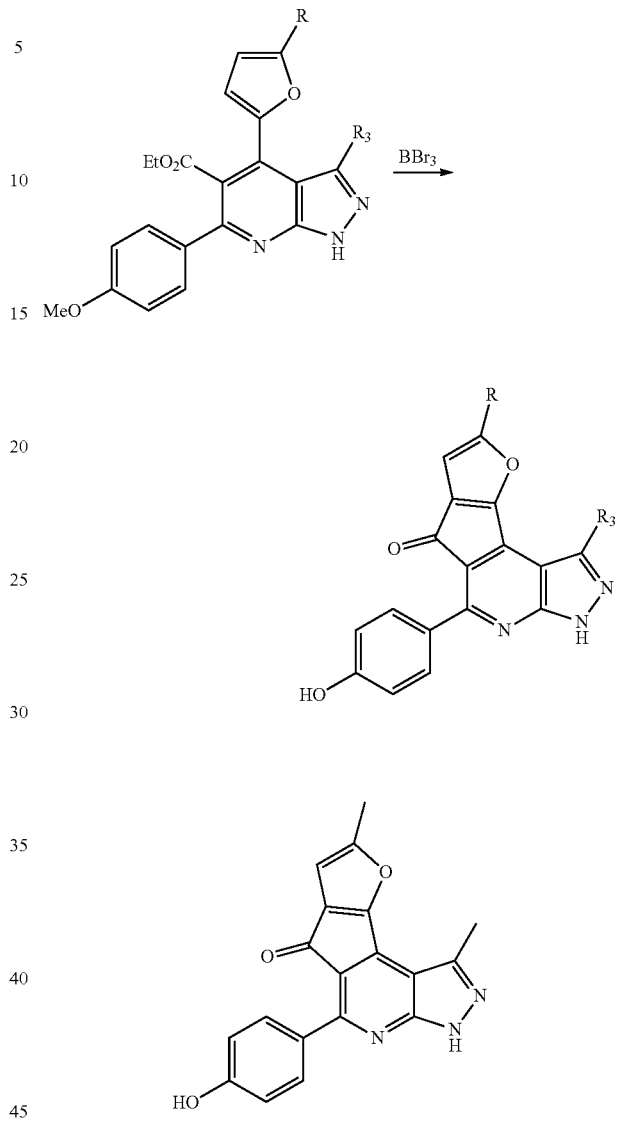

175 µl (1.81 mmol) of boron tribromide is added to a solution of 142 mg (0.36 mmol) of ethyl 6-(4-methoxyphenyl)-3-methyl-4-(5-methylfuran-2-yl)-1H-pyrazolo[3,4-b]pyridine-5-carboxylate in dichloromethane (10 ml) at −78° C. The reaction mixture is stirred for 1 hour at −78° C., then 1 hour at room temperature and then 17 hours at 50° C. At −78° C., 10 ml of methanol is then added and the mixture is then concentrated under reduced pressure. The residue is purified by silica gel chromatography (elution gradient: 0% to 20% MeOH in dichloromethane) and then by semi-preparative HPLC to yield 1.7 mg of cyclized product in the form of an orange solid.

LCMS (ESI, m/z): (M+1) 332.2

$^1$H NMR: $\delta_H$ pm 500 MHz, DMSO: 7.52 (2H, d, $CH_{arom}$), 6.80 (2H, d, $CH_{arom}$), 6.41 (1H, s, $CH_{arom}$), 2.61 (3H, s, $CH_3$), 2.43 (3H, s, $CH_3$).

F) Peripheral Modifications of the Structure
F-1 Intermediate Protections

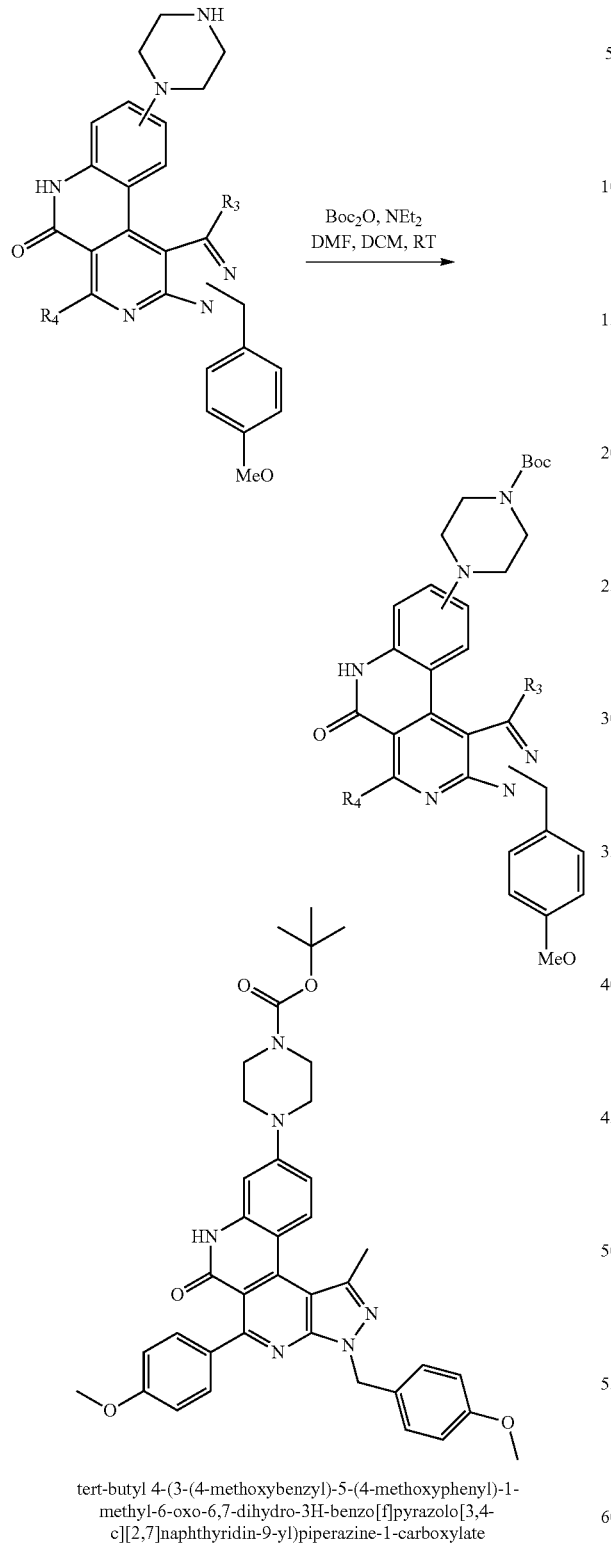

tert-butyl 4-(3-(4-methoxybenzyl)-5-(4-methoxyphenyl)-1-methyl-6-oxo-6,7-dihydro-3H-benzo[f]pyrazolo[3,4-c][2,7]naphthyridin-9-yl)piperazine-1-carboxylate 1.63 g (7.49 mmol) of di-tert-butyl dicarbonate and 2.6 ml (18.73 mmol) of triethylamine are added respectively to 3.5 g (6.24 mmol) of 3-(4-methoxybenzyl)-5-(4-methoxyphenyl)-1-methyl-9-(piperazin-1-yl)-3H-benzo[f]pyrazolo[3,4-c][2,7]naphthyridin-6(7H)-one dissolved in 60 ml of dichloromethane and 20 ml of dimethylformamide. The reaction mixture is stirred at room temperature for 2 hours. The solvents are evaporated, water is added and then the product is extracted several times with ethyl acetate. The organic phases are combined, washed with 1 N hydrochloric acid solution and then with saturated sodium chloride solution, dried on magnesium sulfate and concentrated. The residue is triturated in a methanol/diethyl ether mixture to lead after filtration to 2.3 g (55%) of tert-butyl 4-(3-(4-methoxybenzyl)-5-(4-methoxyphenyl)-1-methyl-6-oxo-6,7-dihydro-3H-benzo[f]pyrazolo[3,4-c][2,7]naphthyridin-9-yl)piperazine-1-carboxylate in the form of a yellow solid.

LCMS (ESI, m/z): (M+1) 661.4

$^1$H NMR: $\delta_H$ pm 400 MHz, DMSO: 11.27 (1H, bs, NH), 8.17 (1H, d, $CH_{arom}$), 7.51 (2H, d, $CH_{arom}$), 7.28 (2H, d, $CH_{arom}$), 6.92-7.01 (3H, m, $CH_{arom}$), 6.88 (2H, d, $CH_{arom}$), 6.72-6.78 (1H, m, $CH_{arom}$), 5.56 (2H, s, $CH_2$), 3.82 (3H, s, $CH_3$), 3.70 (3H, s, $CH_3$), 3.44-3.55 (4H, m, $2CH_2$), 3.30-3.40 (4H, m, $2CH_2$), 2.73 (3H, s, $CH_3$), 1.43 (9H, s, $3CH_3$).

F-2 Alkylation of Pyridone Ring A
F-2a General Case

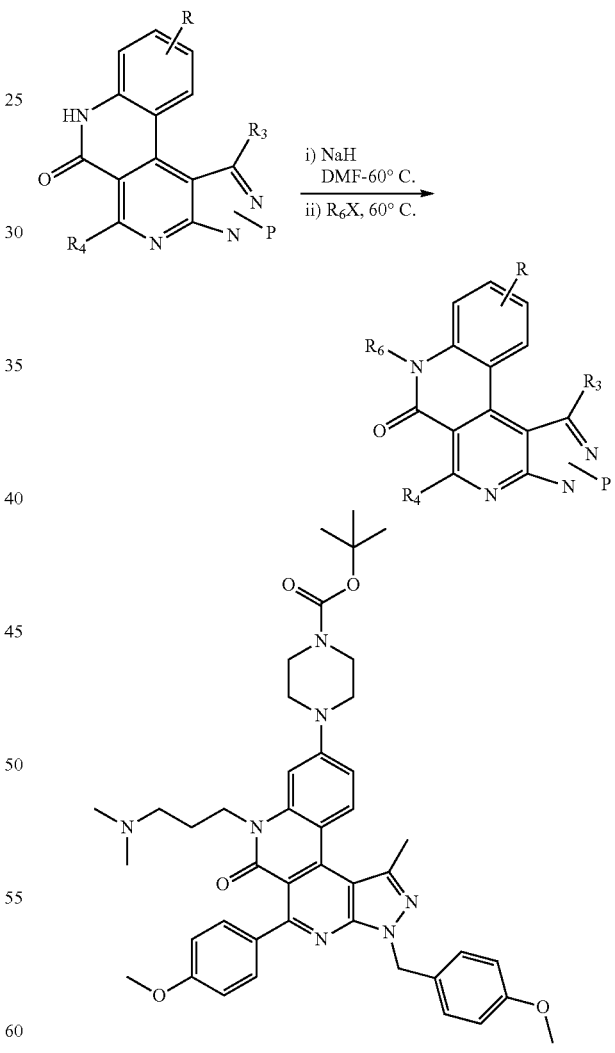

tert-butyl 4-(7-(3-(dimethylamino)propyl)-3-(4-methoxybenzyl)-5-(4-methoxyphenyl)-1-methyl-6-oxo-6,7-dihydro-3H-benzo[f]pyrazolo[3,4-c][2,7]naphthyridin-9-yl)piperazine-1-carboxylate 580 mg (14.53 mmol) of sodium hydride 60% dispersion in oil is added to 1.6 g (2.42 mmol) of the mixture of tert-butyl 4-(3-(4-methoxybenzyl)-5-(4-methoxyphenyl)-1-methyl-6-oxo-6,7-dihydro-3H-benzo[f]pyrazolo[3,4-c][2,7]naphthyridin-9-yl) piperazine-1-carboxylate and tert-butyl 4-(2-(4-methoxybenzyl)-5-(4-methoxyphenyl)-1-methyl-6-oxo-6,7-dihydro-3H-benzo pyrazolo[3,4-c][2,7]naphthyridin-9-yl) piperazine-1-carboxylate dissolved in 50 ml of anhydrous dimethylformamide. The reaction medium is carried at 60° C. for 30 minutes before the addition of a solution of 957 mg (6.05 mmol) of 3-chloro-N,N-dimethylpropan-1-amine hydrochloride in 5 ml of dimethylformamide. The reaction mixture is stirred at 60° C. for additional 4 hours. After returning to room temperature, water is added and then the product is extracted several times with ethyl acetate. The organic phases are combined, washed with saturated sodium chloride solution, dried on magnesium sulfate and concentrated. The residue is purified by silica gel chromatography (eluent: 9:1 dichloromethane/methanol) to yield 1.06 g (58%) of the mixture of tert-butyl 4-(7-(3-(dimethylamino)propyl-3-(4-methoxybenzyl)-5-(4-methoxyphenyl)-1-methyl-6-oxo-6,7-dihydro-3H-benzo[/]pyrazolo[3,4-c][2,7]naphthyridin-9-yl)piperazine-1-carboxylate and tert-butyl 4-(7-(3-(dimethylamino)propyl-2-(4-methoxybenzyl)-5-(4-methoxyphenyl)-1-methyl-6-oxo-6,7-dihydro-3H-benzo[f]pyrazolo[3,4-c][2,7]naphthyridin-9-yl)piperazine-1-carboxylate in the form of a yellow solid.

LCMS (ESI, m/z): (M+1) 746.5

$^1$H NMR of the major product: $\delta_H$ pm 400 MHz, DMSO: 8.18 (1H, d, $CH_{arom}$), 7.50 (2H, d, $CH_{arom}$), 7.28 (2H, d, $CH_{arom}$), 7.00-7.07 (1H, m, $CH_{arom}$), 6.85-6.97 (5H, m, $CH_{arom}$), 5.56 (2H, s, $CH_2$), 4.17-4.25 (2H, m, $CH_2$), 3.82 (3H, s, $CH_3$), 3.70 (3H, s, $CH_3$), 3.49-3.57 (4H, m, $2CH_2$), 3.39-3.47 (4H, m, $2CH_2$), 2.70 (3H, s, $CH_3$), 2.23-2.36 (2H, m, $CH_2$), 2.14 (6H, s, $2CH_3$), 1.66-1.78 (2H, m, $CH_2$), 1.43 (9H, s, $3CH_3$).

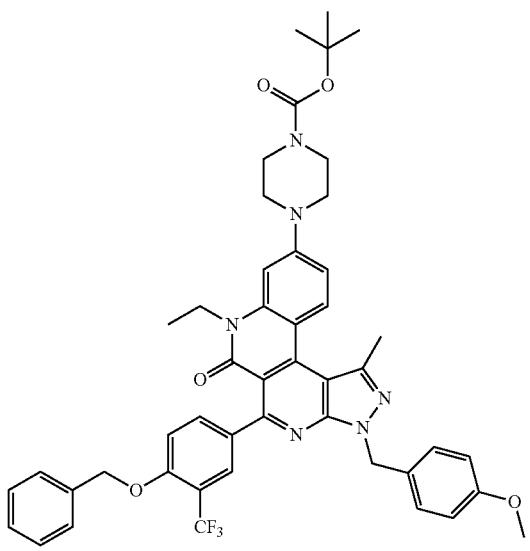

tert-butyl 4-(5-(4-(benzyloxy)-3-(trifluoromethyl)phenyl)-7-ethyl-3-(4-methoxybenzyl)-1-methyl-6-oxo-6,7-dihydro-3H-benzo[f]pyrazolo[3,4-c][2,7]naphthyridin-9-yl)piperazine-1-carboxylate

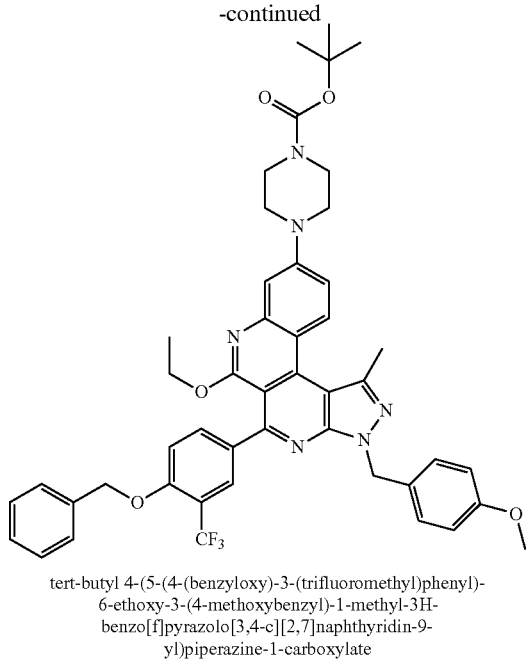

tert-butyl 4-(5-(4-(benzyloxy)-3-(trifluoromethyl)phenyl)-6-ethoxy-3-(4-methoxybenzyl)-1-methyl-3H-benzo[f]pyrazolo[3,4-c][2,7]naphthyridin-9-yl)piperazine-1-carboxylate 392 mg (9.81 mmol) of sodium hydride 60% dispersion in oil is added to 2.63 g (3.27 mmol) of the mixture of tert-butyl 4-(5-(4-benzyloxy)-3-(trifluoromethyl)phenyl)-3-(4-methoxybenzyl)-1-methyl-6-oxo-6,7-dihydro-3H-benzo[f]pyrazolo[3,4-c][2,7]naphthyridin-9-yl)piperazine-1-carboxylate and tert-butyl 4-(2-(4-methoxybenzyl)-5-(4-methoxyphenyl)-1-methyl-6-oxo-6,7-dihydro-3H-benzo[f]pyrazolo[3,4-c][2,7]naphthyridin-9-yl)piperazine-1-carboxylate dissolved in 60 ml of anhydrous dimethylformamide. The reaction medium is carried at 60° C. for 30 minutes before the addition of 445 µl (5.56 mmol) of ethyl iodide solution. The reaction mixture is stirred at 60° C. for additional 3 hours. After returning to room temperature, water is added and then the product is extracted several times with ethyl acetate. The organic phases are combined, washed with saturated sodium chloride solution, dried on magnesium sulfate and concentrated. The residue is purified by silica gel chromatography (eluent: 65:45 cyclohexane/ethyl acetate) to yield 1.1 g (40%) of tert-butyl 4-(5-(4-benzyloxy)-3-(trifluoromethyl)phenyl)-7-ethyl-3-(4-methoxybenzyl)-1-methyl-6-oxo-6,7-dihydro-3H-benzo[f]pyrazolo[3,4-c][2,7]naphthyridin-9-yl)piperazine-1-carboxylate in the form of a yellow solid and 427 mg (16%) of tert-butyl 4-(5-(4-benzyloxy)-3-(trifluoromethyl)phenyl)-6-ethoxy-3-(4-methoxybenzyl)-1-methyl-3H-benzo[f]pyrazolo[3,4-c][2,7]naphthyridin-9-yl)piperazine-1-carboxylate in the form of a yellow solid. tert-butyl 4-(5-(4-benzyloxy)-3-(trifluoromethyl)phenyl)-7-ethyl-3-(4-methoxybenzyl)-1-methyl-6-oxo-6,7-dihydro-3H-benzo[f]pyrazolo[3,4-c][2,7]naphthyridin-9-yl) piperazine-1-carboxylate LCMS (ESI, m/z): (M+1) 833.6

$^1$H NMR: $\delta_H$ pm 400 MHz, DMSO: 8.21 (1H, d, $CH_{arom}$), 7.75-7.84 (2H, m, $CH_{arom}$), 7.33-7.65 (6H, m, $CH_{arom}$), 7.29 (2H, d, $CH_{arom}$), 7.08 (1H, dd, $CH_{arom}$), 6.85-6.91 (3H, m, $CH_{arom}$), 5.58 (2H, s, $CH_2$), 5.37 (2H, s, $CH_2$), 4.20-4.30 (2H, m, $CH_2$), 3.71 (3H, s, $CH_3$), 3.44-3.56 (8H, m, $4CH_2$), 2.73 (3H, s, $CH_3$), 1.45 (9H, s, $3CH_3$), 1.21 (3H, t, $CH_3$).

tert-butyl 4-(5-(4-benzyloxy)-3-(trifluoromethyl)phenyl)-6-ethoxy-3-(4-methoxybenzyl)-1-methyl-3H-benzo[f]pyrazolo[3,4-c][2,7]naphthyridin-9-yl)piperazine-1-carboxylate LCMS (ESI, m/z): (M+1) 833.6

¹H NMR: δ_H pm 400 MHz, DMSO: 8.51 (1H, d, CH_arom), 7.81 (1H, dd, CH_arom), 7.72-7.76 (1H, m, CH_arom), 7.25-7.63 (9H, m, CH_arom), 7.10-7.14 (1H, m, CH_arom), 6.88 (2H, d, CH_arom), 5.61 (2H, s, CH₂), 5.42 (2H, s, CH₂), 4.19 (2H, q, CH₂), 3.70 (3H, s, CH₃), 3.48-3.55 (4H, m, 2CH₂), 3.39-3.45 (4H, m, 2CH₂), 2.85 (3H, s, CH₃), 1.45 (9H, s, 3CH₃), 0.79 (3H, t, CH₃).

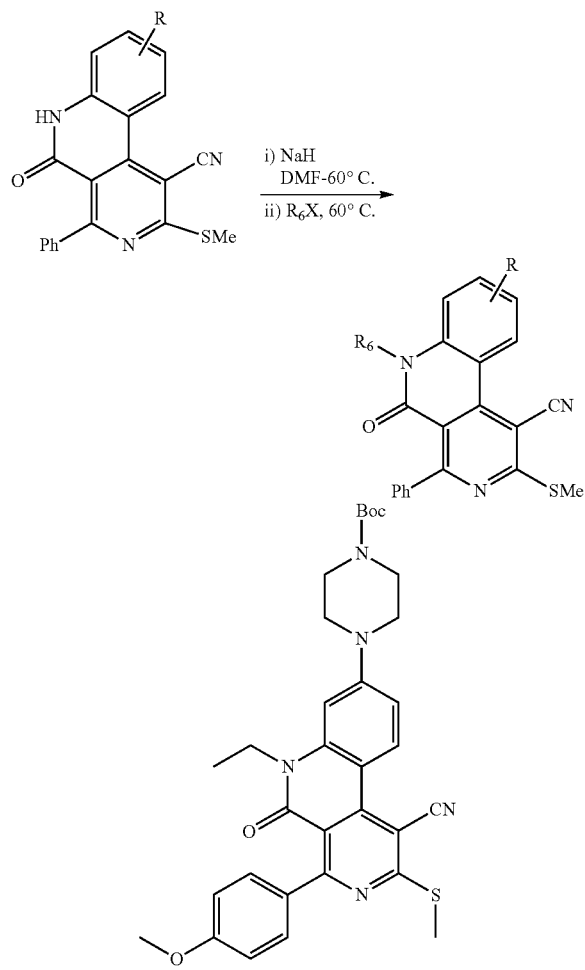

tert-butyl 4-(1-cyano-6-ethyl-4-(4-methoxyphenyl)-2-(methylthio)-5-oxo-5,6-dihydrobenzo[c][2,7]naphthyridin-8-yl)piperazine-1-carboxylate 75 mg (1.86 mmol) of sodium hydride 60% dispersion in oil is added to 0.52 g (1.93 mmol) of tert-butyl 4-(1-cyano-4-(4-methoxyphenyl)-2-(methylthio)-5-oxo-5,6-dihydrobenzo[c][2,7]naphthyridin-8-yl)piperazine-1-carboxylate dissolved in 14 ml of tetrahydrofuran and 17 ml of anhydrous dimethylformamide. The reaction medium is carried at 60° C. for 45 minutes before the addition of 127 μl (1.86 mmol) of hot iodoethane solution. The reaction mixture is stirred at 60° C. for additional 25 minutes. After returning to room temperature, water is added and then the product is extracted several times with ethyl acetate. The organic phases are combined, washed with saturated sodium chloride solution, dried on magnesium sulfate and concentrated. The residue is purified by silica gel chromatography (eluent: 7:3 cyclohexane/ethyl acetate) to yield 130 mg (24%) of tert-butyl 4-(1-cyano-5-ethoxy-4-(4-methoxyphenyl)-2-(meth-ylthio)benzo[c][2,7]naphthyridin-8-yl)piperazine-1-carboxylate in the form of a yellow solid and 360 mg (56%) of tert-butyl 4-(1-cyano-6-ethyl-4-(4-methoxyphenyl)-2-(methylthio)-5-oxo-5,6-dihydrobenzo[c][2,7]naphthyridin-8-yl)piperazine-1-carboxylate in the form of a yellow solid.

LCMS (ESI, m/z): (M+1) 586.72

¹H NMR of the majority product: δ_H pm 400 MHz, DMSO: 8.86 (1H, d, CH_arom), 7.56 (2H, d, CH_arom), 7.05 (1H, d, CH_arom), 6.97 (2H, d, CH_arom), 6.79 (1H, d, CH_arom), 4.24 (2H, q, CH₂), 3.83 (3H, s, CH₃), 3.45-3.49 (8H, m, 4CH₂), 2.65 (3H, s, CH₃), 1.43 (9H, s, 3CH₃), 1.17 (3H, t, CH₃).

F-2b Specific Case

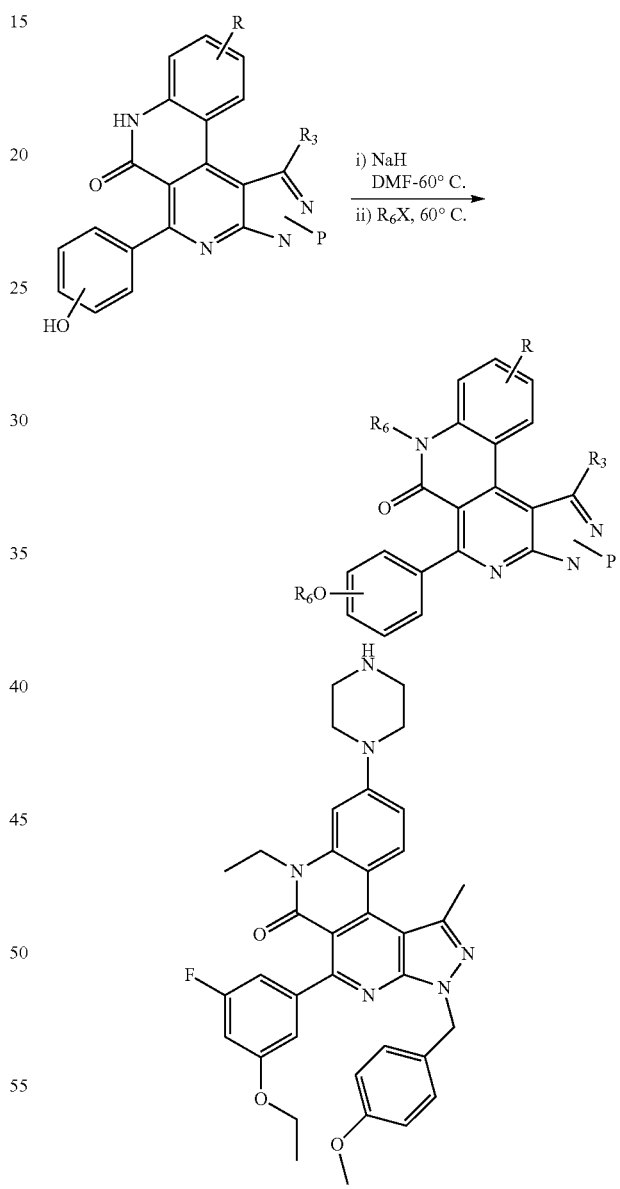

5-(3-ethoxy-5-fluorophenyl)-7-ethyl-3-(4-methoxybenzyl)-1-methyl-9-(piperazin-1-yl)-3H-benzo[f]pyrazolo[3,4-c][2,7]naphthyridin-6(7H)-one 756 mg (18.85 mmol) of sodium hydride 60% dispersion in oil is added to 1.8 g (2.7 mmol) of 5-(5-fluoro-3-hydroxyphenyl)-3-(4-methoxybenzyl)-1-methyl-9-(piperazin-1-yl)-3H-benzo[f]pyrazolo[3,4-c][2,7]naphthyridin-6(7H)-one dissolved in 40 ml of anhydrous dimethylformamide. The reaction medium is carried at 60° C. for 30 minutes before the addition of 515 µl (5.4 mmol) of ethyl iodide solution. The reaction mixture is stirred at 60° C. for additional 4 hours. After returning to room temperature, water is added and then the product is extracted several times with ethyl acetate. The organic phases are combined, washed with saturated sodium chloride solution, dried on magnesium sulfate and concentrated. The residue is purified by silica gel chromatography (eluent: dichloromethane and then 98:2 dichloromethane/methanol) to yield 1.2 g (61%) of 5-(3-ethoxy-5-fluorophenyl)-7-ethyl-3-(4-methoxybenzyl)-1-methyl-9-(piperazin-1-yl)-3H-benzo[f]pyrazolo[3,4-c][2,7]naphthyridin-6(7H)-one in the form of a brown solid.

LCMS (ESI, m/z): (M+1) 721.5

$^1$H NMR of the major product: $\delta_H$ pm 400 MHz, DMSO: 8.20 (1H, d, $CH_{arom}$), 7.22-7.34 (3H, m, $CH_{arom}$), 7.02-7.09 (1H, m, $CH_{arom}$), 6.79-6.95 (5H, m, $CH_{arom}$), 5.55 (2H, s, $CH_2$), 4.15-4.18 (2H, m, $CH_2$), 4.01-4.12 (2H, m, $CH_2$), 3.70 (3H, s, $CH_3$), 3.49-3.57 (4H, m, $2CH_2$), 3.43-3.47 (4H, m, $2CH_2$), 2.71 (3H, s, $CH_3$), 1.43 (9H, s, $3CH_3$), 1.18 (3H, t, $CH_3$).

F-3 Reduction of Pyridone Ring A of 3-(4-methoxybenzyl)-5-(4-methoxyphenyl)-1-methyl-3H-benzo[f]pyrazolo[3,4-c][2,7]naphthyridin-6(7H)-one dissolved in 15 ml of tetrahydrofuran is added. The reaction medium is carried at 60° C. for 4 hours before returning to room temperature. The reaction is hydrolyzed by the slow addition of 9:1 tetrahydrofuran/water solution and then water. The product is extracted with ethyl acetate. The organic phases are dried on magnesium sulfate and concentrated. The residue is triturated in acetonitrile and then the solid is filtered. The filtrate is evaporated and then triturated again in acetonitrile. Filtration of the latter trituration leads to 350 mg (36%) of 3-(4-methoxybenzyl)-5-(4-methoxyphenyl)-1-methyl-6,7-dihydro-3H-benzo[f]pyrazolo[3,4-c][2,7]naphthyridine in the form of a yellow solid.

LCMS (ESI, m/z): (M+1) 463.2

$^1$H NMR: $\delta_H$ pm 400 MHz, DMSO: 7.79 (1H, d, $CH_{arom}$), 7.57 (2H, d, $CH_{arom}$), 7.21-7.27 (3H, m, $CH_{arom}$), 7.09 (2H, d, $CH_{arom}$), 6.83-6.93 (4H, m, $CH_{arom}$), 6.07 (1H, bs, NH), 5.53 (2H, s, $CH_2$), 4.20 (2H, s, $CH_2$), 3.85 (3H, s, $CH_3$), 3.70 (3H, s, $CH_3$), 2.55 (3H, s, $CH_3$).

F-4 Esterification of the Phenol

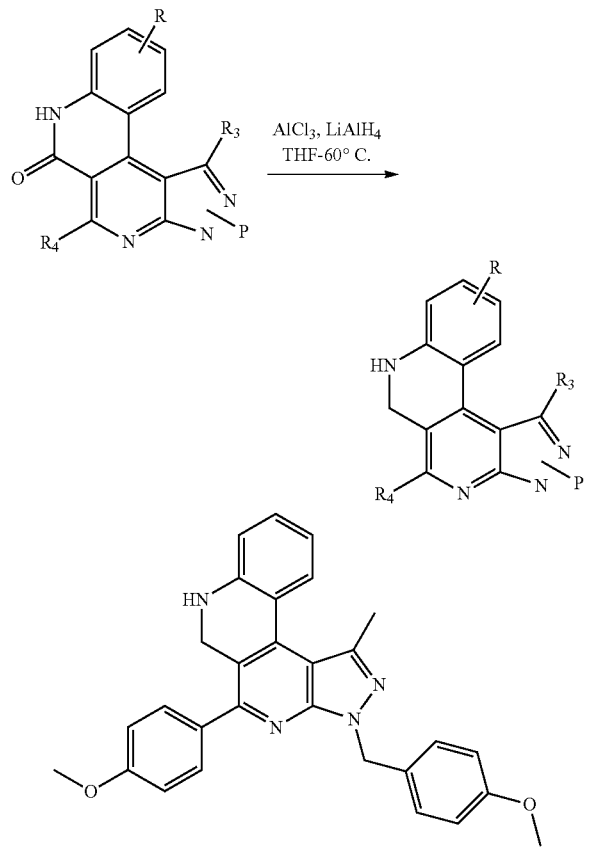

3-(4-methoxybenzyl)-5-(4-methoxyphenyl)-1-methyl-6,7-dihydro-3H-benzo[f]pyrazolo[3,4-c][2,7]naphthyridine A solution of 280 mg (2.1 mmol) of aluminum trichloride in 10 ml of tetrahydrofuran is added to 160 mg (4.2 mmol) of lithium aluminum hydride dissolved in 10 ml of anhydrous tetrahydrofuran. The reaction medium is stirred at room temperature for 30 minutes and then a solution of 1 g (2.1 mmol)

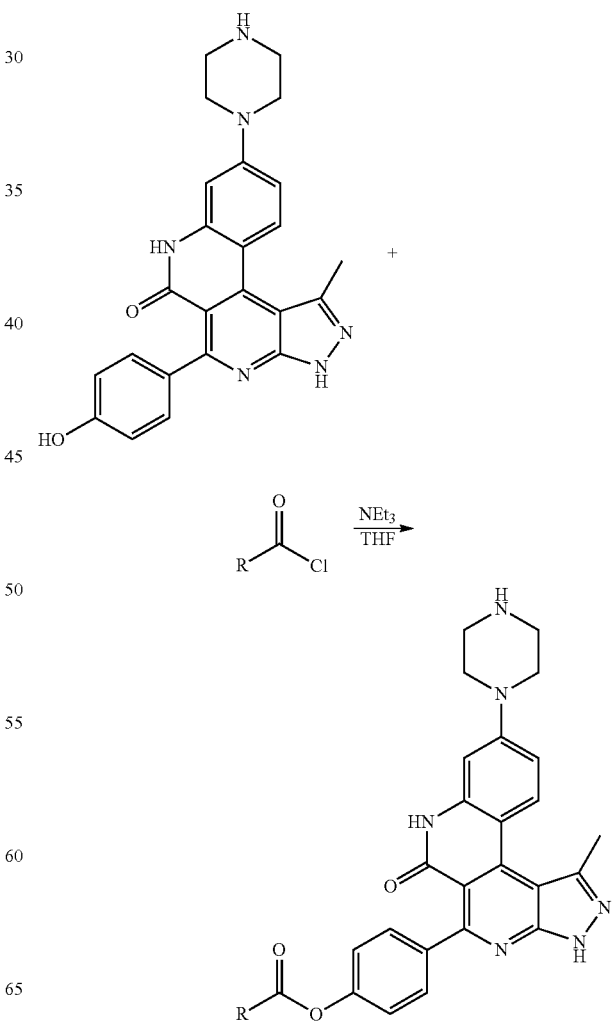

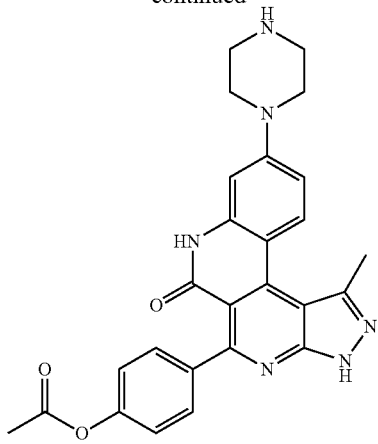

4-(1-methyl-6-oxo-9-(piperazin-1-yl)-6,7-dihydro-3H-benzo[f]pyrazolo[3,4-c][2,7]naphthyridin-5-yl) phenyl acetate

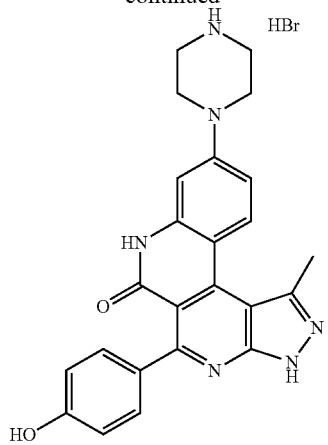

Bromohydrate de 5-(4-hydroxyphenyl)-1-methyl-9-(piperazin-1-yl)-3H-benzo[f]pyrazolo[3,4-c][2,7]naphthyridin-6(7H)-one 132 µl (1.84 mmol, 145 mg) of acetyl chloride is added in several portions to a suspension of 602 mg (1.18 mmol) of 5-(4-hydroxyphenyl)-1-methyl-9-(piperazin-1-yl)-3H-benzo[f]pyrazolo[3,4-c][2,7]naphthyridin-6(7H)-one hydrobromide in 120 ml of THF at 0° C. The mixture is then stirred for 48 hours at room temperature and then concentrated under reduced pressure. The residue is purified by reverse-phase preparative HPLC to yield 51 mg (8%) of 4-(1-methyl-6-oxo-9-(piperazin-1-yl)-6,7-dihydro-3H-benzo[f]pyrazolo[3,4-c][2,7]naphthyridin-5-yl)phenyl acetate in the form of a yellow solid.

LCMS (ESI, m/z): (M+1) 469.26

$^1$H NMR: $\delta_H$ pm 400 MHz, DMSO: 13.63 (1H, bs, NH), 11.26 (1H, s, NH), 8.43 (2H, bs, NH.HCO$_2$H), 8.20 (1H, d, CH$_{arom}$), 7.34 (2H, d, CH$_{arom}$), 7.02 (1H, dd, CH$_{arom}$), 6.73-6.77 (1H, m, CH$_{arom}$), 6.75 (2H, d, CH$_{arom}$), 3.60-3.70 (4H, m, 2CH$_2$), 3.35-3.45 (4H, m, 2CH$_2$), 2.76 (3H, s, CH$_3$), 2.08 (3H, s, CH$_3$).

G) Deprotection Techniques

G1—Deprotection of the Pyrrole and the Phenol when the Latter is Protected by a Methoxy G-1a General Case

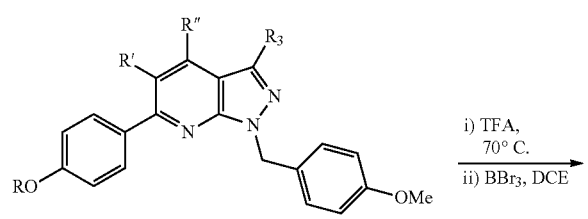

A solution of 4.5 g (8.03 mmol) of 3-(4-methoxybenzyl)-5-(4-methoxyphenyl)-1-methyl-9-(piperazin-1-yl)-3H-benzo[f]pyrazolo[3,4-c][2,7]naphthyridin-6(7H)-one dissolved in 70 ml of trifluoroacetic acid is carried at 70° C. for 4 hours and then cooled to room temperature before the addition of isopropyl ether (150 ml). The reaction medium is stirred at room temperature for 30 minutes and then the precipitate obtained is filtered to yield 5-(4-methoxyphenyl)-1-methyl-9-(piperazin-1-yl)-3H-benzo[f]pyrazolo[3,4-c][2,7]naphthyridin-6(7H)-one trifluoroacetate. The solid is dissolved in 180 ml of anhydrous dichloroethane. The reaction medium is cooled to 0° C. before the slow addition of 43.3 ml (43.3 mmol) of a 1 M solution of boron tribromide in dichloromethane. The reaction medium is carried at reflux for 7 hours and then cooled again to 0° C. Methanol (approximately 200 ml) is added and then the reaction medium is stirred for 2 hours. The solid obtained is filtered and then triturated several times in hot methanol. A final filtration yields 2.6 g (47%) of 5-(4-hydroxyphenyl)-1-methyl-9-(piperazin-1-yl)-3H-benzo[f]pyrazolo[3,4-c][2,7]naphthyridin-6(7H)-one hydrobromide in the form of an orange solid.

LCMS (ESI, m/z): (M+1) 427.18

$^1$H NMR: $\delta_H$ pm 400 MHz, DMSO: 11.32 (1H, bs, NH), 8.83 (2H, bs, NH.HBr), 8.22 (1H, d, CH$_{arom}$), 7.36 (2H, d, CH$_{arom}$), 7.00-7.11 (1H, m, CH$_{arom}$), 6.70-6.86 (3H, m, CH$_{arom}$), 3.51-3.61 (4H, m, 2CH$_2$), 3.23-3.37 (4H, m, 2CH$_2$), 2.77 (3H, s, CH$_3$).

G-1b Specific Cases

During this deprotection step, secondary reactions can take place. For example, the following products are obtained:

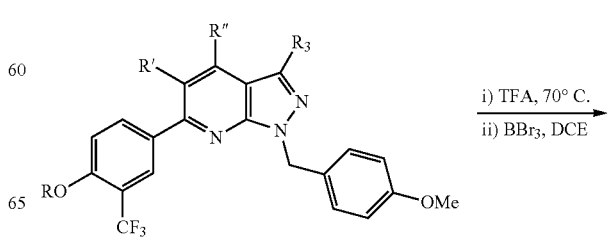

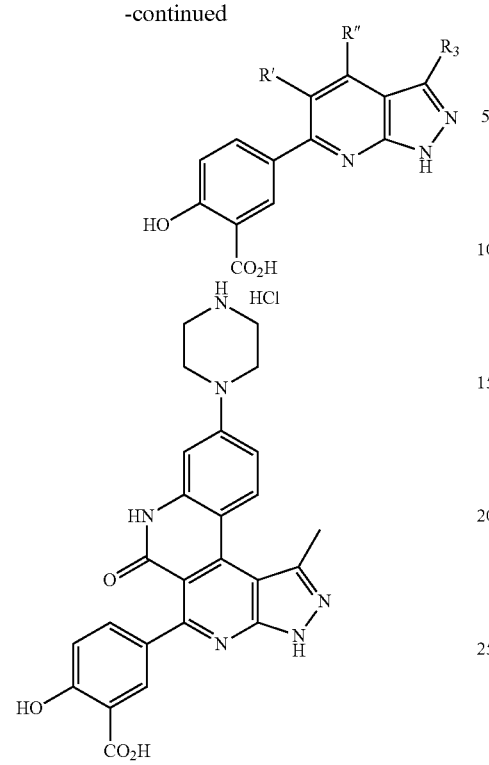

2-hydroxy-5-(1-methyl-6-oxo-9-(piperazin-1-yl)-6,7-dihydro-3H-benzo[f]pyrazolo[3,4-c][2,7]naphthyridin-5-yl)benzoic acid hydrochloride A solution of 3 g (4.77 mmol) of 5-(4-methoxy-3-(trifluoromethyl)phenyl)-3-(4-methoxybenzyl)-1-methyl-9-(piperazin-1-yl)-3H-benzo[f]pyrazolo[3,4-c][2,7]naphthyridin-6(7H)-one dissolved in 25 ml of trifluoroacetic acid is carried at 70° C. for 4 hours and then cooled to room temperature before the addition of isopropyl ether (50 ml). The reaction medium is stirred at room temperature for 30 minutes and then the precipitate obtained is filtered to yield 5-(4-methoxyphenyl)-1-methyl-9-(piperazin-1-yl)-3H-benzo[f]pyrazolo[3,4-c][2,7]naphthyridin-6(7H)-one trifluoroacetate. The solid is dissolved in 40 ml of anhydrous dichloroethane. The reaction medium is cooled to 0° C. before the slow addition of 30.3 ml (30.3 mmol) of a 1 M solution of boron tribromide in dichloromethane. The reaction medium is carried at reflux for 20 hours with the regular addition of a cold 1 M solution of boron tribromide in dichloromethane (30.3 ml, 30.3 mmol additional in total) until the reaction is quenched. Methanol (roughly 100 ml) is added and then the reaction medium is stirred for 2 hours. The solvents are concentrated. Saturated aqueous $NaHCO_3$ solution is added and the aqueous phase is washed with ethyl acetate. The aqueous phase is evaporated and then purified by silica gel chromatography (eluent: 60:14:24:2 dichloromethane/methanol/cyclohexane/ammonium hydroxide to pure methanol) to yield 150 mg (12.5%) of 2-hydroxy-5-(1-methyl-6-oxo-9-(piperazin-1-yl)-6,7-dihydro-3H-benzo[f]pyrazolo[3,4-c][2,7]naphthyridin-5-yl)benzoic acid hydrochloride in the form of a yellow solid.

LCMS (ESI, m/z): (M+1) 471.19

$^1$H NMR: $\delta_H$ pm 400 MHz, DMSO: 11.30-11.50 (2H, m, NH and OH), 9.27 (2H, bs, NH.HCl), 8.25 (1H, d, $CH_{arom}$), 7.99 (1H, s, $CH_{arom}$), 7.66 (1H, d, $CH_{arom}$), 7.03-7.10 (1H, m, $CH_{arom}$), 6.94 (1H, d, $CH_{arom}$), 6.80-6.85 (1H, m, $CH_{arom}$), 3.52-3.62 (4H, m, $2CH_2$), 3.21-3.32 (4H, m, $2CH_2$), 2.78 (3H, s, $CH_3$).

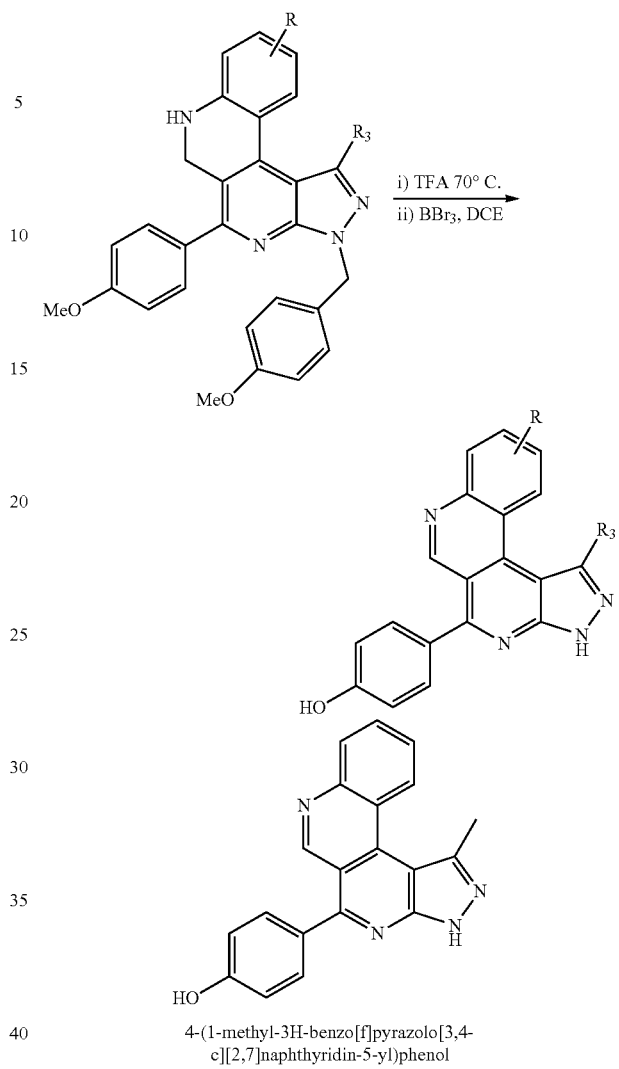

4-(1-methyl-3H-benzo[f]pyrazolo[3,4-c][2,7]naphthyridin-5-yl)phenol

A solution of 350 mg (0.75 mmol) of 3-(4-methoxybenzyl)-5-(4-methoxyphenyl)-1-methyl-6,7-dihydro-3H-benzo[f]pyrazolo[3,4-c][2,7]naphthyridine dissolved in 15 ml of trifluoroacetic acid is carried at 70° C. for 4 hours and then cooled to room temperature. The solvents are evaporated and then water is added. The product is extracted with ethyl acetate; the organic phases are dried on magnesium sulfate and concentrated. The residue is triturated in acetonitrile. The solid is filtered and then dissolved in 20 ml of anhydrous dichloroethane. The reaction medium is cooled to 0° C. before the slow addition of 7 ml (7 mmol) of a 1 M solution of boron tribromide in dichloromethane. The reaction medium is carried at reflux for 7 hours and then cooled again to 0° C. Methanol is added until the reaction medium is completely homogenized. The solvents are evaporated and then the residue is purified several times by silica gel chromatography (eluent: 95:5 DCM/MeOH) to yield 32 mg (15%) of 4-(1-methyl-3H-benzo[f]pyrazolo[3,4-c][2,7]naphthyridin-5-yl)phenol in the form of a brown solid.

LCMS (ESI, m/z): (M+1) 327.14

$^1$H NMR: $\delta_H$ pm 400 MHz, DMSO: 9.42 (1H, s, $CH_{arom}$), 9.11 (1H, d, $CH_{arom}$), 8.39 (1H, d, $CH_{arom}$), 8.15 (1H, dd, $CH_{arom}$), 8.03 (1H, dd, $CH_{arom}$), 7.70 (2H, d, $CH_{arom}$), 7.05 (2H, d, $CH_{arom}$), 3.02 (3H, s, $CH_3$).

G-2 Deprotection of the Pyrrole and the Phenol when the Latter is Protected by a Benzyl Group

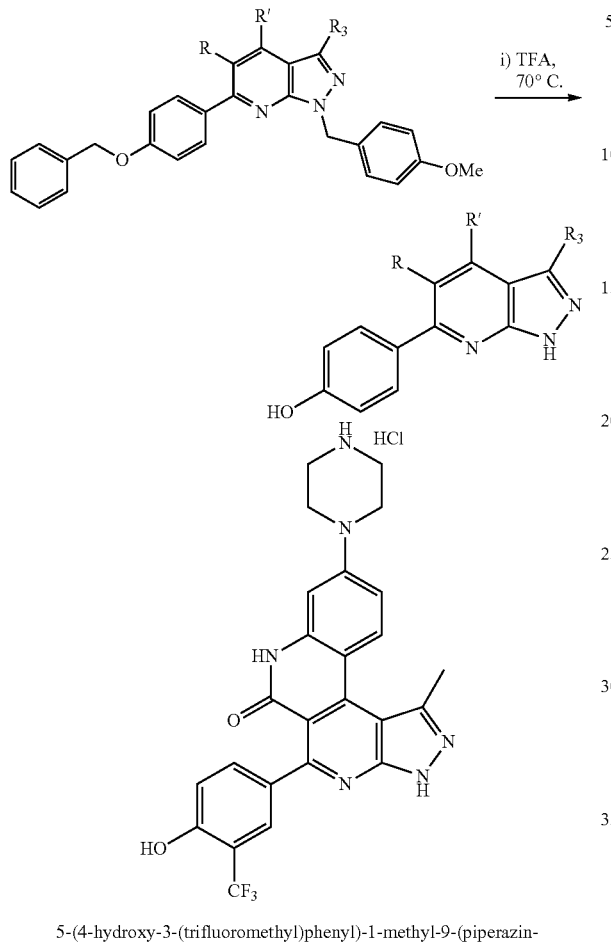

5-(4-hydroxy-3-(trifluoromethyl)phenyl)-1-methyl-9-(piperazin-1-yl)-3H-benzo[f]pyrazolo[3,4-c][2,7]naphthyridin-6(7H)-one A solution of 1.8 g (2.55 mmol) of 5-(4-(benzyloxy)-3-(trifluoromethyl)phenyl)-3-(4-methoxybenzyl)-1-methyl-9-(piperazin-1-yl)-3H-benzo[f]pyrazolo[3,4-c][2,7]naphthyridin-6(7H)-one dissolved in 25 ml of trifluoroacetic acid is carried at 70° C. for 3 hours. After returning to room temperature, 50 ml of diisopropyl ether is added until a stable precipitate appears; the latter is filtered and then taken up in water. Acidity is neutralized by the addition of 1 M soda. The solid is filtered again and then triturated several times in hot methanol to yield after a final filtration 950 mg of 5-(4-hydroxy-3-(trifluoromethyl)phenyl)-1-methyl-9-(piperazin-1-yl)-3H-benzo[f]pyrazolo[3,4-c][2,7]naphthyridin-6(7H)-one. The product is then taken up in 20 ml of anhydrous dioxane; a 4 M solution of hydrochloric acid in dioxane (932 µl, 3.73 mmol) is added and the reaction medium is stirred at room temperature for 2 hours. The precipitate is filtered, rinsed with dioxane and triturated in methanol to yield 475 mg (36%) of 5-(4-hydroxy-3-(trifluoromethyl)phenyl)-1-methyl-9-(piperazin-1-yl)-3H-benzo[f]pyrazolo[3,4-c][2,7] naphthyridin-6(7H)-one hydrochloride in the form of a yellow solid.

LCMS (ESI, m/z): (M+1) 495.23

$^1$H NMR: $\delta_H$ pm 400 MHz, DMSO: 11.42 (1H, bs, NH), 10.78 (1H, bs, OH), 9.37 (2H, bs, NH.HCl), 8.25 (1H, d, CH$_{arom}$), 7.55-7.71 (2H, m, CH$_{arom}$), 7.02-7.12 (2H, m, CH$_{arom}$), 6.83 (1H, s, CH$_{arom}$), 3.50-3.60 (4H, m, 2CH$_2$), 3.16-3.32 (4H, m, 2CH$_2$), 2.79 (3H, s, CH$_3$).

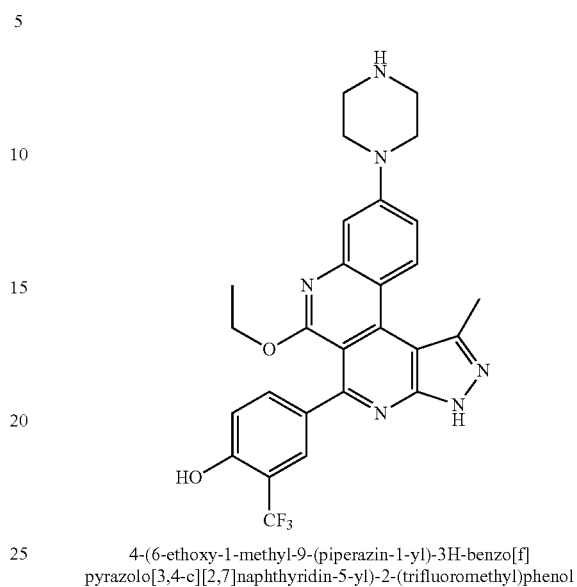

4-(6-ethoxy-1-methyl-9-(piperazin-1-yl)-3H-benzo[f]pyrazolo[3,4-c][2,7]naphthyridin-5-yl)-2-(trifluoromethyl)phenol A solution of 427 mg (0.513 mmol) of tert-butyl 4-(5-(4-benzyloxy)-3-(trifluoromethyl)phenyl)-6-ethoxy-3-(4-methoxybenzyl)-1-methyl-3H-benzo[f]pyrazolo[3,4-c][2,7] naphthyridin-9-yl)piperazine-1-carboxylate dissolved in 5 ml of trifluoroacetic acid is carried at 70° C. for 4 hours. After returning to room temperature, 30 ml of diisopropyl ether is added until a stable precipitate appears; the latter is filtered and then taken up in water. Acidity is neutralized by the addition of 1 M soda. The solid is filtered again and then purified by silica gel chromatography (eluent: 85:10:5 dichloromethane/methanol/ammonium) to yield 129 mg (48%) of 4-(6-ethoxy-1-methyl-9-(piperazin-1-yl)-3H-benzo[f]pyrazolo[3,4-c][2,7]naphthyridin-5-yl)-2-(trifluoromethyl)phenol in the form of a yellow solid.

LCMS (ESI, m/z): (M+1) 523.35

$^1$H NMR: $\delta_H$ pm 400 MHz, DMSO: 13.80 (1H, bs, NH), 8.52 (1H, d, CH$_{arom}$), 7.55-7.63 (2H, m, CH$_{arom}$), 7.31 (1H, dd, CH$_{arom}$), 7.06-7.12 (2H, m, CH$_{arom}$), 4.23 (2H, q, CH$_2$), 3.20-3.40 (4H, m, 2CH$_2$), 2.88-2.93 (4H, m, 2CH$_2$), 2.88 (3H, s, CH$_3$), 0.88 (3H, t, CH$_3$).

G-3 Deprotection of the Phenol when it is Protected by a Methoxy

G-3a General Case: Use of Boron Tribromide

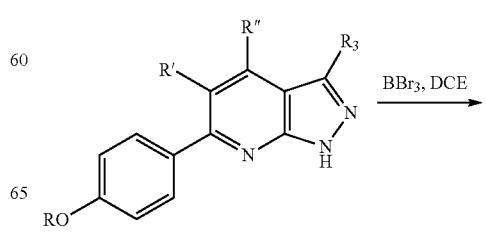

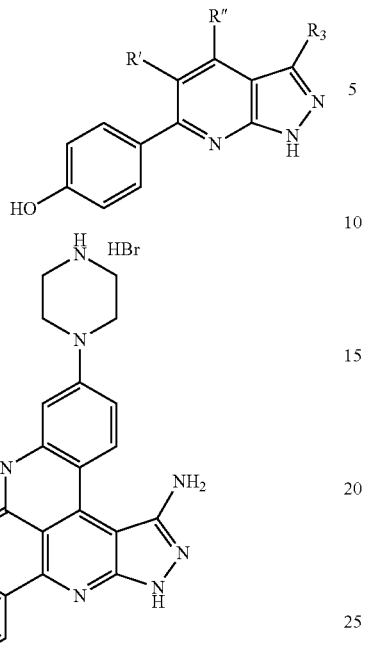

1-amino-5-(4-hydroxyphenyl)-9-(piperazin-1-yl)-3H-
benzo[f]pyrazolo[3,4-c][27]naphthyridin-6(7H)-one hydrobromide A solution of 350 mg (0.64 mmol) of tert-butyl 4-(1-amino-5-(4-methoxyphenyl)-6-oxo-6,7-dihydro-3H-benzo[f]pyrazolo[3,4-c][2,7]naphthyridin-9-yl)piperazine-1-carboxylate is dissolved in 15 ml of anhydrous dichloroethane. The reaction medium is cooled to −78° C. before the slow addition of 0.30 ml (3.23 mmol) of boron tribromide. The reaction medium is carried at reflux for 4 hours. Methanol (roughly 10 ml) is added at 0° C. and then the reaction medium is stirred at 40° C. for 1 hour. The solid formed is filtered under heat and then rinsed with diethyl ether. Recrystallization of the solid in isopropanol yields 0.26 g (80%) of 1-amino-5-(4-hydroxyphenyl)-9-(piperazin-1-yl)-3H-benzo[f]pyrazolo[3,4-c][2,7]naphthyridin-6(7H)-one hydrobromide in the form of a light orange solid.

LCMS (ESI, m/z): (M+1) 509.45

$^1$H NMR: $\delta_H$ pm 400 MHz, DMSO: 11.30 (1H, bs, NH), 8.84-8.88 (1H, m, CH$_{arom}$), 7.32 (2H, d, CH$_{arom}$), 7.04-7.10 (1H, m, CH$_{arom}$), 6.74-6.80 (3H, m, CH$_{arom}$), 3.50-3.60 (4H, m, 2CH$_2$), 3.24-3.35 (4H, m, CH$_2$).

G-3b Specific Case: Use of Hydriodic Acid

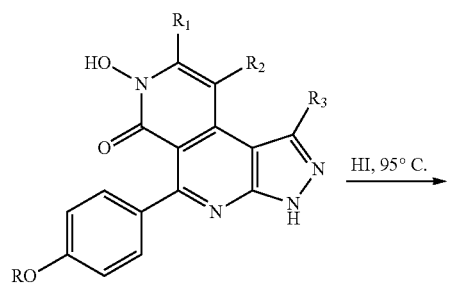

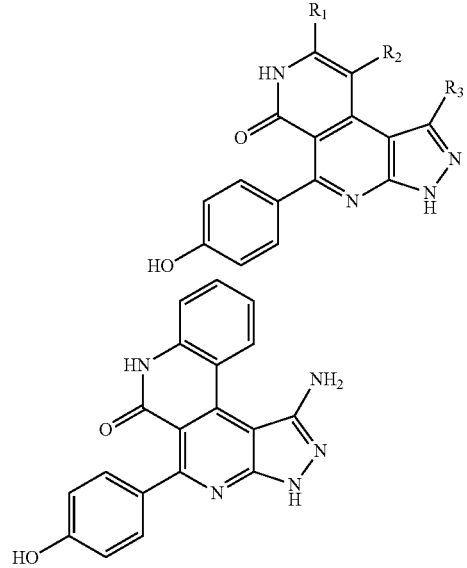

1-amino-5-(4-hydroxyphenyl)-3H-
benzo[f]pyrazolo[3,4-c][2,7]naphthyridin-6(7H)-one A solution of 2.27 g (6.08 mmol) of 1-amino-7-hydroxy-5-(4-methoxyphenyl)-3H-benzo[f]pyrazolo[3,4-c][2,7]naphthyridin-6(7H)-one dissolved in 68 ml of 57% hydriodic acid in water is carried at reflux for 7 hours. After returning to room temperature, the solid is filtered and rinsed abundantly with water. It is then taken up in water, and 1 N soda is added to adjust the pH to 7. The solid is filtered again, triturated in methanol and then dried to yield 985 mg (47%) of 1-amino-5-(4-hydroxyphenyl)-3H-benzo[f]pyrazolo[3,4-c][2,7]naphthyridin-6(7H)-one hydrobromide in the form of a yellow solid.

LCMS (ESI, m/z): (M+1) 344.29

$^1$H NMR: $\delta_H$ pm 400 MHz, DMSO: 12.89 (1H, bs, NH), 11.45 (1H, bs, NH), 9.52 (1H, bs, OH), 9.07 (1H, d, CH$_{arom}$), 7.57-7.63 (1H, m, CH$_{arom}$), 7.25-7.40 (4H, m, CH$_{arom}$), 6.75 (2H, d, CH$_{arom}$), 5.30 (2H, bs, NH$_2$).

II. Biological Tests for the Compounds According to the Invention

II-1 Experimental Protocols

Test for Measurement of ALK Inhibition

A ViewPlate microplate (Packard) is incubated with 0.1 mg/ml GST-PLCγ1 substrate (purified recombinant form) in phosphate buffer (PBS, pH 7.4) (100 µl/well) for one hour under stirring. The plate is then saturated with blocking solution comprising 5% bovine serum albumin (BSA) (Sigma) in PBS buffer, pH 7.4.

After having added the inhibitor at the desired final concentration (typical range between 30 µM and 10 nM), the reaction is carried out by adding 180 ng/ml ALK to a reaction buffer comprised of 13 mM Tris, pH 7.5 (Sigma); 6.5 mM MgCl$_2$ (Merck); 0.65 mM dithiothreitol (DTT) (Acros); 39 mM sodium β-glycerophosphate (TCI); 0.65 mM sodium orthovanadate (Sigma); and 250 µM ATP (Sigma). Incubation is carried out for 30 minutes at 30° C. under stirring.

After three washings under stirring in 0.1% PBS/Tween-20 buffer (Sigma), an anti-phosphotyrosine antibody, coupled with HRP (UBI) diluted to 1/1000 in 5 mg/ml PBS/BSA buffer, is incubated for one hour with stirring. After three new washings in 0.1% PBS/Tween-20, the wells are incubated for two minutes with 100 μl of SuperSignal ELISA mixture (Pierce).

The signal is read in luminescence mode using a luminometer (SpectraMax M5e, Molecular Devices).

Test for Measurement of Cell Prolifearation Inhibition (Karpas 299)

The antiproliferative activity of the compounds according to the invention has been measured by the ATPlite technique (Perkin Ekmer).

Human cells of non-adherent anaplasic large cell lymphoma (Karpas 299) are seeded in 96-well plates (300,000 cells/ml) on day 1, at a concentration compatible with a logarithmic growth for 72 hours necessary for the evaluation of the compounds according to the invention. All the cells are treated on day 1 and then placed in an incubator at 37° C., under a 5% $CO_2$ atmosphere. Cell viability is evaluated on day 4 by dosing the emitted ATP, which is a characteristic of viable cells. $IC_{50}$s are determined by a non linear regression based on a sigmoidal model of dose/response relationship, the Hill coefficient being let variable, performed with the Graph-Pad software according to the algorithm provided.

II-2 Results

The results of enzymatic $IC_{50}$ on ALK are presented in the following table, with:

| Compound | $IC_{50}$ (ALK) | Compound | $IC_{50}$ (ALK) |
| --- | --- | --- | --- |
| 01 | A | 02 | A |
| 03 | C | 04 | A |
| 05 | A | 06 | B |
| 07 | A | 08 | C |
| 09 | B | 10 | A |
| 11 | A | 12 | A |
| 13 | A | 14 | A |
| 15 | B | 16 | A |
| 17 | A | 18 | A |
| 19 | A | 20 | A |
| 21 | A | 22 | C |
| 23 | A | 24 | A |
| 25 | A | 27 | C |
| 28 | B | 30 | A |
| 31 | C | 32 | A |
| 33 | A | 35 | C |
| 36 | C | 37 | A |
| 38 | A | 39 | C |
| 41 | B | 42 | A |
| 44 | C | 45 | C |
| 46 | A | 47 | B |
| 48 | C | 49 | A |
| 50 | B | 51 | A |
| 52 | A | 53 | A |
| 54 | C | 55 | B |

A signifying $IC_{50}$ < 100 nM
B signifying 100 nM < $IC_{50}$ < 1 μM
C signifying 1 μM < $IC_{50}$ < 10 μM II-3 Comparative Tests Addition of a Fourth Cycle The Alk inhibition activity as well as the antiproliferative activity on Karpas 299 cell line of compound 06 according to the invention have been compared to those of compound 98 of US 2007/0032515.

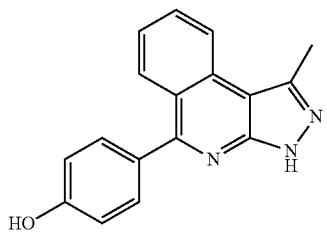

(98)

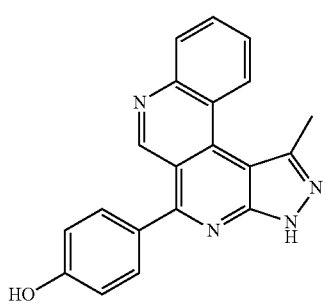

(06)

The results obtained are presented in the table below:

| Compound | Alk enzymatic inhibition ($IC_{50}$, μM) | Karpas 299 cell proliferation inhibition ($IC_{50}$, μM) |
| --- | --- | --- |
| Comparative compound 98 | 0.07 μM | 4.04 μM |
| Compound 06 | 0.035 μM | 1 μM |

In view of these results, it appears clearly that the addition of a fourth cycle fused to the tricyclic system described in US 2007/0032515 has a favourable effect both on Alk enzymatic inhibition and on Karpas 299 cell proliferation inhibition.

Addition of a Carbonyl Functional Group

The biological activity of two compounds according to the invention has been tested and compared.

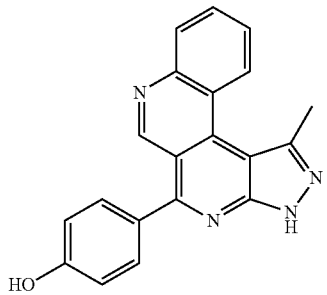

(06)

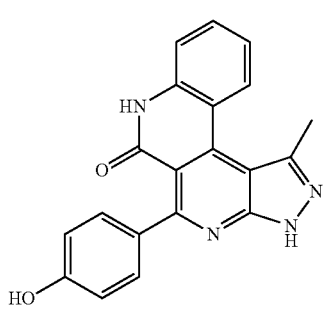

(02)

The results obtained are presented in the table below:

| Compound | Alk enzymatic inhibition (IC$_{50}$, μM) | Karpas 299 cell proliferation inhibition (IC$_{50}$, μM) |
|---|---|---|
| Comparative 06 | 0.035 μM | 1 μM |
| Compound 02 | 0.0025 μM | 0.168 μM |

These two compounds have thus an important activity both on Alk enzymatic inhibition and on Karpas 299 cell proliferation inhibition. However, compound 02 has a C=O functional group which appears to have a very favourable effect on the biological activity of this compound. Indeed, the Alk enzymatic inhibition and the Karpas 299 cell proliferation inhibition are improved in comparison with compound 06.

Abbreviations

Boc tert-Butoxycarbonyl
DCE 1,1-Dichloroethane
DCM Dichloromethane
DMF Dimethylformamide
DMSO Dimethylsulfoxide
ESI Electrospray ionization
HPLC High-performance liquid chromatography
EI Electrospray ionization
LCMS Liquid chromatography coupled with mass spectrometry
PPA Polyphosphoric acid
NMR Nuclear magnetic resonance
RT Room temperature
TFA Trifluoroacetic acid
THF Tetrahydrofuran

The invention claimed is:

1. A compound of following general formula (I):

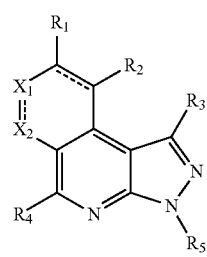

or a pharmaceutically acceptable salt of same, a tautomer of same, or a stereoisomer or mixture of stereoisomers in any proportions of same,
wherein:
- - - - represents a double or single bond,
$X_1$ represents a single bond, O, S or $NR_6$ when - - - - represents a single bond between $X_1$ and $X_2$, or
$X_1$ represents N when - - - - represents a double bond between $X_1$ and $X_2$,
$X_1$ represents C=O or C=S when - - - - represents a single bond between $X_1$ and $X_2$, or
$X_2$ represents a CH, C(OR$_7$), C(NR$_8$R$_9$) or C(SR$_{10}$) group when - - - - represents a double bond between $X_1$ and $X_2$,
$R_1$ and $R_2$ together form, with the carbon atoms that carry them, a ring selected from aryl, heteroaryl, carbocycle and heterocycle,
said ring being optionally substituted by one or more groups selected from a halogen atom, a CN, NO$_2$, OR$_{26}$, SR$_{27}$, NR$_{28}$R$_{29}$, COR$_{30}$, CO$_2$R$_{31}$, OCO$_2$R$_{32}$, CONR$_{33}$R$_{34}$, NR$_{35}$COR$_{36}$, NR$_{37}$SO$_2$R$_{38}$, SO$_2$NR$_{39}$R$_{40}$, SO$_2$R$_{41}$, SOR$_{42}$, (C$_1$-C$_6$)alkyl, aryl, heteroaryl, carbocycle, heterocycle group,
the (C$_1$-C$_6$)alkyl chains as well as the rings of the whole being optionally substituted by one or more groups selected from OR$_{43}$, NR$_{44}$R$_{45}$, —C(O)O—(C$_1$-C$_6$)-alkyl, heterocycle and (C$_1$-C$_6$)-alkyl, and $R_3$ represents a hydrogen atom, an —NR$_{46}$R$_{47}$, —CONR$_{46}$R$_{47}$, —NO$_2$, —NR$_{48}$-aryl, —NR$_{48}$-aralkyl, —NR$_{48}$-heteroaryl, —NR$_{48}$-carbocycle, —NR$_{48}$-heterocycle, —NR$_{48}$CO-aryl, —NR$_{48}$CO—(C$_1$-C$_6$)alkyl, —NR$_{48}$CO-aralkyl, —NR$_{48}$CO-heteroaryl, —NR$_{48}$CO-carbocycle, —NR$_{48}$CO-heterocycle, —NR$_{48}$SO$_2$—(C$_1$-C$_6$)alkyl, —NR$_{48}$SO$_2$-aryl, —NR$_{48}$SO$_2$-aralkyl, —NR$_{48}$SO$_2$-heteroaryl, —NR$_{48}$SO$_2$-carbocycle, —NR$_{48}$SO$_2$-heterocycle, —OR$_{49}$, —CO$_2$R$_{49}$, aryl, heteroaryl, carbocycle, heterocycle, aralkyl, or (C$_1$-C$_6$)alkyl group, the (C$_1$-C$_6$)alkyl chains as well as the aromatic or non-aromatic rings of said group being optionally substituted by one or more groups selected from a halogen atom, a CN, NO$_2$, OR$_{26}$, SR$_{27}$, NR$_{28}$R$_{29}$, COR$_{30}$, CO$_2$R$_{31}$, OCO$_2$R$_{32}$, CONR$_{33}$R$_{34}$, NR$_{35}$COR$_{36}$, NR$_{37}$SO$_2$R$_{38}$, SO$_2$NR$_{39}$R$_{40}$, SO$_2$R$_{41}$, SOR$_{42}$, (C$_1$-C$_6$)alkyl, aryl, heteroaryl, carbocycle, heterocycle group, the (C$_1$-C$_6$)alkyl chains as well as the rings of the whole being optionally substituted by one or more groups selected from OR$_{43}$, NR$_{44}$R$_{45}$, heterocycle and (C$_1$-C$_6$)alkyl, and $R_4$ represents an aryl, aralkyl, heteroaryl, carbocycle, or heterocycle group, said group being optionally substituted by one or more groups selected from a halogen atom, a CN, NO$_2$, OR$_{50}$, SR$_{51}$, NR$_{52}$R$_{53}$, COR$_{54}$, CO$_2$R$_{55}$, OCO$_2$R$_{56}$, CONR$_{57}$R$_{58}$, NR$_{59}$COR$_{60}$, NR$_{61}$SO$_2$R$_{62}$, SO$_2$NR$_{63}$R$_{64}$, SO$_2$R$_{65}$, SOR$_{66}$, (C$_1$-C$_6$)alkyl, (C$_1$-C$_6$)haloalkyl, (C$_1$-C$_6$)haloalkoxy or OCOR$_{67}$ group, $R_5$ represents a hydrogen atom or a CO—(C$_1$-C$_6$)alkyl or CO$_2$—((C$_1$-C$_6$)alkyl) group, with:

$R_6$ representing a hydrogen atom, an OH group, an aralkyl or (C$_1$-C$_{10}$)alkyl group, the (C$_1$-C$_{10}$)alkyl chains as well as the rings of the whole being optionally substituted by one or more groups selected from halogen; OR$_{68}$; NR$_{69}$R$_{70}$; heterocycle optionally substituted by one or more groups selected from OR$_{68}$, NR$_{69}$R$_{70}$ and (C$_1$-C$_6$)alkyl, $R_7$ and $R_{10}$ each representing, independently of each other, a hydrogen atom or a (C$_1$-C$_{10}$)alkyl group, the (C$_1$-C$_{10}$)alkyl groups being optionally substituted by one or more groups selected from halogen; OR$_{68}$; NR$_{69}$R$_{70}$; and heterocycle optionally substituted by one or more groups among OR$_{68}$, NR$_{69}$R$_{70}$ or (C$_1$-C$_6$)alkyl, $R_8$ and $R_9$ each representing, independently of each other, a hydrogen atom or a (C$_1$-C$_6$)alkyl group, or $R_8$ and $R_9$ together forming, with the nitrogen atom that carries them, a heteroaryl or heterocycle group optionally substituted by a (C$_1$-C$_6$)alkyl group, $R_{11}$ to $R_{42}$ and $R_{50}$ to $R_{66}$ each representing, independently of each other, a hydrogen atom or a (C$_1$-C$_6$)-alkyl, aryl or aralkyl group, $R_{43}$, $R_{46}$ to $R_{49}$ and $R_{68}$ each representing, independently of each other, a hydrogen atom or a (C$_1$-C$_6$)-alkyl group, $R_{44}$, $R_{45}$, $R_{69}$, $R_{70}$, $R_{72}$ and $R_{73}$ each representing, independently of each other, a hydrogen atom or a ($C_1$-$C_6$)alkyl group, or $R_{44}$ and $R_{45}$ together forming, with the nitrogen atom that carries them, an optionally substituted heterocycle group, or $R_{69}$ and $R_{70}$ together forming, with the nitrogen atom that carries them, an optionally substituted heterocycle group, or $R_{72}$ and $R_{73}$ together forming, with the nitrogen atom that carries them, at optionally substituted heterocycle group, and $R_{67}$ representing a hydrogen atom or an $NR_{72}R_{73}$, optionally substituted ($C_1$-$C_6$)alkyl and optionally substituted ($C_2$-$C_6$)alkenyl group.

2. The compound according to claim 1, wherein $$X_1 \text{---} X_2$$

represents a —C(=O)—, —O—C(=O)—, —$NR_6$—C(=O)—, —N=CH— or —N=C($OR_7$)— group.

3. The compound according to claim 1, wherein $R_1$ and $R_2$ together form, with the carbon atoms that carry them, a ring, wherein the ring is an aryl, said ring being optionally substituted by one or more groups selected from a halogen atom, a CN, $NO_2$, $OR_{26}$, $SR_{27}$, $NR_{28}R_{29}$, $COR_{30}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, ($C_1$-$C_6$)alkyl, aryl, heteroaryl, carbocycle and heterocycle group, the ($C_1$-$C_6$)alkyl chains as well as the rings of the whole being optionally substituted by one or more groups selected from $OR_{43}$, $NR_{44}R_{45}$, —C(O)O—($C_1$-$C_6$)-alkyl, heterocycle and ($C_1$-$C_6$)-alkyl.

4. The compound according to claim 1, wherein $R_3$ represents a hydrogen atom, an aralkyl, ($C_1$-$C_6$)alkyl, —$NR_{46}R_{47}$, —$NR_{48}$CO-aryl, —$NR_{48}$CO—($C_1$-$C_6$)alkyl, —$NR_{48}$CO-aralkyl, —$NR_{48}$CO-heteroaryl, —$NR_{48}SO_2$—($C_1$-$C_6$)alkyl, —$NR_{48}SO_2$-aryl, —$NR_{48}SO_2$-aralkyl, —$NR_{48}SO_2$-heteroaryl, aryl, heteroaryl, or heterocycle group, the ($C_1$-$C_6$)alkyl chains as well as the aromatic or non-aromatic rings of said group being optionally substituted by one or more groups selected from a halogen atom, an $NO_2$, $NR_{28}R_{29}$, $CO_2R_{31}$, $OCO_2R_{32}$, $CONR_{33}R_{34}$, $NR_{35}COR_{36}$, $NR_{37}SO_2R_{38}$, $SO_2NR_{39}R_{40}$, $SO_2R_{41}$, $SOR_{42}$, ($C_1$-$C_6$)alkyl, aryl, heteroaryl, carbocycle, heterocycle group, the ($C_1$-$C_6$)alkyl chains as well as the rings of the whole being optionally substituted by one or more groups selected from $OR_{43}$, $NR_{44}R_{45}$, heterocycle and ($C_1$-$C_6$)-alkyl.

5. The compound according to claim 1, wherein $R_4$ represents an aryl, aralkyl, heteroaryl, carbocycle, or heterocycle group, said group being optionally substituted by one or more groups selected from a halogen atom, an $OR_{50}$, $CO_2R_{55}$, $OCO_2R_{56}$, ($C_1$-$C_6$)alkyl, ($C_1$-$C_6$)haloalkyl, $OCOR_{67}$ group.

6. The compound according to claim 1, wherein $R_5$ represents a hydrogen atom.

7. The compound according to claim 1, wherein said compound is selected from:

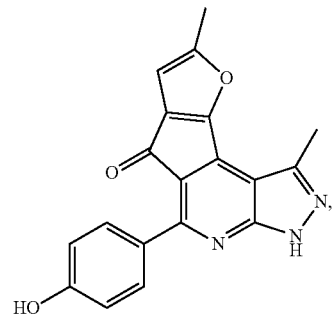

01

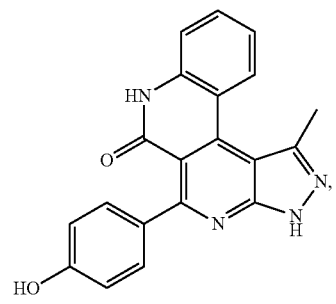

02

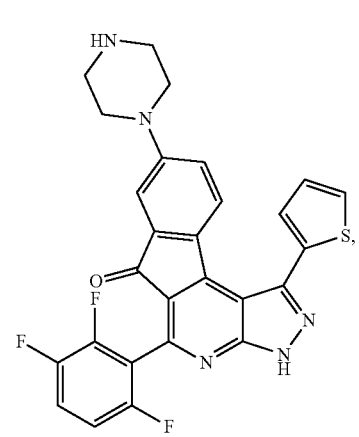

03

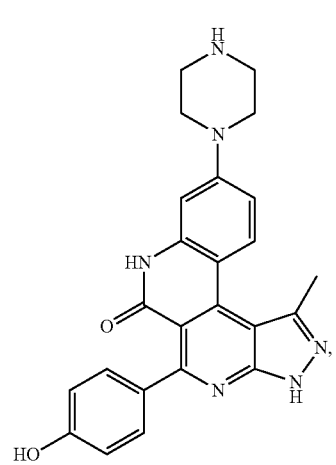

04

-continued
05
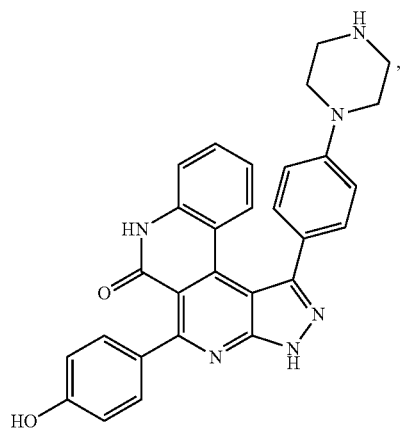
06
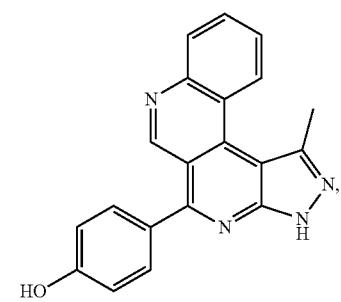
07
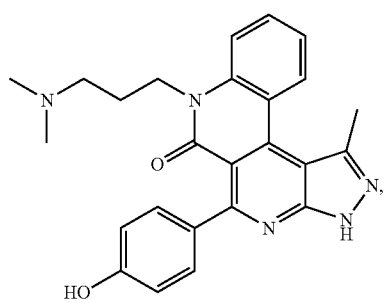
08
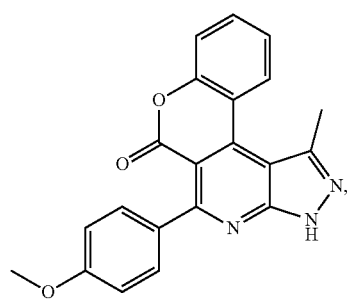
09
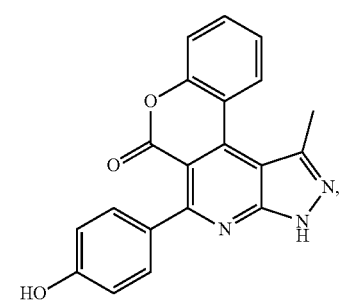
-continued
10
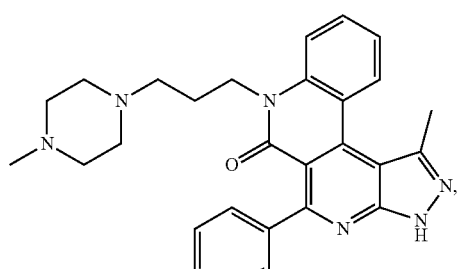
11
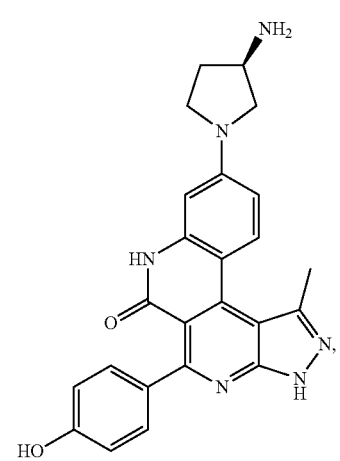
12
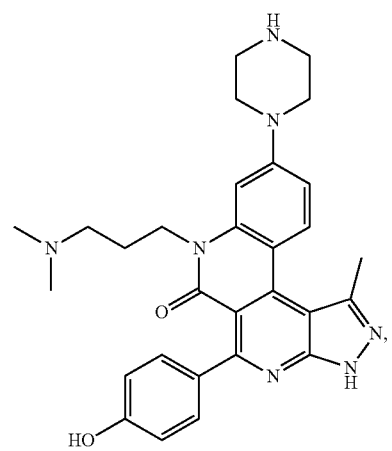

-continued
13
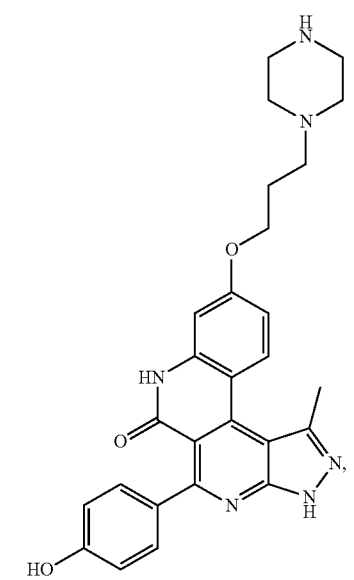
14
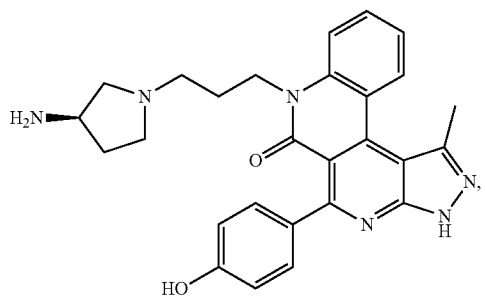
15
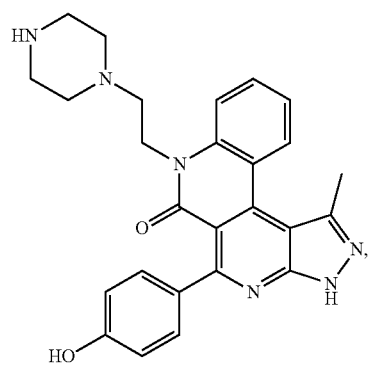
-continued
16
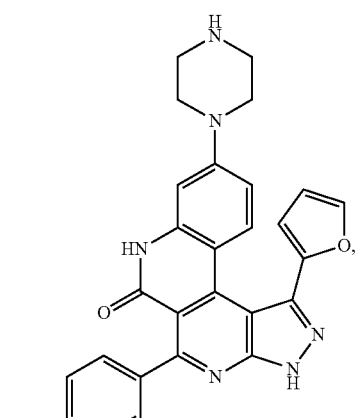
17
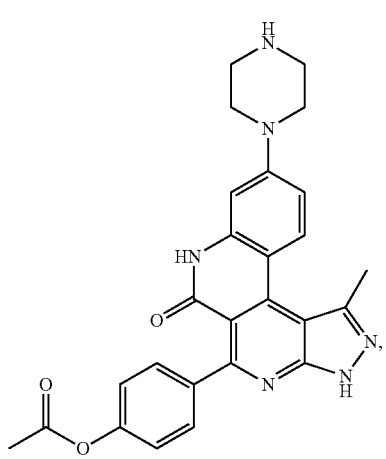
18
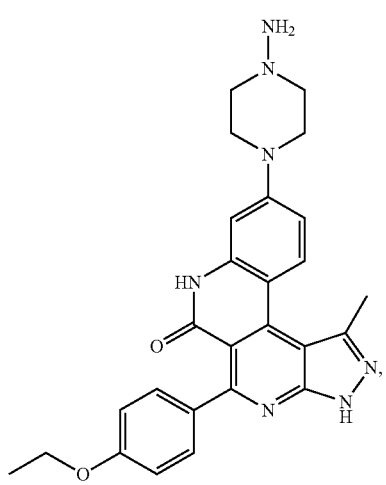

99
-continued
19
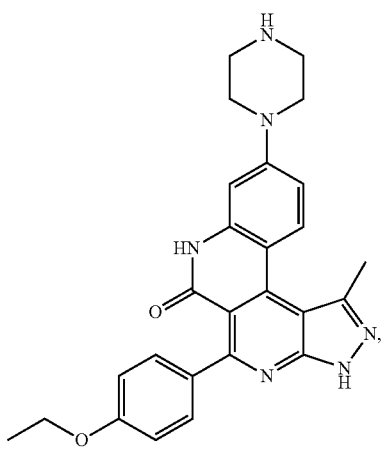
20
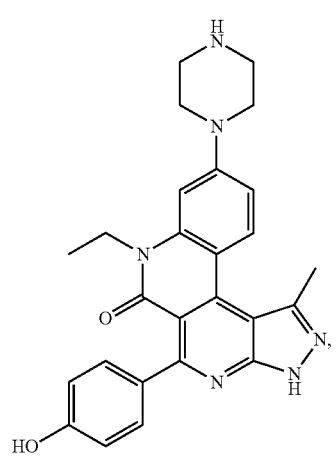
21
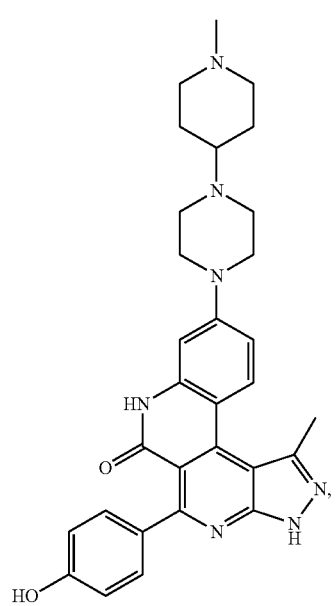
100
-continued
22
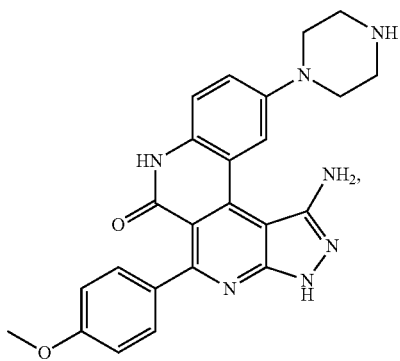
23
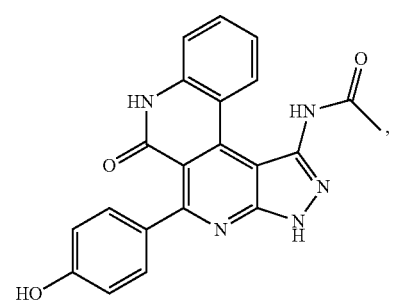
24
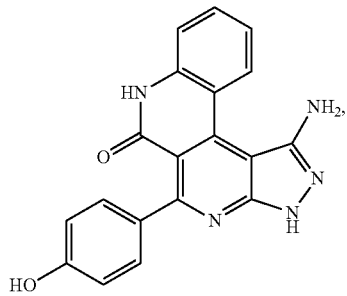
25
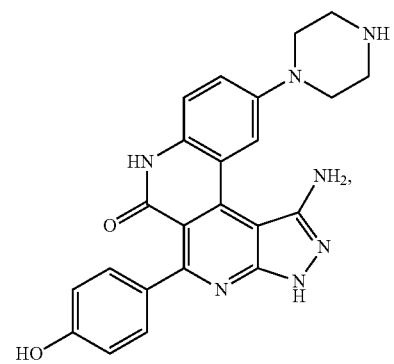

101
-continued
26
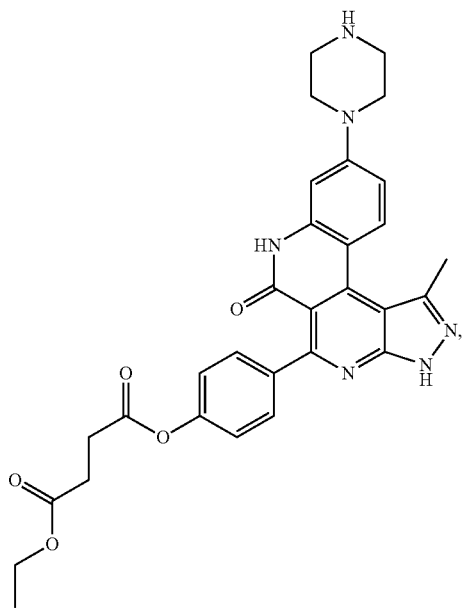
27
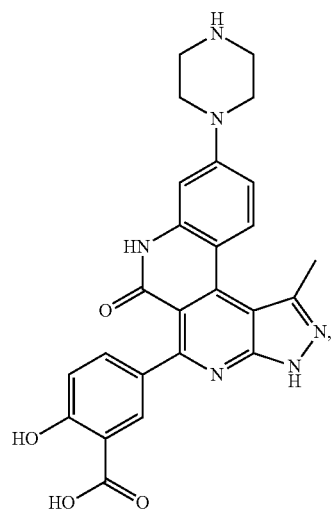
102
-continued
31
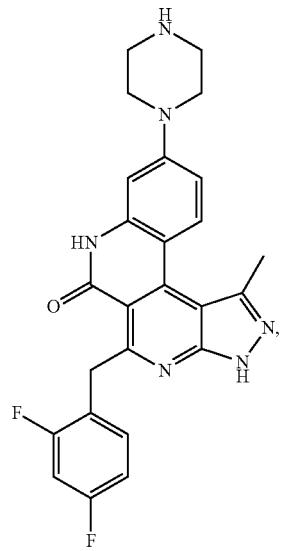
32
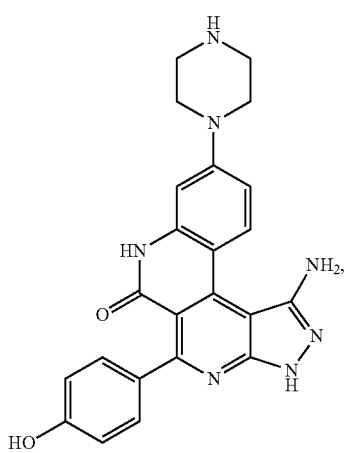
33
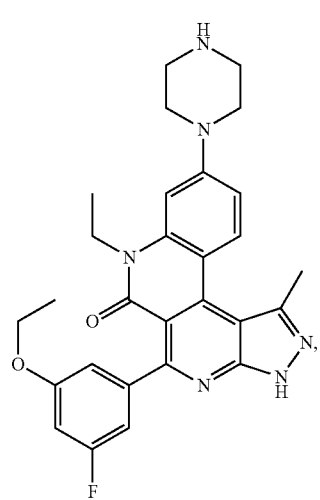

36
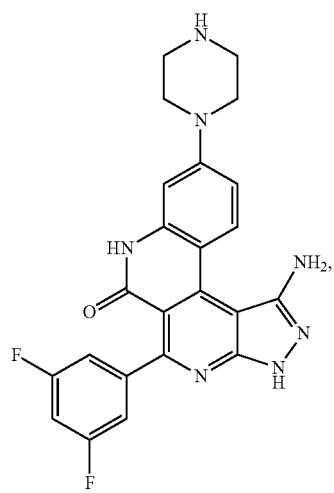
37
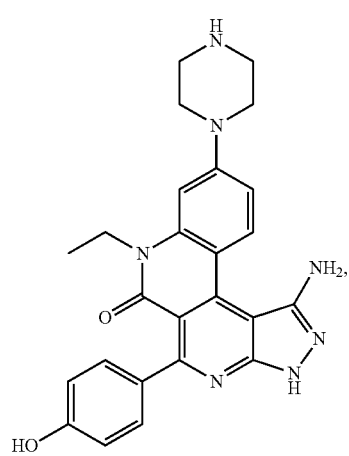
38
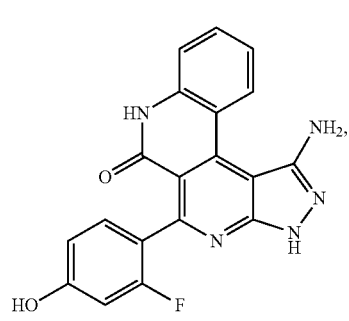
41
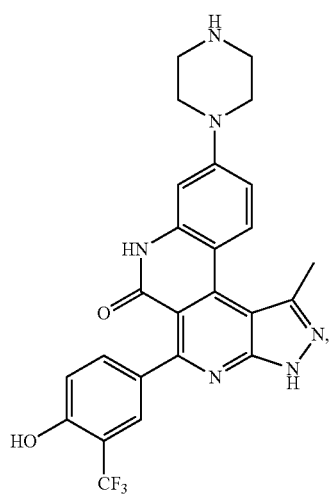
42
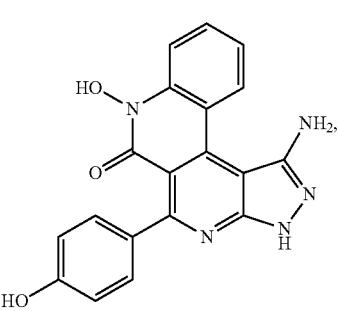
46
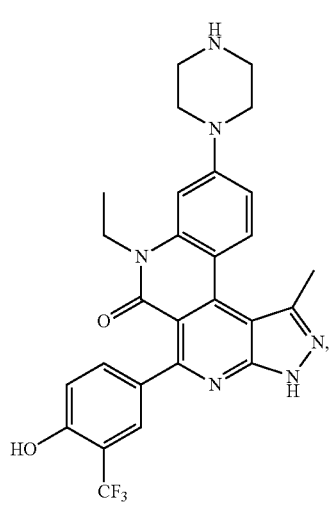

-continued
47
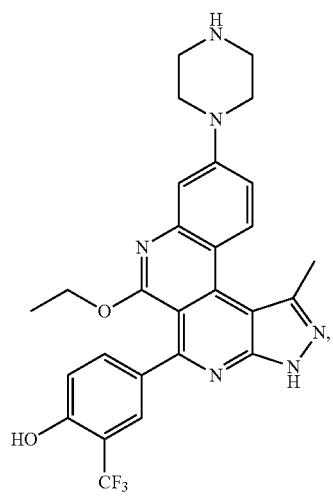
48
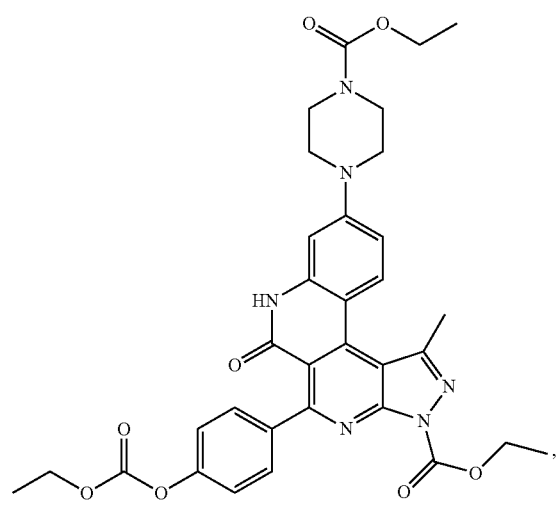
49
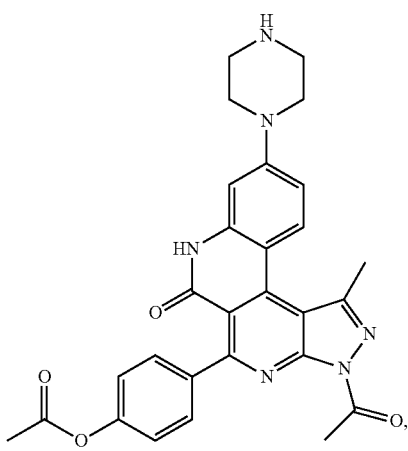
-continued
50
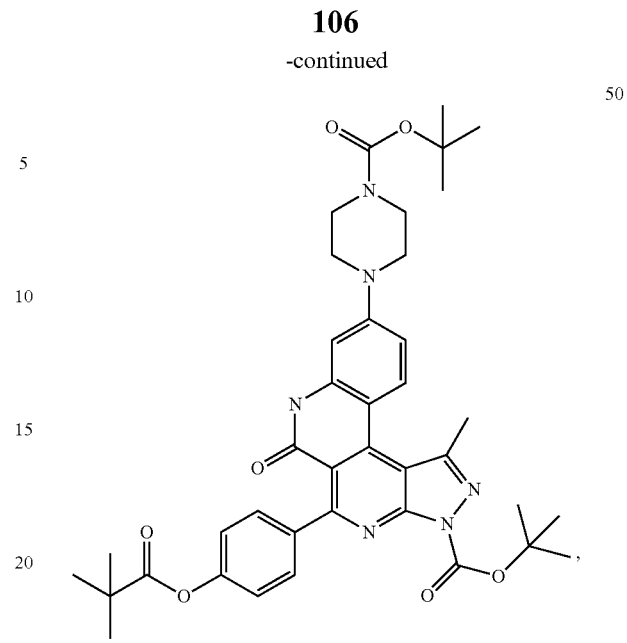
51
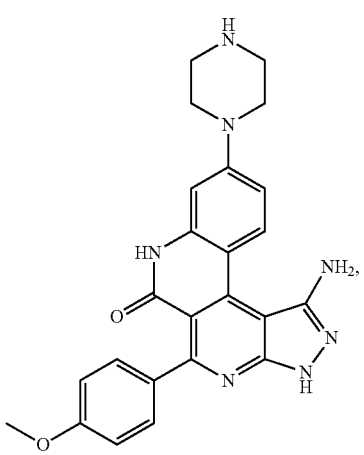
52
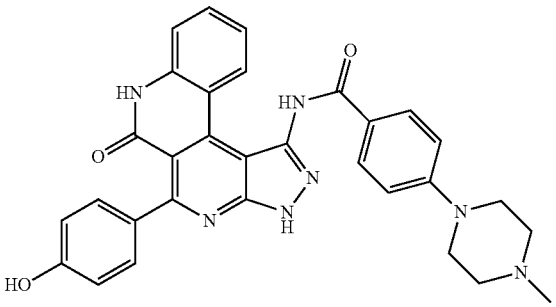

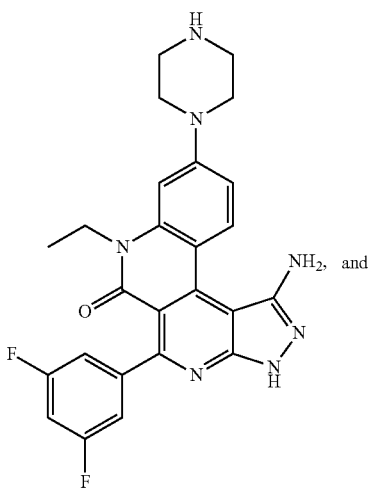

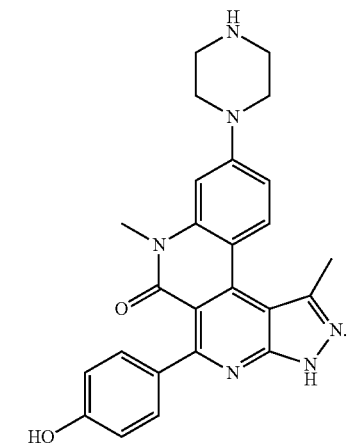

8. A pharmaceutical composition comprising at least one compound according to claim 1, and at least one pharmaceutically acceptable excipient.

9. The pharmaceutical composition according to claim 8, further comprising at least one other active ingredient.

10. A pharmaceutical composition comprising:
(i) at least one compound according to claim 1,
(ii) at least one other active ingredient,
as a combination product for simultaneous, separate or staggered use.

11. A method for preparing a compound of formula (I) according to claim 1, wherein $X_2$=C=O and $R_5$=H, comprising the following successive steps:
(a1) reaction of a compound of following formula (II):

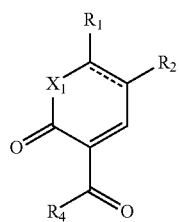

wherein $R_1$, $R_2$, $R_4$ and $X_1$ are as defined in claim 1, with a compound of following formula (III),

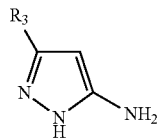

wherein $R_3$ is as defined in claim 1,
to yield a compound of formula (I) wherein $X_2$=C=O and $R_5$=H,
(b1)) optionally salification of the compound of formula (I) obtained in the preceding step (a1) to yield a pharmaceutically acceptable salt of same, and
(c1) separation of the compound of formula (I) obtained in the preceding step (a1) or (b1) from the reaction medium.

12. A method for preparing a compound of formula (I) according to claim 1, wherein

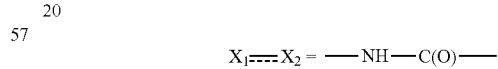

or —O—C(O)— and $R_5$=H, comprising the following successive steps:
(a2) hydrolysis reaction of the CN function into acid (—COOH) or into amide (—CONH$_2$) of a compound of one of the following two formulas (IV) or (IV-a):

(IV)

(IV-a)

wherein $A_2$ represents a leaving, group, $A_2'$ represents an oxygen or sulfur atom and $R_1$, $R_2$, $R_3$ and $R_4$ are as defined in claim 1,
followed by intramolecular cyclization to yield a compound of formula (I) wherein $$X_1\text{---}X_2 = \text{---NH---C(O)---}$$

or —O—C(O)— and $R_5$=H,
(b2) optionally salification of the compound of formula (I) obtained in the preceding step (a2) to yield a pharmaceutically acceptable salt of same, and
(c2) separation of the compound of formula (I) obtained in the preceding step (a2) or (b2) from the reaction medium.

13. A method for preparing a compound of formula (I) according to claim 1, wherein $$X_1 = X_2 = -NR_6-C(O)-$$

and $R_5$=H, comprising the following successive steps:
- (a3) deprotection of the protecting or precursor group OP of an amine functional group of a compound of following formula (IX):

(IX)

wherein $A_3$ represents a $(C_1-C_6)$alkoxy group, GP represents $NO_2$, $NH-CO-(C_1-C_6)$alkyl, $NH-CO$-aralkyl, $NH-CO_2-(C_1-C_6)$alkyl or $NH-CO_2$aralkyl, and $R_1$, $R_2$, $R_3$ and $R_4$ are as defined in claim 1, followed by intramolecular cyclization to yield a compound of formula (I) wherein $$X_1 = X_2 = -NR_6-C(O)-$$

and $R_5$=H with $R_6$=H or OH,
- (b3) optionally substitution of the amide functional group formed in the preceding step (a3) to yield a compound of formula (I) wherein $$X_1 = X_2 = -NR_6-C(O)-$$

and $R_5$=H with $R_6 \neq$ H and $R_6 \neq$ OH,
- (c3) optionally salification of the compound of formula (I) obtained in the preceding step to yield a pharmaceutically acceptable salt of same, and
- (d3) separation of the compound of formula (I) obtained in the preceding step from the reaction medium.

14. A method for preparing a compound of formula (I) according to claim 1, wherein $R_3$=—$NR_{46}R_{47}$, —$NR_{48}$-aryl, —$NR_{48}$-aralkyl, —$NR_{48}$-heteroaryl, —$NR_{48}$-carbocycle, —$NR_{48}$-heterocycle, —$NR_{48}CO$-aryl, —$NR_{48}CO-(C_1-C_6)$alkyl, —$NR_{48}CO$-aralkyl, —$NR_{48}CO$-heteroaryl, —$NR_{48}CO$-carbocycle, —$NR_{48}CO$-heterocycle, —$NR_{48}SO_2-(C_1-C_6)$alkyl, —$NR_{48}SO_2$-aryl, —$NR_{48}SO_2$-aralkyl, —$NR_{48}SO_2$-heteroaryl, —$NR_{48}SO_2$-carbocycle, or —$NR_{48}SO_2$-heterocycle, comprising the following successive steps:

- (a4) reaction of a compound of following formula (X):

(X)

wherein $A_5$ represents a $(C_1-C_6)$alkyl group and $R_1$, $R_2$, $R_4$, $X_1$ and $X_2$ are as defined in claim 1,
with a hydrazine of formula $R_5NH-NH_2$, wherein $R_5$ is as defined in claim 1, to yield a compound of formula (I) wherein $R_3$=$NH_2$,
- (b4) optionally substitution of the $NH_2$ functional group of the compound of formula (I) obtained in preceding step (a4) to yield a compound of formula (I) wherein $R_3$=—$NR_{46}R_{47}$ with $R_{46}$ and/or $R_{47}$ not representing a hydrogen atom, —$NR_{48}$-aryl, —$NR_{48}$-aralkyl, —$NR_{48}$-heteroaryl, —$NR_{48}$-carbocycle, —$NR_{48}$-heterocycle, —$NR_{48}CO$-aryl, —$NR_{48}CO-(C_1-C_6)$alkyl, —$NR_{48}CO$-aralkyl, —$NR_{48}CO$-heteroaryl, —$NR_{48}CO$-carbocycle, —$NR_{48}CO$-heterocycle, —$NR_{48}SO_2-(C_1-C_6)$alkyl, —$NR_{48}SO_2$-aryl, —$NR_{48}SO_2$-aralkyl, —$NR_{48}SO_2$-heteroaryl, —$NR_{48}SO_2$-carbocycle, or —$NR_{48}SO_2$-heterocycle,
- (c4) optionally salification of the compound of formula (I) obtained in the preceding step to yield a pharmaceutically acceptable salt of the compound of formula (I) obtained in the preceding step, and
- (d4) separation of the compound of formula (I) obtained in the preceding step from the reaction medium.

15. A method for preparing a compound of formula (I) according to claim 1, wherein $R_5$=H, $$X_1 = X_2$$

represents a —C(O)— group and ---- represents a double bond between the carbon atoms carrying the radicals $R_1$ and $R_2$, comprising the following successive steps:
- (a5) intramolecular cyclization under acid conditions of a compound of following formula (XI):

(XI)

wherein $A_8$ represents a $(C_1-C_6)$alkoxy group and $R_1$, $R_2$, $R_3$ and $R_4$ are as defined in claim 1,
to yield a compound of formula (I) wherein $R_5$=H, $$X_1 = X_2$$

represents a —C(=O)— group and ---- represents a double bond between the carbon atoms carrying the radicals $R_1$ and $R_2$, (a5) optionally salification of the compound of for (I) obtained in the preceding step to yield a pharmaceutically acceptable salt of the compound of formula (I) obtained in the preceding step, and (b5) separation of the compound of formula (I) obtained in the preceding step from the reaction medium.

16. The compound according to claim 1, wherein the mixture of stereoisomers is a mixture of enantiomers.

17. The compound according to claim 1, wherein the mixture of stereoisomers is a racemic mixture.

18. The compound according to claim 1, wherein $R_1$ and $R_2$ together form, with the carbon atoms that carry them, a ring selected from an aryl and a heteroaryl, said ring being optionally substituted by one or more groups selected from a halogen atom, an $OR_{26}$, $SR_{27}$, $NR_{28}R_{29}$, $(C_1\text{-}C_6)$alkyl, and heterocycle group, the $(C_1\text{-}C_6)$alkyl chains as well as the rings of the whole being optionally substituted by one or more groups selected from $OR_{43}$, $NR_{44}R_{45}$, —C(O)O—$(C_1\text{-}C_6)$-alkyl, heterocycle and $(C_1\text{-}C_6)$alkyl.

19. The compound according to claim 5, wherein $R_4$ represents an aryl, heteroaryl or aralkyl group, said group being optionally substituted by one or more groups selected from a halogen atom, an $OR_{50}$, $CO_2R_{55}$, $OCO_2R_{56}$, $(C_1\text{-}C_6)$alkyl, $(C_1\text{-}C_6)$haloalkyl, $OCOR_{67}$ group.

20. A method for treating cancer, comprising the administration to a person in need thereof of an effective amount of a compound according to claim 1.

21. A method for treating cancer, comprising, the administration to a person in need thereof of an effective amount of a pharmaceutical composition according to claim 8.

22. The pharmaceutical composition according to claim 9, wherein the at least one other active ingredient is an antineoplastic agent.

23. The method according to claim 12, wherein $A_2$ represents a halogen atom, a tosylate (OTs) or a mesylate (OMs).

24. The method according to claim 14, wherein the hydrazine of formula $R_5NH$—$NH_2$ is hydrazine $(NH_2)_2$.

* * * * *